United States Patent
Ackermann et al.

(10) Patent No.: US 8,124,636 B2
(45) Date of Patent: Feb. 28, 2012

(54) IMIDAZOLIDINONE DERIVATIVES AS 11B-HSD1 INHIBITORS

(75) Inventors: Jean Ackermann, Riehen (CH); Kurt Amrein, Itingen (CH); Bernd Kuhn, Liestal (CH); Alexander V. Mayweg, Basel (CH); Werner Neidhart, Hagenthal-le-Bas (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 102 days.

(21) Appl. No.: 12/424,587

(22) Filed: Apr. 16, 2009

(65) Prior Publication Data
US 2009/0275573 A1    Nov. 5, 2009

(30) Foreign Application Priority Data
Apr. 30, 2008 (EP) ..................... 08155430

(51) Int. Cl.
*A61K 31/4184* (2006.01)
*C07D 235/02* (2006.01)

(52) U.S. Cl. ..................... 514/387; 548/302.7
(58) Field of Classification Search ............... 548/302.7; 514/387
See application file for complete search history.

(56) References Cited

U.S. PATENT DOCUMENTS
2003/0203890 A1    10/2003    Steiner et al.

FOREIGN PATENT DOCUMENTS
| DE | 3809390 A1 * | 9/1989 |
| WO | WO 2006/024628 | 3/2006 |

OTHER PUBLICATIONS
Machine Translation of DE 3809390 A1.*
Machine Translation of DE 3809390 A1 (Jul. 29, 2011).*
Masuzaki H. et al., Science. Dec. 7, 2001; 294(5549):2166-70.
Walker et al. 1995; J. Clin. Endocrinol. Metab. 80, 3155-3159.
P.M. Stewart and Z.S. Krozowski, Vitam. Horm, 57 (1999), pp. 249-324.
Kotelevtsev Y. et al., Proc Nati Acad Sci U S A. Dec. 23, 1997;94(26):14924-9.
Masuzaki H. et al., J Clin Invest. Jul. 2003;112(1):83-90.
Rauz S. et al., QJM. Jul. 2003;96(7):481-90.
Sandeep TC. et al., Proc Natl. Acad Sci U S A. Apr. 27, 2004;101(17):6734-9.
Evans B.E. et al, *J. Med. Chem.* (1993) 36 3993-4005.
Winterfeld K et al, *Archiv der Pharmazie*, (1936) 276 40-47 XP002535696.
Nam K.-H. et al, *Arch. Pharm. Pharm. Med. Chem.* (1997) 330:8 268-270 XP002535697.
Dakin H.D. *Jour. of Biological Chem.* (1946) 164 615-620; XP002535698.

* cited by examiner

*Primary Examiner* — Jason M Nolan
(74) *Attorney, Agent, or Firm* — George W. Johnston; Dennis P. Tramaloni; Samuel H. Megerditchian

(57) ABSTRACT

Compounds of formula

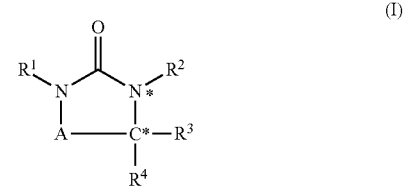

(I)

as well as pharmaceutically acceptable salts and esters thereof, wherein A and $R^1$ to $R^4$ have the significance given in claim 1 can be used in the form of pharmaceutical compositions.

11 Claims, No Drawings

IMIDAZOLIDINONE DERIVATIVES AS 11B-HSD1 INHIBITORS

PRIORITY TO RELATED APPLICATION(S)

This application claims the benefit of European Patent Application No. 08155430.5, filed Apr. 30, 2008, which is hereby incorporated by reference in its entirety.

FIELD OF THE INVENTION

The present invention is concerned with novel imidazolidinone derivatives useful as 11b-HSD1 inhibitors (T2D).

The invention is concerned particularly with compounds of formula I

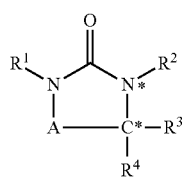

and pharmaceutically acceptable salts and esters thereof.

All documents relied upon or cited to below are expressly incorporated herein by reference.

BACKGROUND

Glucocorticoids (cortisol in humans, corticosterone in mice and rats) are an important class of adrenocorticosteroids that regulate many metabolic and homeostatic processes and form a key component of the response to stress. Glucocorticoids act via intracellular glucocorticoid receptors and, in some tissues, mineralocorticoid receptors; both being nuclear transcription factors. Glucocorticoid action on target tissues depends not only on circulating steroid concentrations and the cellular expression of receptors, but also on intracellular enzymes that critically determine to which extent glucocorticoids gain access to receptors in an active forms. 11beta-hydroxysteroid dehydrogenases (11beta-HSD's) catalyze the interconversion of the principal active 11-hydroxy-glucocorticoid (Cortisol in men) and their inactive 11-keto metabolites (cortisone in men).

The enzyme 11beta-hydroxysteroid dehydrogenase type 1 (11beta-HSD1) inter-converts inactive into active glucocorticoids, thereby playing a major role in local modulation of cellular agonist concentration and thus activation of corticosteroid receptors in target tissues. In a recent study made by F. Hoffmann-La Roche differences in gene expression in lean and obese men were analyzed using gene array technology in order to identify specific changes in gene expression that might be associated with insulin resistance or altered metabolism. This study revealed that the mRNA for 11beta-HSD1 is approximately two-fold up regulated in adipose tissue in obese individuals. Moreover, overexpressing 11beta-HSD1 in adipocytes of mice led to visceral obesity and to a syndrome-X like phenotype (Masuzaki H. et al., Science. 2001 Dec. 7; 294(5549):2166-70). Taken together, these data very strongly support an important role of 11beta-HSD1 in the induction of obesity and the impairment of glucose homeostasis and lipid parameters. Thus, selective inhibition of this enzyme could lower blood glucose levels in Type 2 diabetic patients, normalize elevated lipid parameters and/or reduce weight in obese subjects.

The first pharmacological indication that 11beta-HSD1 inhibition in men might have beneficial effects were obtained by using carbenoxolone, an anti-ulcer drug which inhibits both 11beta-HSD1 and the related enzyme 11beta-HSD2. Treatment with carbenoxolone led to an increase in insulin sensitivity indicating that that inhibition of 11beta-HSD1 may reduce cellular cortisol levels and therefore minimizing some of its deleterious effects. (Walker et al. 1995; J. Clin. Endocrinol. Metab. 80, 31155-3159).

11beta-HSD1 is expressed in many tissues including liver, adipose tissue, vascular smooth muscles, pancreas and brain. Its activity is dependent on NADP(H) and it has a relatively low affinity for its substrate (compared to 11beta-HSD2). 11beta-HSD1 in tissue homogenates and when purified is bidirectional, exhibiting both 11beta-dehydrogenase and 11beta-reductase reactions, with greater stability of the dehydrogenase activity (P. M. Stewart and Z. S. Krozowski, Vitam. Horm. 57 (1999), pp. 249-324). However, when the enzyme activity is tested in intact cells, the 11beta-reductase activity predominates, which regenerates active glucocorticoids from inert 11-keto forms. Such glucocorticoid regeneration will increase effective intracellular glucocorticoid levels and thereby amplifying glucocorticoid activity. It is this elevated cellular cortisol concentration that might lead to increased hepatic glucose production, adipocyte differentiation and insulin resistance.

Inhibition of 11beta-HSD1 should not only reduce the typical Syndrome-X/Diabetes associated symptoms, but it should also be safe and without major side effect. Studies with the unspecific inhibitor carbenoxolone highlight the importance of developing specific 11beta-HSD1 inhibitors. The inhibition of the 11beta-HSD2 enzyme is badly tolerated and results in increased blood pressure. In contrast inhibition of 11beta-HSD1 should be well tolerated since 11beta-HSD1 knockout mice were found be healthy and to resist hyperglycemia provoked by obesity or stress (Kotelevtsev Y. et al., Proc Natl Acad Sci USA. 1997 Dec. 23; 94(26):14924-9). Similar upon starvation these mice had attenuated activation of key hepatic enzymes that are involved in gluconeogenesis. In addition, these mice had improved lipid and lipoprotein profiles suggesting that inhibition of HSD1 might be highly efficacious and safe. Recent reports indicate that 11beta-HSD1 inhibitors might also be beneficial to reduce high blood pressure (Masuzaki H. et al., J Clin Invest. 2003 July, 112(1): 83-90; Rauz S. et al., QJM. 2003 July; 96(7):481-90) to improve cognition (Sandeep T C. et al., Proc Natl Acad Sci USA. 2004 Apr. 27; 101 (17):6734-9) or to improve Alzheimer associated deficits. Taken together 1beta-HSD1 inhibition might be a save and efficacious approach to treat symptoms of diabetes, obesity and other diseases.

SUMMARY OF THE INVENTION

In an embodiment of the present invention, provided is a compound according to formula (I):

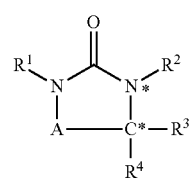

Wherein:

R¹ is a) bornyl, norbornyl, bicyclo[2.2.2]octanyl, or adamantyl, wherein bornyl, norbornyl, bicyclo[2.2.2]octanyl, or adamantyl are optionally substituted with one or two substituents independently selected from hydroxy, alkoxy, halogen, alkyl, hydroxyallyl, amino, aminocarbonyl, alkoxycarbonyl, hydroxycarbonyl, alkylcarbonylamino, alkyl-S(O)₂—, alkyl-S(O)₂-amino, haloalkyl-S(O)₂-amino, alkoxycarbonylamino-S(O)₂-amino, amino-S(O)₂-amino, hydroxyalkylcarbonylamino, aminocarbonylamino, haloalkoxy; and, wherein A is CR⁵R⁶ or carbonyl; or b) phenyl, phenylalkyl, substituted phenyl or substituted phenylalkyl, wherein substituted phenyl and substituted phenylalkyl are substituted with one or two substituents independently selected from alkyl, halogen, haloalkyl, alkoxy, hydroxy and haloalkoxy; and, wherein A is CR⁵R⁶ and none of R⁹, R¹⁰, R¹¹ and R¹² is hydroxy and R¹³ and R¹⁴ are not hydrogen at the same time;

R² and R³ together with the nitrogen atom N* and the carbon atom C* to which they are attached form B, C, D, E, F or G

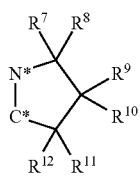

B

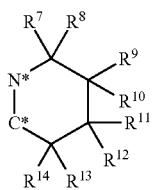

C

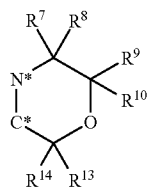

D

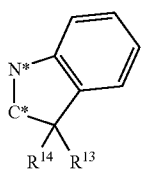

E

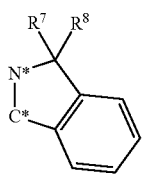

F

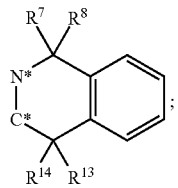

G

R⁴ is hydrogen, alkyl, cycloalkyl, cycloalkylalkyl, alkoxyalkyl, arylalkyl, arylalkoxy, arylalkoxyalkyl, hydroxyalkyl, aryl, heteroarylalkyl, heteroaryloxyalkyl, substituted aryl, substituted heteroarylalkyl or substituted heteroaryloxyalkyl, wherein substituted aryl, substituted heteroarylalkyl and substituted heteroaryloxyalkyl are substituted with one to three substituents independently selected from alkyl, cycloalkyl, cyano, halogen, haloalkyl, hydroxy and alkoxy;

R⁵ is hydrogen;
R⁶ is hydrogen;
one of R⁷ and R⁸ is hydrogen or halogen and the other one is hydrogen, halogen, hydroxy, alkoxy or arylalkoxy;
one of R⁹ and R¹⁰ is hydrogen or halogen and the other one is hydrogen, halogen, hydroxy, alkoxy or arylalkoxy;
one of R¹¹ and R¹² is hydrogen or halogen and the other one is hydrogen, halogen, hydroxy, alkoxy or arylalkoxy,
one of R¹³ and R¹⁴ is hydrogen or halogen and the other one is hydrogen, halogen, hydroxy, alkoxy or arylalkoxy;

or a pharmaceutically acceptable salt thereof.

In another embodiment of the present invention, provided is a process for the preparation of a compound of formula (I) comprising one of the following reactions: (a) the reaction of a compound according to formula (Ia)

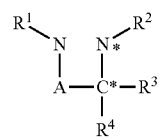

(Ia)

(b) the reaction of a compound of formula (Ib)

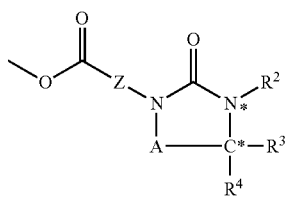

(Ib)

in the presence of a base,
wherein A, R¹, R², R³ and R⁴ are defined above, and wherein Z represents a bornane, norbornane, bicyclo[2.2.2]octane or adamantane.

In a further embodiment of the present invention, provided is a pharmaceutical composition, comprising a therapeutically effective amount of a compound according to claim 1 and a therapeutically acceptable carrier.

DETAILED DESCRIPTION

The compounds of formula I and their pharmaceutically acceptable salts and esters are novel and have valuable pharmacological properties. In particular they are 11b-HSD1 inhibitors (T2D) and they display selectivity against the related 11beta-HSD2 enzyme. Therefore the compounds which are specific 11beta-HSD1 inhibitors (T2D) represent an approach to e.g. lower blood glucose levels and normalize lipid parameters in Type 2 diabetic patients by modulating the local concentration of the active glucocorticoid cortisol in target tissue (liver, adipose tissue).

The compounds of the present invention can be used in the prophylaxis and/or treatment of metabolic disorders, obesity, dyslipidemiae and/or diabetes, particularly diabetes Type II.

The compounds of this invention can further be used in the prophylaxis and/or treatment of high ocular eye pressure, cognition, hypertension, Alzheimer and/or neurodegeneration.

Further, the compounds of this invention can be used for promoting wound healing, particularly by topical application. Moreover, the compounds of the present invention can be used to improve cognitive impairment, particularly impairment developed with age, and improvement of memory.

Embodiments of the present invention are the compounds of formula I and their aforementioned salts and esters per se and their use as therapeutically active substances, a process for the manufacture of the said compounds, intermediates, pharmaceutical compositions, medicaments containing the said compounds, their pharmaceutically acceptable salts and esters, the use of the said compounds, esters and salts for the prophylaxis and/or therapy of illnesses, especially in the treatment or prophylaxis of eating disorders, obesity, dyslipidemiae and/or diabetes, particularly diabetes Type II, and the use of the said compounds, salts and esters for the production of medicaments for the treatment or prophylaxis of metabolic disorders, obesity, dyslipidemiae and/or diabetes, particularly diabetes Type II.

The compounds of the present invention can further be combined with PPAR (alpha, gamma, delta) agonists, DHEA (dehydroepiandrosterone), DPPIV inhibitors, insulin and/or lipase inhibitors, particularly orlistat.

In the present description the term "alkyl", alone or in combination, signifies a straight-chain or branched-chain allyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl. Preferred cycloalkyl are cyclopropyl, methyl-cyclopropyl and particularly 1-methyl-cyclopropyl. Particularly preferred is cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy, preferably methoxy and ethoxy and most preferred methoxy.

The term "hydroxyalkyl", alone or in combination, signifies an alkyl group as defined before, wherein one or more hydrogen atoms, preferably one hydrogen atom is replaced by a hydroxy group. Examples of hydroxyalkyl are hydroxymethyl and hydroxyethyl.

The term "aryl", alone or in combination, signifies a phenyl or naphthyl group, preferably a phenyl group which optionally carries one or more substituents, preferably one to three, each independently selected from halogen, trifluoromethyl, trifluoromethoxy, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, alkyl-$SO_2$—, amino-$SO_2$—, cycloalkyl and the like. Examples are phenyl or naphthyl, particularly phenyl optionally substituted with one to three, preferably one or two substituents independently selected from alkyl, halogen, alkoxy, trifluoromethoxy and trifluoromethyl.

The term "heteroaryl" refers to an aromatic 5 to 6 membered monocyclic ring or 9 to 10 membered bicyclic ring which can comprise 1, 2 or 3 atoms selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzoimidazolyl, indolyl, indazolyl, benzoisothiazolyl, benzoxazolyl, benzoisoxazolyl and quinolinyl. Preferred heteroaryl groups are pyridinyl, oxazolyl and triazolyl, particularly pyridinyl. A heteroaryl group may optionally have a substitution pattern as described earlier in connection with the term "aryl".

The term "aryloxy", alone or in combination, signifies a aryl-O— group in which the term "aryl" has the previously given significance.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —$NH_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "halogen", alone or in combination, signifies fluorine, chlorine, bromine or iodine, preferably fluorine or chlorine, and most preferred fluorine.

The term "carbonyl", alone or in combination, signifies the —C(O)— group.

The terms "hydroxycarbonyl" or "carboxy", alone or in combination, signify the —C(O)OH group.

The term "oxy", alone or in combination, signifies the —O— group.

The term "nitro", alone or in combination signifies the —$NO_2$ group.

The term "cyano", alone or in combination signifies the group —CN.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention the asymmetric carbon atom can be of the "R" or "S" configuration.

Preferred are the compounds of formula I and pharmaceutically acceptable salts thereof, particularly the compounds of formula I.

Preferred are compounds of formula I, wherein $R^1$ is bicyclo[2.2.2]octanyl, adamantyl, substituted bicyclo[2.2.2]octanyl or substituted adamantyl, wherein substituted bicyclo[2.2.2]octanyl and substituted adamantyl are substituted with one or two substituents independently selected from hydroxy, aminocarbonyl, alkoxycarbonyl, hydroxycarbonyl, alkylcarbonylamino and alkyl-S(O)$_2$—.

Further preferred are compounds of formula I, wherein $R^1$ is hydroxy-adamantyl, methoxycarbonyl-adamantyl, carboxy-adamantyl, aminocarbonyl-adamantyl, or aminocarbonyl-bicyclo[2.2.2]octanyl.

Further preferred are compounds of formula I, wherein $R^1$ is hydroxy-adamantyl, carboxy-adamantyl, aminocarbonyl-adamantyl, or aminocarbonyl-bicyclo[2.2.2]octanyl.

Preferred are compounds of formula I, wherein $R^1$ is phenyl, phenylalkyl, substituted phenyl or substituted phenylalkyl, wherein substituted phenyl and substituted phenylalkyl are substituted with one or two substituents independently selected from alkyl, halogen and haloalkyl.

Also preferred are compounds of formula I, wherein $R^1$ is phenyl, chlorobenzyl, benzyl, chlorophenylethyl, phenylethyl, difluorobenzyl, dichlorophenyl, trifluoromethylphenyl or difluorophenylethyl.

Preferred are compounds of formula I, wherein A is $CR^5R^5$.

Preferred are compounds of formula I, wherein $R^2$ and $R^3$ together with the nitrogen atom N* and the carbon atom C* to which they are attached form B or C

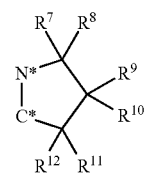

B

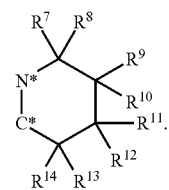

C

Further preferred are compounds of formula I, wherein $R^2$ and $R^3$ together with the nitrogen atom N* and the carbon atom C* to which they are attached form

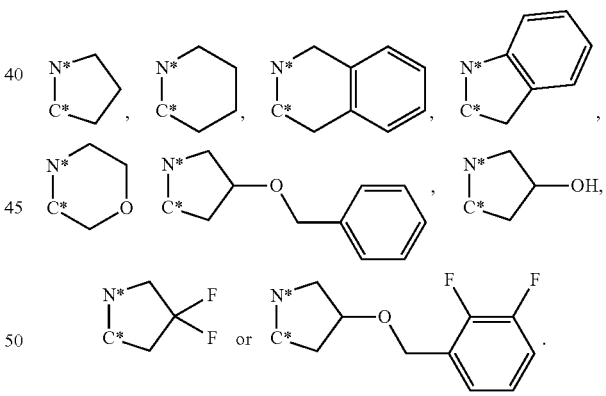

Also preferred are compounds of formula I, wherein $R^2$ and $R^3$ together with the nitrogen atom N* and the carbon atom C* to which they are attached form

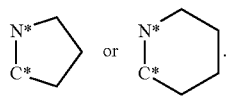

Also preferred are compounds of formula I, wherein $R^2$ and $R^3$ together with the nitrogen atom N* and the carbon atom C* to which they are attached form

Preferred are compounds of formula I, wherein $R^4$ is alkyl, cycloalkylalkyl, alkoxyalkyl, phenylalkyl, phenylalkoxy, phenylalkoxyalkyl, hydroxyalkyl, pyridinylalkyl, pyridinyloxyalkyl, substituted phenyl, substituted pyridinylalkyl or substituted pyridinyloxyalkyl, wherein substituted phenyl, substituted pyridinylalkyl and substituted pyridinyloxyalkyl are substituted with one to three substituents independently selected from, cyano, halogen, haloalkyl and alkoxy.

Also preferred are compounds of formula I, wherein $R^4$ is methyl, benzyloxymethyl, benzyl, cyanopyridinyloxymethyl, hydroxymethyl, trifluoromethylpyridinyloxymethyl, methoxymethyl, difluorobenzyloxymethyl, phenyl, phenethyl, cyclopropylmethyl, chlorophenyl, fluorophenyl, chlorophenyl, dichlorophenyl, difluorophenyl, or methoxyphenyl.

Also preferred are compounds of formula I, wherein $R^4$ is methyl, benzyloxymethyl, benzyl, cyanopyridinyloxymethyl, hydroxymethyl, 5-trifluoromethyl-pyridin-2-yloxymethyl, methoxymethyl, 2,4-difluoro-benzyloxymethyl, phenyl, phenethyl, cyclopropylmethyl, 4-chlorophenyl, 2-fluoro-phenyl, 3-chloro-phenyl, 4-fluoro-phenyl, 2,4-dichloro-phenyl, 2,4-difluoro-phenyl or 3-methoxy-phenyl.

Preferred are compounds of formula I, wherein $R^4$ is methyl, cyanopyridinyloxymethyl, cyclopropylmethyl, fluorophenyl or chlorophenyl.

Further preferred are compounds of formula I, wherein $R^4$ is cyanopyridinyloxymethyl, cyclopropylmethyl, 3-chlorophenyl or 4-fluoro-phenyl.

Preferred examples of compounds of formula I are:
1. (S)-2-((Z)-5-Hydroxy-adamantan-2-yl)-7a-methyl-hexahydro-pyrrolo[1,2-c]imidazol-3-one;
2. (S)-2-((E)-5-Hydroxy-adamantan-2-yl)-7a-methyl-hexahydro-pyrrolo[1,2-c]imidazol-3-one;
3. (S)-2-((Z)-5-Hydroxy-adamantan-2-yl)-hexahydro-pyrrolo[1,2-c]imidazol-3-one;
4. (S)-2-((E)-5-Hydroxy-adamantan-2-yl)-hexahydro-pyrrolo[1,2-c]imidazol-3-one;
5. (S)-2-Phenyl-hexahydro-pyrrolo[1,2-c]imidazol-3-one;
6. (S)-2-((Z)-5-Hydroxy-adamantan-2-yl)-hexahydro-imidazo[1,5-a]pyridin-3-one;
7. (S)-2-((E)-5-Hydroxy-adamantan-2-yl)-hexahydro-imidazo[1,5-a]pyridin-3-one;
8. (rac)-(E/Z)-4-(3-Oxo-tetrahydro-pyrrolo[1,2-c]imidazol-2-yl)-adamantane-1-carboxylic acid methyl ester;
9. (S)-2-((Z)-5-Hydroxy-adamantan-2-yl)-1,5,10,10a-tetrahydro-2H-imidazo[1,5-b]isoquinolin-3-one;
10. (S)-2-((E)-5-Hydroxy-adamantan-2-yl)-1,5,10,10a-tetrahydro-2H-imidazo[1,5-b]isoquinolin-3-one;
11. (rac)-(E/Z)-4-(3-Oxo-tetrahydro-pyrrolo[1,2-c]imidazol-2-yl)-adamantane-1-carboxylic acid;
12. (rac)-7a-Benzyloxymethyl-2-((E/Z)-5-hydroxy-adamantan-2-yl)-hexahydro-pyrrolo[1,2-c]imidazol-3-one;
13. (R)-7a-Benzyl-2-((Z)-5-hydroxy-adamantan-2-yl)-hexahydro-pyrrolo[1,2-c]imidazol-3-one;
14. (R)-7a-Benzyl-2-((E)-5-hydroxy-adamantan-2-yl)-hexahydro-pyrrolo[1,2-c]imidazol-3-one;
15. (R)-7a-Benzyl-2-((E/Z)-5-hydroxy-adamantan-2-yl)-tetrahydro-pyrrolo[1,2-c]imidazole-1,3-dione;
16. (E)-4-((S)-3-Oxo-tetrahydro-pyrrolo[1,2-c]imidazol-2-yl)-adamantane-1-carboxylic acid amide;
17. (rac)-2-((E/Z)-5-Hydroxy-adamantan-2-yl)-7a-hydroxymethyl-hexahydro-pyrrolo[1,2-c]imidazol-3-one;
18. (rac)-6-[2-((E/Z)-5-Hydroxy-adamantan-2-yl)-3-oxo-tetrahydro-pyrrolo[1,2-c]imidazol-7a-ylmethoxy]-nicotinonitrile;
19. (S)-2-((Z)-5-Hydroxy-adamantan-2-yl)-1,2,9,9a-tetrahydro-imidazo[1,5-a]indol-3-one;
20. (S)-2-((E)-5-Hydroxy-adamantan-2-yl)-1,2,9,9a-tetrahydro-imidazo[1,5-a]indol-3-one;
21. (R)-2-((Z)-5-Hydroxy-adamantan-2-yl)-hexahydro-pyrrolo[1,2-c]imidazol-3-one;
22. (R)-2-((E)-5-Hydroxy-adamantan-2-yl)-hexahydro-pyrrolo[1,2-c]imidazol-3-one;
23. (rac)-2-((E/Z)-5-Hydroxy-adamantan-2-yl)-hexahydro-imidazo[5,1-c][1,4]oxazin-3-one;
24. (rac)-2-((E)-5-Hydroxy-adamantan-2-yl)-7a-hydroxymethyl-hexahydro-pyrrolo[1,2-c]imidazol-3-one;
25. (rac)-2-((Z)-5-Hydroxy-adamantan-2-yl)-8a-methyl-hexahydro-imidazo[1,5-a]pyridin-3-one;
26. (rac)-2-((E)-5-Hydroxy-adamantan-2-yl)-8a-methyl-hexahydro-imidazo[1,5-a]pyridin-3-one;
27. 6-[(rac)-2-((E)-5-Hydroxy-adamantan-2-yl)-3-oxo-tetrahydro-pyrrolo[1,2-c]imidazol-7a-ylmethoxy]-nicotinonitrile;
28. (rac)-2-((Z)-5-Hydroxy-adamantan-2-yl)-7a-(5-trifluoromethyl-pyridin-2-yloxymethyl)-hexahydro-pyrrolo[1,2-c]imidazol-3-one;
29. (rac)-2-((E)-5-Hydroxy-adamantan-2-yl)-7a-(5-trifluoromethyl-pyridin-2-yloxymethyl)-hexahydro-pyrrolo[1,2-c]imidazol-3-one;
30. (6R,7aS)-6-Benzyloxy-2-((Z)-5-hydroxy-adamantan-2-yl)-hexahydro-pyrrolo[1,2-c]imidazol-3-one;
31. (6R,7aS)-6-Benzyloxy-2-((E)-5-hydroxy-adamantan-2-yl)-hexahydro-pyrrolo[1,2-c]imidazol-3-one;
32. (6R,7aS)-6-Hydroxy-2-((E)-5-hydroxy-adamantan-2-yl)-hexahydro-pyrrolo[1,2-c]imidazol-3-one;
33. (rac)-2-((E/Z)-5-Hydroxy-adamantan-2-yl)-7a-methoxymethyl-hexahydro-pyrrolo[1,2-c]imidazol-3-one;
34. (rac)-7a-(2,4-Difluoro-benzyloxymethyl)-2-((E)-5-hydroxy-adamantan-2-yl)-hexahydro-pyrrolo[1,2-c]imidazol-3-one;
35. (S)-2-((E)-5-Hydroxy-adamantan-2-yl)-8a-methyl-hexahydro-imidazo[1,5-a]pyridin-3-one;
36. (R)-2-((E)-5-Hydroxy-adamantan-2-yl)-8a-methyl-hexahydro-imidazo[1,5-a]pyridin-3-one;
37. (S)-2-((E)-5-Hydroxy-adamantan-2-yl)-7a-hydroxymethyl-hexahydro-pyrrolo[1,2-c]imidazol-3-one;
38. (R)-2-((E)-5-Hydroxy-adamantan-2-yl)-7a-hydroxymethyl-hexahydro-pyrrolo[1,2-c]imidazol-3-one;
39. (rac)-2-((Z)-5-Hydroxy-adamantan-2-yl)-1,2,5,9b-tetrahydro-imidazo[5,1-a]isoindol-3-one;
40. (rac)-2-((E)-5-Hydroxy-adamantan-2-yl)-1,2,5,9b-tetrahydro-imidazo[5,1-a]isoindol-3-one;
41. (rac)-2-((Z)-5-Hydroxy-adamantan-2-yl)-7a-phenyl-hexahydro-pyrrolo[1,2-c]imidazol-3-one;
42. (rac)-2-((E)-5-Hydroxy-adamantan-2-yl)-7a-phenyl-hexahydro-pyrrolo[1,2-c]imidazol-3-one;
43. 6-[(S)-2-((E)-5-Hydroxy-adamantan-2-yl)-3-oxo-tetrahydro-pyrrolo[1,2-c]imidazol-7a-ylmethoxy]-nicotinonitrile;
44. N-{(E)-4-[(R)-7a-(4-Fluoro-phenyl)-3-oxo-tetrahydro-pyrrolo[1,2-c]imidazol-2-yl]-adamantan-1-yl}-acetamide;
45. (rac)-8a-Benzyloxymethyl-2-((Z)-5-hydroxy-adamantan-2-yl)-hexahydro-imidazo[1,5-a]pyridin-3-one;
46. (rac)-8a-Benzyloxymethyl-2-((E)-5-hydroxy-adamantan-2-yl)-hexahydro-imidazo[1,5-a]pyridin-3-one;

47. (E/Z)-4-((rac)-7a-Benzyloxymethyl-3-oxo-tetrahydro-pyrrolo[1,2-c]imidazol-2-yl)-adamantane-1-carboxylic acid methyl ester;
48. (R)-2-((Z)-5-Hydroxy-adamantan-2-yl)-7a-phenethyl-hexahydro-pyrrolo[1,2-c]imidazol-3-one;
49. (R)-2-((E)-5-Hydroxy-adamantan-2-yl)-7a-phenethyl-hexahydro-pyrrolo[1,2-c]imidazol-3-one;
50. (rac)-2-(2-Chloro-benzyl)-7a-methyl-hexahydro-pyrrolo[1,2-c]imidazol-3-one;
51. (rac)-2-Benzyl-7a-methyl-hexahydro-pyrrolo[1,2-c]imidazol-3-one;
52. (E/Z)-4-((rac)-7a-Hydroxymethyl-3-oxo-tetrahydro-pyrrolo[1,2-c]imidazol-2-yl)-adamantane-1-carboxylic acid methyl ester;
53. (E/Z)-4-((rac)-7a-Benzyloxymethyl-3-oxo-tetrahydro-pyrrolo[1,2-c]imidazol-2-yl)-adamantane-1-carboxylic acid;
54. (S)-6,6-Difluoro-2-((Z)-5-hydroxy-adamantan-2-yl)-hexahydro-pyrrolo[1,2-c]imidazol-3-one;
55. (S)-6,6-Difluoro-2-((E)-5-hydroxy-adamantan-2-yl)-hexahydro-pyrrolo[1,2-c]imidazol-3-one;
56. (E/Z)-4-[(rac)-7a-(5-Cyano-pyridin-2-yloxymethyl)-3-oxo-tetrahydro-pyrrolo[1,2-c]imidazol-2-yl]-adamantane-1-carboxylic acid methyl ester;
57. (6R,7aS)-6-(2,4-Difluoro-benzyloxy)-2-((E)-5-hydroxy-adamantan-2-yl)-hexahydro-pyrrolo[1,2-c]imidazol-3-one;
58. 6-[(rac)-2-((E)-5-Hydroxy-adamantan-2-yl)-3-oxo-hexahydro-imidazo[1,5-a]pyridin-8a-ylmethoxy]-nicotinonitrile;
59. (rac)-2-[1-(4-Chloro-phenyl)-ethyl]-7a-methyl-hexahydro-pyrrolo[1,2-c]imidazol-3-one;
60. (rac)-2-(3-Chloro-benzyl)-7a-methyl-hexahydro-pyrrolo[1,2-c]imidazol-3-one;
61. (rac)-7a-Methyl-2-(1-phenyl-ethyl)-hexahydro-pyrrolo[1,2-c]imidazol-3-one;
62. (E/Z)-4-((rac)-7a-Benzyloxymethyl-3-oxo-tetrahydro-pyrrolo[1,2-c]imidazol-2-yl)-adamantane-1-carboxylic acid amide;
63. (E/Z)-4-[(rac)-7a-(5-Cyano-pyridin-2-yloxymethyl)-3-oxo-tetrahydro-pyrrolo[1,2-c]imidazol-2-yl]-adamantane-1-carboxylic acid amide;
64. (rac)-7a-Cyclopropylmethyl-2-((Z)-5-hydroxy-adamantan-2-yl)-hexahydro-pyrrolo[1,2-c]imidazol-3-one;
65. (rac)-7a-Cyclopropylmethyl-2-((E)-5-hydroxy-adamantan-2-yl)-hexahydro-pyrrolo[1,2-c]imidazol-3-one;
66. (rac)-6,6-Difluoro-2-((Z)-5-hydroxy-adamantan-2-yl)-7a-methyl-hexahydro-pyrrolo[1,2-c]imidazol-3-one;
67. (rac)-7a-(4-Chloro-phenyl)-2-((E)-5-hydroxy-adamantan-2-yl)-hexahydro-pyrrolo[1,2-c]imidazol-3-one;
68. (rac)-2-(3-Chloro-phenyl)-7a-methyl-hexahydro-pyrrolo[1,2-c]imidazol-3-one;
69. (rac)-2-((E/Z)-5-Methanesulfonyl-adamantan-2-yl)-7a-phenyl-hexahydro-pyrrolo[1,2-c]imidazol-3-one;
70. (rac)-2-(2,4-Difluoro-benzyl)-7a-methyl-hexahydro-pyrrolo[1,2-c]imidazol-3-one;
71. (rac)-2-(2-Chloro-phenyl)-7a-methyl-hexahydro-pyrrolo[1,2-c]imidazol-3-one;
72. (rac)-2-(4-Chloro-benzyl)-7a-methyl-hexahydro-pyrrolo[1,2-c]imidazol-3-one;
73. (rac)-2-(2,4-Dichloro-phenyl)-7a-methyl-hexahydro-pyrrolo[1,2-c]imidazol-3-one;
74. (rac)-6,6-Difluoro-2-((E)-5-hydroxy-adamantan-2-yl)-7a-methyl-hexahydro-pyrrolo[1,2-c]imidazol-3-one;
75. (S)-2-(3-Chloro-phenyl)-6,6-difluoro-hexahydro-pyrrolo[1,2-c]imidazol-3-one;
76. (rac)-7a-Methyl-2-(2-trifluoromethyl-phenyl)-hexahydro-pyrrolo[1,2-c]imidazol-3-one;
77. (rac)-2-(2,5-Dichloro-phenyl)-7a-methyl-hexahydro-pyrrolo[1,2-c]imidazol-3-one;
78. (rac)-6-Benzyloxy-2-((Z)-5-hydroxy-adamantan-2-yl)-7a-methyl-hexahydro-pyrrolo[1,2-c]imidazol-3-one;
79. (rac)-2-[1-(2-Chloro-phenyl)-ethyl]-7a-methyl-hexahydro-pyrrolo[1,2-c]imidazol-3-one;
80. (rac)-2-[1-(2,4-Difluoro-phenyl)-ethyl]-7a-methyl-hexahydro-pyrrolo[1,2-c]imidazol-3-one;
81. (rac)-2-[1-(3-Chloro-phenyl)-ethyl]-7a-methyl-hexahydro-pyrrolo[1,2-c]imidazol-3-one;
82. (rac)-6-Benzyloxy-2-((E)-5-hydroxy-adamantan-2-yl)-7a-methyl-hexahydro-pyrrolo[1,2-c]imidazol-3-one;
83. (rac)-7a-(2-Fluoro-phenyl)-2-((Z)-5-hydroxy-adamantan-2-yl)-hexahydro-pyrrolo[1,2-c]imidazol-3-one;
84. (rac)-7a-(2-Fluoro-phenyl)-2-((E)-5-hydroxy-adamantan-2-yl)-hexahydro-pyrrolo[1,2-c]imidazol-3-one;
85. (rac)-7a-(3-Chloro-phenyl)-2-((E)-5-hydroxy-adamantan-2-yl)-hexahydro-pyrrolo[1,2-c]imidazol-3-one;
86. (rac)-7a-(4-Fluoro-phenyl)-2-((E)-5-hydroxy-adamantan-2-yl)-hexahydro-pyrrolo[1,2-c]imidazol-3-one;
87. (rac)-7a-(2,4-Dichloro-phenyl)-2-((E)-5-hydroxy-adamantan-2-yl)-hexahydro-pyrrolo[1,2-c]imidazol-3-one;
88. (E)-4-[(R)-7a-(4-Fluoro-phenyl)-3-oxo-tetrahydro-pyrrolo[1,2-c]imidazol-2-yl]-adamantane-1-carboxylic acid amide;
89. (Z)-4-((rac)-7a-Cyclopropylmethyl-3-oxo-tetrahydro-pyrrolo[1,2-c]imidazol-2-yl)-adamantane-1-carboxylic acid amide;
90. (E)-4-((rac)-7a-Cyclopropylmethyl-3-oxo-tetrahydro-pyrrolo[1,2-c]imidazol-2-yl)-adamantane-1-carboxylic acid amide;
91. 4-[(rac)-7a-(4-Fluoro-phenyl)-3-oxo-tetrahydro-pyrrolo[1,2-c]imidazol-2-yl]-bicyclo[2.2.2]octane-1-carboxylic acid amide;
92. (S)-7a-(4-Fluoro-phenyl)-2-((E)-5-hydroxy-adamantan-2-yl)-hexahydro-pyrrolo[1,2-c]imidazol-3-one;
93. (R)-7a-(4-Fluoro-phenyl)-2-((E)-5-hydroxy-adamantan-2-yl)-hexahydro-pyrrolo[1,2-c]imidazol-3-one;
94. (rac)-7a-(2,4-Difluoro-phenyl)-2-((Z)-5-hydroxy-adamantan-2-yl)-hexahydro-pyrrolo[1,2-c]imidazol-3-one;
95. (rac)-7a-(2,4-Difluoro-phenyl)-2-((E)-5-hydroxy-adamantan-2-yl)-hexahydro-pyrrolo[1,2-c]imidazol-3-one;
96. (rac)-2-((Z)-5-Hydroxy-adamantan-2-yl)-7a-(3-methoxy-phenyl)-hexahydro-pyrrolo[1,2-c]imidazol-3-one;
97. (rac)-2-((E)-5-Hydroxy-adamantan-2-yl)-7a-(3-methoxy-phenyl)-hexahydro-pyrrolo[1,2-c]imidazol-3-one;
98. 4-[(rac)-7a-(3-Chloro-phenyl)-3-oxo-tetrahydro-pyrrolo[1,2-c]imidazol-2-yl]-bicyclo[2.2.2]octane-1-carboxylic acid amide;
99. 4-[(S)-7a-(3-Chloro-phenyl)-3-oxo-tetrahydro-pyrrolo[1,2-c]imidazol-2-yl]-bicyclo[2.2.2]octane-1-carboxylic acid amide;
100. 4-[(R)-7a-(3-Chloro-phenyl)-3-oxo-tetrahydro-pyrrolo[1,2-c]imidazol-2-yl]-bicyclo[2.2.2]octane-1-carboxylic acid amide;
101. 4-((rac)-7a-Cyclopropylmethyl-3-oxo-tetrahydro-pyrrolo[1,2-c]imidazol-2-yl)-bicyclo[2.2.2]octane-1-carboxylic acid amide;
102. 4-((S)-7a-Cyclopropylmethyl-3-oxo-tetrahydro-pyrrolo[1,2-c]imidazol-2-yl)-bicyclo[2.2.2]octane-1-carboxylic acid amide; and
103. 4-((R)-7a-Cyclopropylmethyl-3-oxo-tetrahydro-pyrrolo[1,2-c]imidazol-2-yl)-bicyclo[2.2.2]octane-1-carboxylic acid amide.

Particularly preferred examples of compounds of formula I are:

(S)-2-((E)-5-Hydroxy-adamantan-2-yl)-7a-methyl-hexahydro-pyrrolo[1,2-c]imidazol-3-one;

(rac)-2-((E)-5-Hydroxy-adamantan-2-yl)-8a-methyl-hexahydro-imidazo[1,5-a]pyridin-3-one;
6-[(S)-2-((E)-5-Hydroxy-adamantan-2-yl)-3-oxo-tetrahydro-pyrrolo[1,2-c]imidazol-7a-ylmethoxy]-nicotinonitrile;
(E/Z)-4-[(rac)-7a-(5-Cyano-pyridin-2-yloxymethyl)-3-oxo-tetrahydro-pyrrolo[1,2-c]imidazol-2-yl]-adamantane-1-carboxylic acid amide;
(rac)-7a-Cyclopropylmethyl-2-((E)-5-hydroxy-adamantan-2-yl)-hexahydro-pyrrolo[1,2-c]imidazol-3-one;
(rac)-7a-(3-Chloro-phenyl)-2-((E)-5-hydroxy-adamantan-2-yl)-hexahydro-pyrrolo[1,2-c]imidazol-3-one;
(E)-4-[(R)-7a-(4-Fluoro-phenyl)-3-oxo-tetrahydro-pyrrolo[1,2-c]imidazol-2-yl]-adamantane-1-carboxylic acid amide;
(E)-4-((rac)-7a-Cyclopropylmethyl-3-oxo-tetrahydro-pyrrolo[1,2-c]imidazol-2-yl)-adamantane-1-carboxylic acid amide;
4-[(rac)-7a-(4-Fluoro-phenyl)-3-oxo-tetrahydro-pyrrolo[1,2-c]imidazol-2-yl]-bicyclo[2.2.2]octane-1-carboxylic acid amide; and
(R)-7a-(4-Fluoro-phenyl)-2-((E)-5-hydroxy-adamantan-2-yl)-hexahydro-pyrrolo[1,2-c]imidazol-3-one.

Particularly preferred is the compound of formula (R)-7a-(4-Fluoro-phenyl)-2-((E)-5-hydroxy-adamantan-2-yl)-hexahydro-pyrrolo[1,2-c]imidazol-3-one.

Processes for the manufacture of compounds of formula I are an embodiment of the invention.

The preparation of compounds of formula I of the present invention may be carried out in sequential or convergent synthetic routes. Syntheses of the invention are shown in the following Schemes. The skills required for carrying out the reaction and purification of the resulting products are known to those persons skilled in the art. The substituents and indices used in the following description of the processes have the significance given above unless indicated to the contrary.

The preparation of compounds of formula I of the present invention may be carried out in sequential or convergent synthetic routes. Syntheses of the invention are shown in the following Schemes. The skills required for carrying out the reaction and purification of the resulting products are known to those persons skilled in the art. The substituents and indices used in the following description of the processes have the significance given above unless indicated to the contrary.

The following abbreviations are used:
BOC: butoxycarbonyl;
CBZ: carboxybenzyl;
LDA: lithium diisopropylamide;
LAH: lithium aluminium hydride;
TFA: trifluoroacetic acid;
DMS: dimethyl sulfide;
NBS: N-bromosuccinimide;
DCM: dichloromethane;
THF: tetrahydrofurane;
DMF: dimethylformamide;
DMP: Dess Martin Periodinane (1,1,1-triacetoxy-1,1-dihydro-1,2-benziodoxol-3(1H) one);
TEMPO: 2,2,6,6-tetramethylpiperidine-1-oxyl;
AIBN: azobisisobutyronitrile;
TBABr: tetra-n-butylammonium bromide;
EDCI: 1-Ethyl-3-(3-Dimethylaminopropyl)carbodiimide;
HOBT: Hydroxybenzotriazole.

Compounds of formula I are accessible according to the following general Scheme 1 starting from general compound starting material SM, for example SM1 (where $R^4$=H) or A (where $R^4 \neq H$) which are either commercially available or known in the literature or are prepared according to known literature procedures. The nitrogen atom featured in compound A or SM1 is suitably protected with for example BOC or CBZ groups. Compound A is doubly deprotonated according to known procedures with LDA (see Tetrahedron Letters 1992, 6461) and alkylated with an appropriate alkylhalide $R^4$—X under basic conditions to give intermediate B. Material B or SM1 is then coupled with the appropriately substituted amine $R^1$—$NH_2$ under standard coupling conditions to give intermediate C which is deprotected using either acidic (TFA) or hydrogenolytic conditions (Pd/C, $H_2$) as appropriate for the feature protecting group, to give intermediate D. Reduction of the amide to the amine was effected typically by using lithium aluminium hydride in reluxing THF to afford the diamine intermediate E. This material was converted into the bicyclic urea using triphosgene, diphosgene or other suitable phosgene equivalents affording bicyclic ureas of formula (I). These compounds were purified or separated into their E and Z isomers (for isomeric mixtures at $R^1$) by flash column chromatography over silica gel and/or separated into the pure enantiomers by chiral HPLC or by other chromatographic means as known to those skilled in the art.

Scheme 1

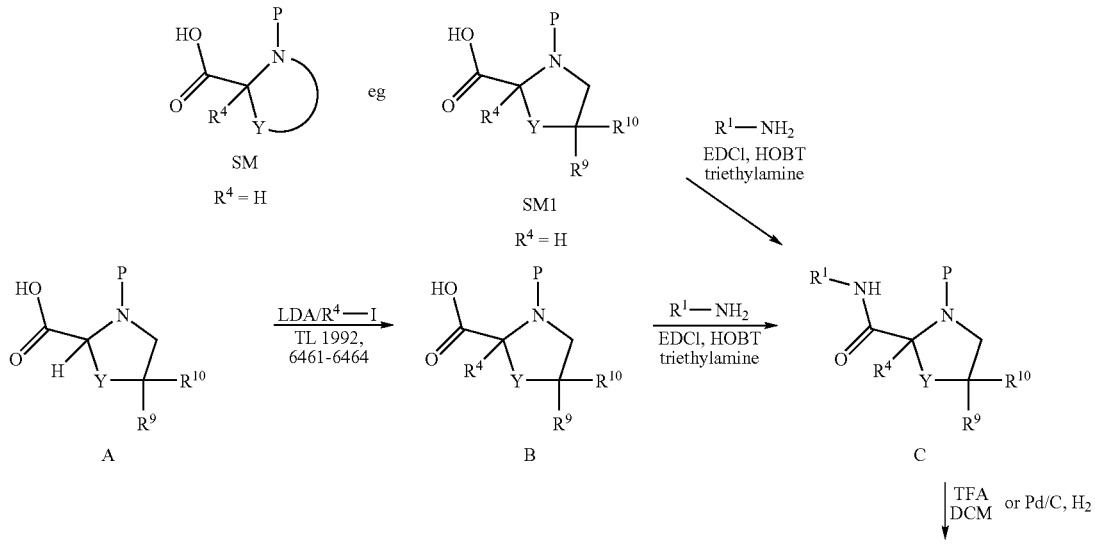

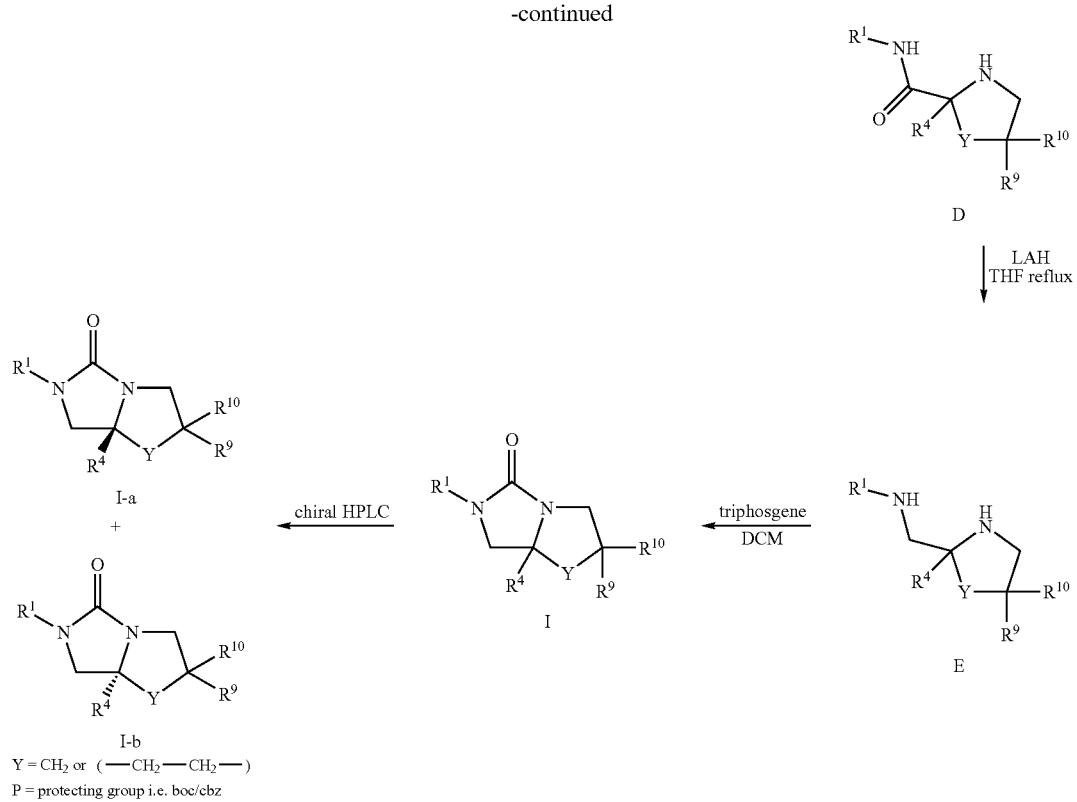

Alternatively, compounds of formula (I) can be prepared according to the general Scheme 2, starting from compound B which is reduced via borane reduction or equivalent methods to the alcohol G. Alternatively G can be accessed from the corresponding ester F via a reduction with lithium aluminium hydride. Intermediate G is oxidized to the aldehyde using for example Dess Martin Periodinane or TEMPO/ bleach oxidation or other means such as methods known to those experienced and skilled in the art, to give intermediate aldehyde H. Reductive amination of intermediate H with a suitably substituted amine of formula $R^1$—$NH_2$ under conditions exemplified below or other conditions known to those skilled in the art, affords intermediate I which can deprotected under acidic conditions such as TFA to give J. Cyclization of intermediate J under conditions described for Scheme 1 using phosgene equivalents affords the desired compounds of formula I.

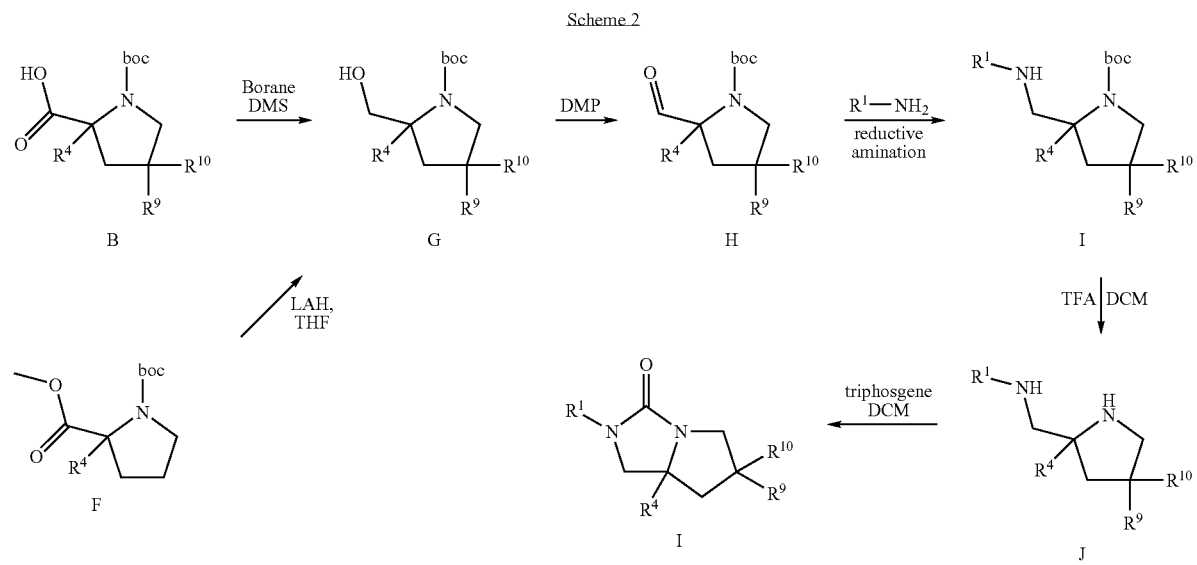

Compounds of formula I, where $R^1$ is a polycyclic ring substituted with a hydroxycarbonyl or aminocarbonyl, are prepared from the corresponding ester according to Scheme 3 via standard saponification (e.g. NaOH, MeOH) and amide forming methods under standard coupling conditions.

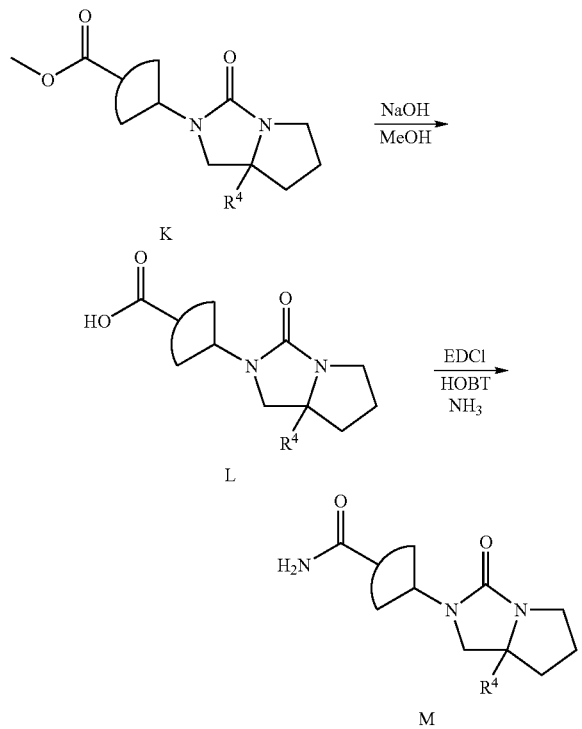

Compounds of formula I, where $R^4$ is aryl, heteroaryl or substituted aryl or substituted heteroaryl are prepared by the general scheme 4 starting with ester of formula N, which is either commercially available or known or accessible according to literature or known procedures. Bromination of compound N with NBS and AIBN in a suitable solvent affords intermediate O which is reacted with an appropriate aminoalcohol under potassium carbonate conditions to afford the alcohol intermediate P. Conversion of the alcohol to the corresponding chloride using thionylchloride gave intermediate Q which is protected as using $BOC_2O$ under basic conditions in DMF. Cyclization of intermediate R under basic phase transfer conditions afforded intermediate S, a key intermediate in this synthetic sequence. Reduction of the ester to the aldehyde can be achieved using the standard two step protocol using lithium aluminium hydride at low temperature followed by a Tempo/NaOCl oxidation, furnishing compound intermediate U. Reductive amination under standard conditions (refluxing in EtOH, followed by sodium borohydride reduction) with a suitably substituted amine of formula $R^1$—$NH_2$ afforded intermediate V, which was deprotected under TFA conditions to give intermediate W. Cyclization of intermediate W under the usual conditions using triphosgene or equivalents and bases such as triethylamine afforded compounds of formula I. If appropriate or desired, these compounds were separated into the E and Z isomers via column chromatography over silica gel, or separated into its enantiomers by chiral HPLC.

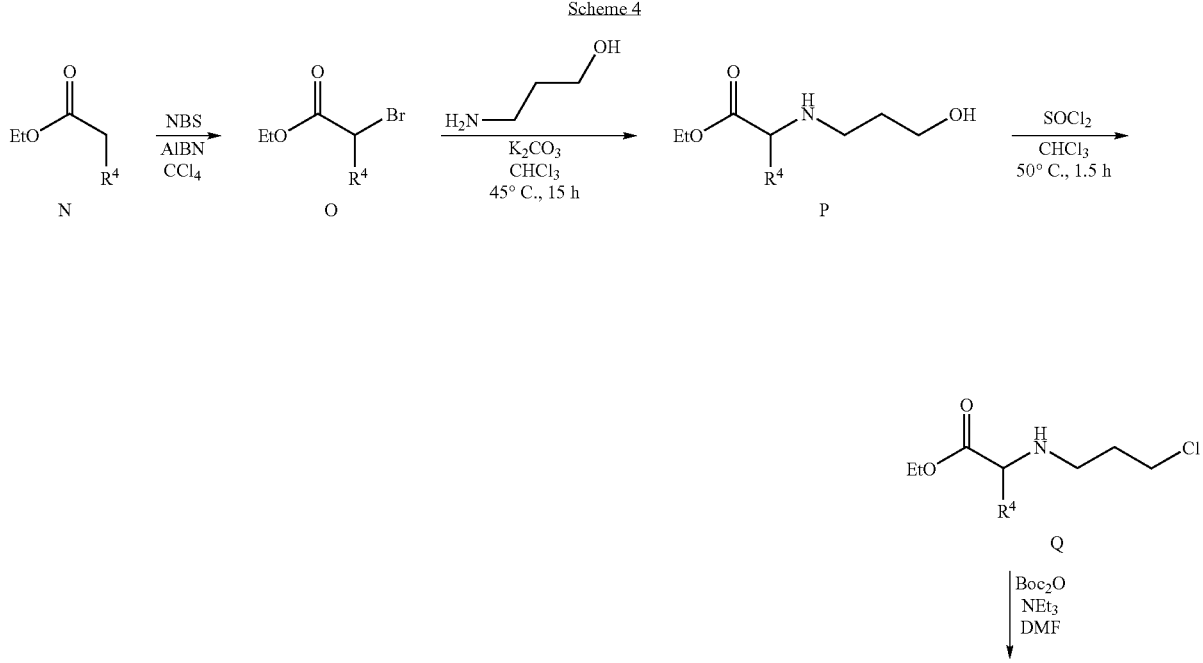

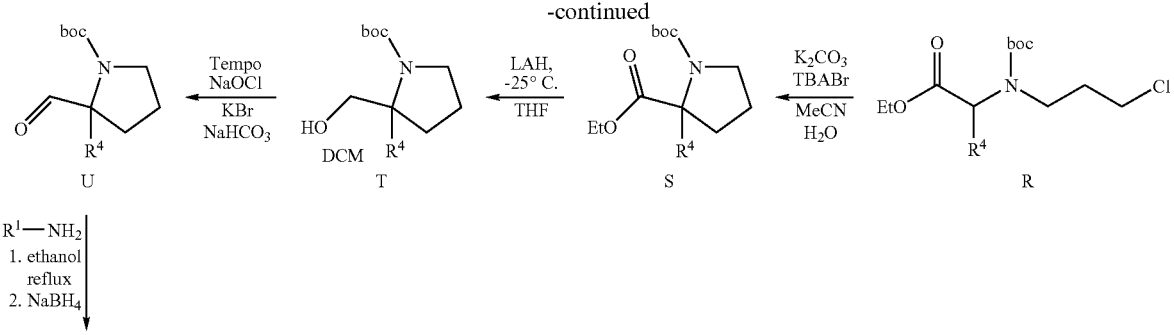

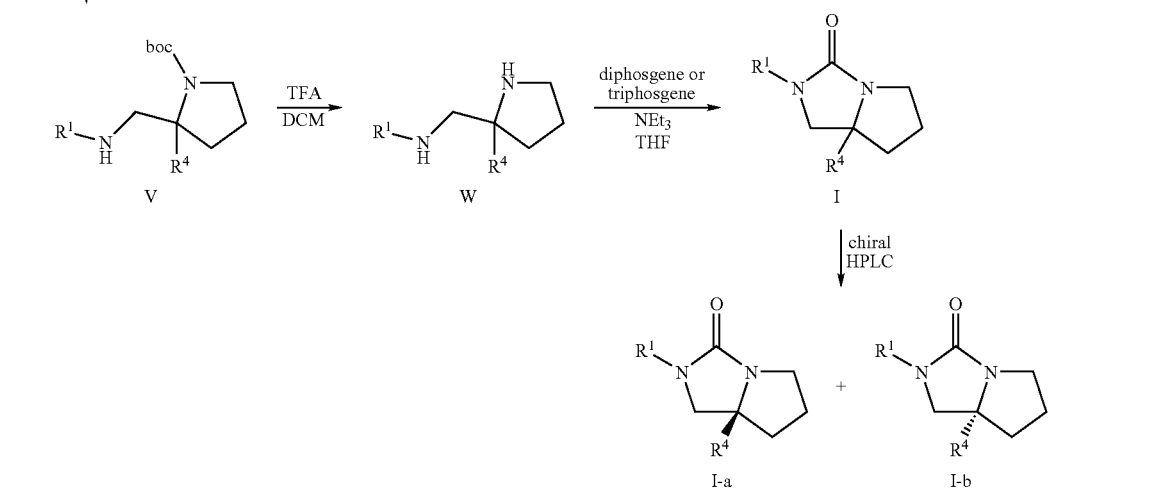

Particularly preferred is a process for the preparation of a compound of formula (I) comprising one of the following reactions:

(a) the reaction of a compound according to formula (Ia)

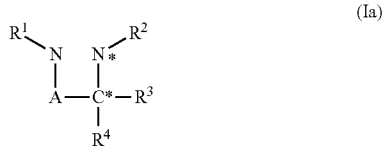

wherein A, $R^1$, $R^2$, $R^3$ and $R^4$ are as defined above, in the presence of phosgene; or (b) the reaction of a compound of formula (Ib)

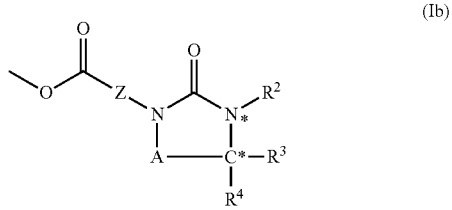

in the presence of a base, preferably an hydroxide, preferably sodium hydroxide, wherein A, $R^2$, $R^3$ and $R^4$ are as defined above, and wherein Z represents a bornane, norbornane, bicyclo[2.2.2]octane or adamantane.

optionally followed by the reaction of the resulting product in the presence of EDCI, HOBT and a base, preferably an amine, preferably triethylamine.

The compounds of formula I described above for use as therapeutically active substance are a further embodiment of the invention.

Also an embodiment of the present invention are compounds as described above for the preparation of medicaments for the prophylaxis and therapy of illnesses which are caused by disorders associated with the enzyme 11beta-hydroxysteroid dehydrogenase1 (11bHSD1).

Likewise an embodiment of the invention are pharmaceutical compositions comprising a compound of the formula I as described above and a therapeutically inert carrier.

A further preferred embodiment of the present invention is the use of a compound of formula I as described above for the preparation of medicaments for the treatment and prophylaxis of diabetes, obesity, eating disorders and dyslipidemiae.

A further preferred embodiment of the present invention are compounds of formula I for use as medicament for the treatment and prophylaxis of diabetes, obesity, eating disorders and dyslipidemiae.

Particularly preferred is the use of a compound according to formula I as described above for the preparation of medicaments for the treatment and prophylaxis of diabetes Type II.

Particularly preferred are compounds of formula I for use as medicament for the treatment and prophylaxis of diabetes Type II.

A further embodiment of the present invention comprises a compound according to formula I as described above, when manufactured according to any one of the described processes.

Also an embodiment of the invention is a method for the treatment and prophylaxis of diabetes, obesity, eating disorders and dyslipidemiae, which method comprises administering an effective amount of a compound of formula I as described above.

Particularly preferred is a method for the treatment and prophylaxis of diabetes Type II, which method comprises administering an effective amount of a compound according to formula I as described above.

ASSAY PROCEDURES

Transient expression and partial Purification:

The cDNA encoding the human 11beta-HSD1 protein was cloned into the expression vector pcDNA3 (Stratagene). This construct (for details see Alex Odermatt et al.; J Biol Chem., 1999, Vol. 274, Issue 40, 28762-28770) was used to transiently express the protein in HEK293 cells (ATCC number: CRL-1573, described in Graham, F. L., Smiley, J., Russell, W. C., Nairn, R.; (1977)) using lipofectamine. 48 h after transfection cells were washed twice with ice-cold PBS (Phosphate buffered Saline). To 1 volume of cell suspension in PBS 2 volumes of ice-cold lysis buffer (50 mM Tris; pH7.5; 1 mM EDTA; 100 mM NaCl) were added. The cells were lysed by Potter-homogenization (20 strokes). The resulting homogenate was sonicated with a tip sonicator (10% output; 2×30 sec.) and cleared by a low speed centrifugation (10 min×9000 g; 4° C.). The microsomal fraction was collected by a high speed centrifugation (60 min×110,000 g). The resulting pellet was resuspended in storage buffer (20 mM Tris pH 7.5; 1 mM EDTA; 10% Glycerol) and the centrifugation was repeated. The resulting pellet containing the microsomal fraction was again taken up into storage buffer and aliquots were kept frozen in liquid Nitrogen until use.

Generation of Stable Cell Lines Expressing 11beta-HSD1:

The same construct used for transient expression of human 11beta-HSD1 was also used to establish cell lines stably expressing the protein. Briefly, (HEK293) cells were transfected with 11beta-HSD1 construct using the lipofectamine reagent (Gibco BRL) according to the manufacturer's instruction. Two days after transfection, geneticin selection (0.8 mg/ml) was initiated and several stable clones were isolated. One clone was further used for pharmacological characterization.

Microsome Assay

Microsomes isolated from HEK293 cells transiently expressing human 11beta-HSD1 (for details see above) were incubated in assay buffer (100 mM NaCl; 1 mM EDTA; 1 mM EGTA; 1 mM MgCl; 250 mM Sucrose; 20 mM Tris pH 7.4; Cortisone 50-200 nM and NADPH 1 mM) together with different concentrations of test substances. After 60 min. of incubation at 37° C. the assay was stopped by heating to 80° C. (5 min.) and by addition of the inhibitor Carbenoxolone (1 uM). The amount of Cortisol produced in this assay was determined using a commercially available, ELISA-based Cortisol-detection kit (Distributed by Assay Design, Inc.). Inhibitors were characterized by there $IC_{50}$ values, e.g. the concentration at which the production of cortisol was 50% reduced.

In this test preferred compounds as described above have $IC_{50}$ values below 1000 nM; more preferred compounds have $IC_{50}$ values below 100 nM. Most preferred compounds have $IC_{50}$ values below 10 nM.

Cellular Assay

To measure the effect of inhibitors in intact cells HEK293 cells stably expressing human 11beta-HSD1 (see above) were cultivated in 96 well plates in DMEM. First inhibitors and 60 min later Cortisone was added to the cells. After 60 min of incubation at 37° C. in a 5% $CO_2$ atmosphere part of the medium was removed and the conversion from Cortisone to Cortisol was measured using a commercially available ELISA kit (Distributed by Assay Design, Inc.).

Results obtained in the microsome assay using representative compounds of the invention as the test compounds are shown in the following table:

Results obtained in the microsome assay using representative compounds of the invention as the test compounds are shown in the following table:

| Compound Example | h 11-beta-HSD 1 $IC_{50}$ (nM) |
|---|---|
| 1 | 0.074 |
| 2 | 0.004 |
| 3 | 0.93 |
| 4 | 0.072 |
| 5 | 6.113 |
| 6 | 0.193 |
| 7 | 0.017 |
| 8 | 0.116 |
| 9 | 1.26 |
| 10 | 0.117 |
| 11 | 1.113 |
| 12 | 0.001 |
| 13 | 0.084 |
| 14 | 0.03 |
| 15 | 0.495 |
| 16 | 0.037 |
| 17 | 0.017 |
| 18 | 0.001 |
| 19 | 1001 |
| 20 | 0.696 |
| 21 | 1001 |
| 22 | 0.525 |
| 23 | 1.01 |
| 24 | 0.026 |
| 25 | 0.069 |
| 26 | 0.003 |
| 27 | 0.001 |
| 28 | 0.008 |
| 29 | 0.001 |
| 30 | 0.762 |
| 31 | 0.079 |
| 32 | 0.708 |
| 33 | 0.01 |
| 34 | 0.002 |
| 35 | 0.001 |
| 36 | 0.02 |
| 37 | 0.024 |
| 38 | 1.126 |
| 39 | 0.237 |
| 40 | 0.015 |
| 41 | 0.002 |
| 42 | 0.001 |
| 43 | 0.001 |
| 44 | 0.001 |
| 45 | 0.005 |
| 46 | 0.001 |
| 47 | 0.003 |
| 48 | 0.005 |
| 49 | 0.02 |
| 50 | 1.149 |
| 51 | 1.016 |
| 52 | 0.068 |
| 53 | 0.096 |
| 54 | 1.185 |
| 55 | 0.287 |
| 56 | 0.009 |
| 57 | 0.088 |
| 58 | 0.002 |
| 59 | 0.175 |
| 60 | 1.575 |
| 61 | 1.754 |
| 62 | 0.001 |

-continued

| Compound Example | h 11-beta-HSD 1 IC$_{50}$ (nM) |
|---|---|
| 63 | 0.001 |
| 64 | 0.007 |
| 65 | 0.001 |
| 66 | 0.624 |
| 67 | 0.001 |
| 68 | 1.1 |
| 69 | 0.03 |
| 70 | 1.356 |
| 71 | 0.278 |
| 72 | 1.006 |
| 73 | 0.574 |
| 74 | 0.015 |
| 75 | 1001 |
| 76 | 0.188 |
| 77 | 0.387 |
| 78 | 0.593 |
| 79 | 0.168 |
| 80 | 0.09 |
| 81 | 0.621 |
| 82 | 0.615 |
| 83 | 0.004 |
| 84 | 0.002 |
| 85 | 0.001 |
| 86 | 0.001 |
| 87 | 0.001 |
| 88 | 0.001 |
| 89 | 0.015 |
| 90 | 0.094 |
| 91 | 0.007 |
| 92 | 0.059 |
| 93 | 0.001 |
| 94 | 0.008 |
| 95 | 0.007 |
| 96 | 0.124 |
| 97 | 0.004 |
| 98 | 0.003 |
| 99 | 0.111 |
| 100 | 0.001 |
| 101 | 0.001 |
| 102 | 0.068 |
| 103 | 0.001 |

Compounds as described above have IC$_{50}$ values below 1000 nM; preferred compounds have IC$_{50}$ values below 100 nM. More preferred compounds have IC$_{50}$ values below 10 nM. These results have been obtained by using the foregoing test.

The compounds of formula I and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically acceptable salts can be used for the prophylaxis and treatment of arthritis, cardiovascular diseases, diabetes, renal failure and particularly eating disorders and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Examples 1 and 2

(S)-2-((Z)-5-Hydroxy-adamantan-2-yl)-7a-methyl-hexahydro-pyrrolo[1,2-c]imidazol-3-one (1) and
(S)-2-((E)-5-Hydroxy-adamantan-2-yl)-7a-methyl-hexahydro-pyrrolo[1,2-c]imidazol-3-one (2)

Step A] (S)-2-((E/Z)-5-Hydroxy-adamantan-2-ylcarbamoyl)-2-methyl-pyrrolidine-1-carboxylic Acid Tert-butyl Ester To a solution of commercially available (S)-2-methyl-pyrrolidine-1,2-dicarboxylic acid 1-tert-butyl ester (146 mg, CAS: 103336-06-7) in DMF (10 mL) in a round bottom flask was added EDCI (122 mg), HOBT (86 mg), triethylamine (129 mg) followed by (E/Z)-4-amino-adamantan-1-ol (107 mg). The reaction was stirred at ambient temperature for 20 hours and was then diluted with water (20 mL) and EtOAc (30 mL). The mixture was separated and the aqueous phase was extracted with further EtOAc (2×). The combined organic phases were washed with saturated sodium bicarbonate solution (20 mL), water (20 mL), aqueous 1N HCl solution (20 mL) and brine (20 mL). The organic phase as dried over sodium sulfate and the volatiles were removed in vacuo to afford the desired compounds (S)-2-((E/Z)-5-hydroxy-adamantan-2-ylcarbamoyl)-2-methyl-pyrrolidine-1-carboxylic acid tert-butyl ester as a white crystalline solid (234 mg). This material was used in the subsequent reaction without further purification.

Step B] (S)-2-Methyl-pyrrolidine-2-carboxylic Acid ((E/Z)-5-hydroxy-adamantan-2-yl)-amide To a solution of (S)-2-((E/Z)-5-hydroxy-adamantan-2-ylcarbamoyl)-2-methyl-pyrrolidine-1-carboxylic acid tert-butyl ester (129 mg) in DCM (2 mL) was added trifluoroaceticacid (0.5 mL) at RT. The reaction was stirred for 2.5 hours and then reduced in vacuo. The residue was dissolved in chloroform (50 mL) and aqueous sodium bicarbonate solution was added (3 mL). Further solid sodium bicarbonate was added until pH=8. The chloroform phase was collected and the aqueous phase was washed with further chloroform (2×50 mL). The combined organic phases were dried over sodium sulfate, filtered and the chloroform was removed in vacuo to afford the desired (S)-2-methyl-pyrrolidine-2-carboxylic acid ((E/Z)-5-hydroxy-adamantan-2-yl)-amide as a white foam (95 mg). MS (EI): 279.4 (M$^+$). This material was used in the next step without further purification.

Step C] (E/Z)-4-[((S)-2-Methyl-pyrrolidin-2-ylmethyl)-amino]-adamantan-1-ol

To lithium aluminium hydride powder (53 mg) in THF (2 mL) was added dropwise at RT (S)-2-methyl-pyrrolidine-2-carboxylic acid ((E/Z)-5-hydroxy-adamantan-2-yl)-amide (174 mg) dissolved in THF (1 mL) and diethyl ether (0.5 mL). The reaction mixture was heated at 70° C. for 48 hours and was monitored by TLC. If needed, further lithium aluminium hydride was added to drive the reaction to completion. The reaction mixture was cooled in an ice bath and was quenched by careful addition of a saturated aqueous solution of sodium sulfate. To ensure efficient stirring further THF was added. Once quenched, further solid sodium sulfate was added and the slurry was filtered through a plug of sodium sulfate and washed through with further THF. The organic solvent was removed by rotary evaporation to afford (E/Z)-4-[((S)-2-Methyl-pyrrolidin-2-ylmethyl)-amino]-adamantan-1-ol (170 mg) as a brown gum. MS (EI): 265.4 (M$^+$). This material was used in the subsequent step without further purification.

Step D] (S)-2-((Z)-5-Hydroxy-adamantan-2-yl)-7a-methyl-hexahydro-pyrrolo[1,2-c]imidazol-3-one (1) and (S)-2-((E)-5-Hydroxy-adamantan-2-yl)-7a-methyl-hexahydro-pyrrolo[1,2-c]imidazol-3-one (2)

To a solution of (E/Z)-4-[((S)-2-methyl-pyrrolidin-2-ylmethyl)-amino]-adamantan-1-ol (93 mg) in DCM (1.5 mL) was added at 0° C. triphosgene (39 mg) in DCM (0.5 mL) followed by triethylamine (0.1 mL). The reaction mixture was then stirred at room temperature for 5 hours and monitored by TLC and MS. The reaction mixture was then diluted with water, the phases were separated and the aqueous phase was extracted with chloroform (4×25 mL). The combined organic phases were washed with 2N aqueous HCl (5 mL) and brine (5 mL) and dried over sodium sulfate. Filtration and evaporation in vacuo afforded a brown residue which was purified via flash column chromatography to afford (S)-2-((Z)-5-hydroxy-adamantan-2-yl)-7a-methyl-hexahydro-pyrrolo[1,2-c]imidazol-3-one (20 mg) and (S)-2-((E)-5-hydroxy-adamantan-2-yl)-7a-methyl-hexahydro-pyrrolo[1,2-c]imidazol-3-one (6 mg) as beige solids. MS (EI): 291.3 (M$^+$).

Examples 3 and 4

(S)-2-((Z)-5-Hydroxy-adamantan-2-yl)-hexahydro-pyrrolo[1,2-c]imidazol-3-one (3) and (S)-2-((E)-5-hydroxy-adamantan-2-yl)-hexahydro-pyrrolo[1,2-c]imidazol-3-one (4)

This material was obtained in analogy to example 1 and 2 (step A-D) using N-T-Boc-Proline (step A), to give (S)-2-((Z)-5-hydroxy-adamantan-2-yl)-hexahydro-pyrrolo[1,2-c]imidazol-3-one (12 mg, MS (ES+): 277.3 (MH$^+$), beige solid) and (S)-2-((E)-5-hydroxy-adamantan-2-yl)-hexahydro-pyrrolo[1,2-c]imidazol-3-one (9 mg, MS (ES+): 277.3 (MH$^+$), beige solid).

Example 5

(S)-2-Phenyl-hexahydro-pyrrolo[1,2-c]imidazol-3-one

This material was obtained in analogy to example 1 and 2 (step D) using commercially available (S)-(+)-2-(aminomethyl)pyrrolidine (150 mg), to give after flash column chromatography purification over silica gel (eluent EtOAc:Heptane) the desired (S)-2-Phenyl-hexahydro-pyrrolo[1,2-c]imidazol-3-one (87 mg, MS (ES+): 203.4 (MH$^+$)) as a white solid.

Examples 6 and 7

(S)-2-((Z)-5-Hydroxy-adamantan-2-yl)-hexahydro-imidazo[1,5-a]pyridin-3-one (6) and (S)-2-((E)-5-Hydroxy-adamantan-2-yl)-hexahydro-imidazo[1,5-a]pyridin-3-one (7)

This material was obtained in analogy to example 1 and 2 (step A-D) using commercially available BOC-L-pipecolic acid (step A), to give (S)-2-((Z)-5-hydroxy-adamantan-2-yl)-hexahydro-imidazo[1,5-a]pyridin-3-one (70 mg, MS (ES+): 291.3 (MH$^+$), white solid) and (S)-2-((E)-5-Hydroxy-adamantan-2-yl)-hexahydro-imidazo[1,5-a]pyridin-3-one (31 mg, MS (ES+): 291.3 (MH$^+$), white solid).

Example 8

(rac)-(E/Z)-4-(3-Oxo-tetrahydro-pyrrolo[1,2-c]imidazol-2-yl)-adamantane-1-carboxylic Acid Methyl Ester Step A] (rac)-2-[((E/Z)-5-Methoxycarbonyl-adamantan-2-ylamino)-methyl]-pyrrolidine-1-carboxylic Acid Tert-butyl Ester A solution of 4-oxo-adamantane-1-carboxylic acid methyl ester (200 mg, known compound, CAS: 56674-88-5) and 2-(aminomethyl)-1B-BOC-pyrrolidin (250 mg) in ethanol was heated to reflux for 2 hours. The solution was then cooled to 0° C. and NaBH$_4$ (47 mg) was added in portions. The white suspension was stirred overnight at ambient temperature. The solvent was then evaporated in vacuo and the residue was taken up in water and chloroform. The phases were separated and the aqueous phase was extracted with further chloroform (3×25 mL). The combined organics were washed with saturated aqueous NaHCO$_3$ solution, and dried over sodium sulfate. Filtration and evaporation of the volatiles in vacuo afforded a crude residue which was purified over silica gel flash column chromatography (EtOAc, 0-30% MeOH) to afford the desired 2-[((E/Z)-5-methoxycarbonyl-adamantan-2-ylamino)-methyl]-pyrrolidine-1-carboxylic acid tert-butyl ester as a colourless gum (300 mg, MS (ES+): 393.2 (MH$^+$).)

Step B] (E/Z)-4-[(Pyrrolidin-2-ylmethyl)-amino]-adamantane-1-carboxylic Acid Ethyl Ester To a solution of 2-[((E/Z)-5-methoxycarbonyl-adamantan-2-ylamino)-methyl]-pyrrolidine-1-carboxylic acid tert-butyl ester (300 mg) in DCM (2 mL) was added trifluoroacetic acid (TFA) (0.75 mL). The reaction was stirred for 4 hours and subsequently all volatiles were reduced in vacuo. The residue was taken up in chloroform (20 mL) and neutralized with approximately 2 mL of aqueous saturated NaHCO$_3$ solution until pH8. The phases were separated and the aqueous phase treated with solid NaCl and was extracted with further chloroform (20 mL). The combined organic layers were dried over sodium sulfate, filtered and reduced to obtain the crude desired (E/Z)-4-[(pyrrolidin-2-ylmethyl)-amino]-adamantane-1-carboxylic acid ethyl ester (214 mg, light brown gum) which was used in the subsequent step without further purification. MS (ES+): 293.3 (MH$^+$).)

Step C] (E/Z)-4-(3-Oxo-tetrahydro-pyrrolo[1,2-c]imidazol-2-yl)-adamantane-1-carboxylic Acid Methyl Ester This material was obtained in analogy to example 1 and 2 (step D) using (E/Z)-4-[(pyrrolidin-2-ylmethyl)-amino]-adamantane-1-carboxylic acid ethyl ester (214 mg), to give the desired (E/Z)-4-(3-oxo-tetrahydro-pyrrolo[1,2-c]imidazol-2-yl)-adamantane-1-carboxylic acid methyl ester as a 1:1 E/Z mixture (68 mg, MS (ES+): 319.3 (MH$^+$), beige solid).

Examples 9 and 10

(S)-2-((Z)-5-Hydroxy-adamantan-2-yl)-1,5,10,10a-tetrahydro-2H-imidazo[1,5-b]isoquinolin-3-one (9) and (S)-2-((E)-5-Hydroxy-adamantan-2-yl)-1,5,10,10a-tetrahydro-2H-imidazo[1,5-b]isoquinolin-3-one (10)

These materials were obtained in analogy to example 1 and 2 (step A-D) using commercially available BOC-TIC-OH (0.5 g) (step A), to give after silica gel separation in step D the desired (S)-2-((Z)-5-hydroxy-adamantan-2-yl)-1,5,10,10a-tetrahydro-2H-imidazo[1,5-b]isoquinolin-3-one (26 mg, MS (ES+): 339.3 (MH$^+$), off-white solid) and (S)-2-((E)-5-hydroxy-adamantan-2-yl)-1,5,10,10a-tetrahydro-2H-imidazo[1,5-b]isoquinolin-3-one (26 mg, MS (ES+): 339.3 (MH$^+$), off-white solid).

Example 11

(rac)-(E/Z)-4-(3-Oxo-tetrahydro-pyrrolo[1,2-c]imidazol-2-yl)-adamantane-1-carboxylic Acid To a solution of (E/Z)-4-(3-Oxo-tetrahydro-pyrrolo[1,2-c]imidazol-2-yl)-adamantane-1-carboxylic acid methyl ester (30 mg, see example 8) in MeOH (0.5 mL) was added NaOH (90 µL of a 1N aqueous solution). The reaction mixture was stirred overnight and was then poured onto ice/2N aqueous HCl. The aqueous phase was extracted with EtOAc (2×) and the combined organic phases were washed with brine and dried over sodium sulfate. Filtration and evaporation of the volatiles in vacuo afforded pure desired (rac)-(E/Z)-4-(3-oxo-tetrahydro-pyrrolo[1,2-c]imidazol-2-yl)-adamantane-1-carboxylic acid (25 mg, MS (ES-): 303.3 (M-H), off-white solid).

Example 12

(rac)-7a-Benzyloxymethyl-2-((E/Z)-5-hydroxy-adamantan-2-yl)-hexahydro-pyrrolo[1,2-c]imidazol-3-one

Step A] (rac)-2-Benzyloxymethyl-pyrrolidine-1,2-dicarboxylic acid 1-tert-butyl Ester To a solution of LDA (58 mL of a 2M solution in THF/Heptane) in THF (60 mL) at 0° C. was added BOC-L-proline (10 g as a solution in 25 mL of THF) dropwise via syringe over 10 minutes. The reaction mixture was stirred a further 20 minutes and then benzylchloromethylether (8.73 g) was added in one portion via syringe. The reaction mixture was allowed to warm to RT and stirred for 20 hours. The reaction was quenched with 1N aqueous HCl solution (30 mL) and diluted with EtOAc (80 mL). The phases were separated and the aqueous phase was extracted with further EtOAc (2×80 mL). The combined organics were washed with brine and dried over sodium sulfate. Filtration and evacuation of the volatiles in vacuo afforded a crude residue which was purified by flash column chromatography over silica gel (Heptane/EtOAc) to afford the desired 2-benzyloxymethyl-pyrrolidine-1,2-dicarboxylic acid 1-tert-butyl ester (810 mg, MS (ES-): 334.4 (M-H), orange oil).

Step B] (rac)-2-Benzyloxymethyl-2-((E/Z)-5-hydroxy-adamantan-2-ylcarbamoyl)-pyrrolidine-1-carboxylic Acid Tert-butyl Ester This material was obtained in analogy to example 1 and 2, step A, using 2-benzyloxymethyl-pyrrolidine-1,2-dicarboxylic acid 1-tert-butyl ester, to give the desired (rac)-2-benzyloxymethyl-2-((E/Z)-5-hydroxy-adamantan-2-ylcarbamoyl)-pyrrolidine-1-carboxylic acid tert-butyl ester (10.4 g, MS (ES+): 485.3 (M+H)) as a brown oil.

Step C] (rac)-2-Benzyloxymethyl-pyrrolidine-2-carboxylic acid ((E/Z)-5-hydroxy-adamantan-2-yl)-amide This material was obtained in analogy to example 1 and 2, step B, using 2-benzyloxymethyl-2-((E/Z)-5-hydroxy-adamantan-2-ylcarbamoyl)-pyrrolidine-1-carboxylic acid tert-butyl ester (5 g), to give the desired (rac)-2-benzyloxymethyl-pyrrolidine-2-carboxylic acid ((E/Z)-5-hydroxy-adamantan-2-yl)-amide (3.8 g, MS (ES+): 385.4 (M+H)) as a brown oil.

Step D] (rac)-(E/Z)-4-[(2-Benzyloxymethyl-pyrrolidin-2-ylmethyl)-amino]-adamantan-1-ol This material was obtained in analogy to example 1 and 2, step C, using (rac)-2-benzyloxymethyl-pyrrolidine-2-carboxylic acid ((E/Z)-5-hydroxy-adamantan-2-yl)-amide (3.8 g), to give the desired (rac)-(E/Z)-4-[(2-benzyloxymethyl-pyrrolidin-2-ylmethyl)-amino]-adamantan-1-ol (2.75 g, MS (ES+): 371.4 (M+H)) as a yellow oil.

Step E] (rac)-7a-Benzyloxymethyl-2-((E/Z)-5-hydroxy-adamantan-2-yl)-hexahydro-pyrrolo[1,2-c]imidazol-3-one This material was obtained in analogy to example 1 and 2, step D, using (rac)-(E/Z)-4-[(2-benzyloxymethyl-pyrrolidin-2-ylmethyl)-amino]-adamantan-1-ol (2.750 g), to give (rac)-7a-benzyloxymethyl-2-((E/Z)-5-hydroxy-adamantan-2-yl)-hexahydro-pyrrolo[1,2-c]imidazol-3-one (1.4 g, MS (ES+): 397.4 (M+H)) as a white solid. Optionally the E/Z mixture was separated using flash column chromatography to give (rac)-7a-benzyloxymethyl-2-((Z)-5-hydroxy-adamantan-2-yl)-hexahydro-pyrrolo[1,2-c]imidazol-3-one (0.75 g, MS (ES+): 397.4 (M+H), white solid) and (rac)-7a-benzyloxymethyl-2-((E)-5-hydroxy-adamantan-2-yl)-hexahydro-pyrrolo[1,2-c]imidazol-3-one (0.454 g, MS (ES+): 397.4 (M+H), white solid).

Examples 13 and 14

(R)-7a-Benzyl-2-((Z)-5-hydroxy-adamantan-2-yl)-hexahydro-pyrrolo[1,2-c]imidazol-3-one (13) and (R)-7a-benzyl-2-((E)-5-hydroxy-adamantan-2-yl)-hexahydro-pyrrolo[1,2-c]imidazol-3-one (14)

These materials were obtained in analogy to example 1 and 2 (step A-D) using commercially available BOC-(S)-alpha-benzyl-proline (0.5 g) (step A), to give after silica gel separation in step D the desired (R)-7a-benzyl-2-((Z)-5-hydroxy-adamantan-2-yl)-hexahydro-pyrrolo[1,2-c]imidazol-3-one (31 mg, MS (ES+): 367.3 (MH$^+$), white solid) and (R)-7a-benzyl-2-((E)-5-hydroxy-adamantan-2-yl)-hexahydro-pyrrolo[1,2-c]imidazol-3-one (17 mg, MS (ES+): 367.3 (MH$^+$), white solid).

Example 15

(R)-7a-Benzyl-2-((E/Z)-5-hydroxy-adamantan-2-yl)-tetrahydro-pyrrolo[1,2-c]imidazole-1,3-dione This material was obtained during the synthesis of examples 13 and 14, due to incomplete reduction in step C (lithium aluminium hydride reduction) which upon cyclisation in step D affords (R)-7a-benzyl-2-((E/Z)-5-hydroxy-adamantan-2-yl)-tetrahydro-pyrrolo[1,2-c]imidazole-1,3-dione (9 mg, MS (ES+): 381.3 (MH$^+$), white solid).

Example 16

(E)-4-((S)-3-Oxo-tetrahydro-pyrrolo[1,2-c]imidazol-2-yl)-adamantane-1-carboxylic Acid Amide To a solution of (E/Z)-4-(3-oxo-tetrahydro-pyrrolo[1,2-c]imidazol-2-yl)-adamantane-1-carboxylic acid (25 mg, example 11) in DCM (1 mL) was added at 0° C. EDCI (16 mg), HOBT (11 mg) and Hünig's base (28 µL). The solution was stirred for 30 minutes and then NH$_3$ in MeOH (12 µL of a 7 M solution) was added. The reaction was stirred for 3 hours at room temperature and then quenched with ice and aqueous sodium bicarbonate solution. The phases were separated and the aqueous phase was extracted with EtOAc (2×). The combined organics were washed with 0.5 N HCl, brine and dried over sodium sulphate. Filtration and evaporation in vacuo afforded a crude residue which was purified via flash column chromatography on silica gel (eluent: DCM/MeOH 95/5) to afford the desired (E)-4-((S)-3-oxo-tetrahydro-pyrrolo[1,2-c]imidazol-2-yl)-adamantane-1-carboxylic acid amide (3.5 mg, MS (ES+): 304.3 (MH$^+$), white solid). The Z isomer was not isolated off the column in this case.

Example 17

(rac)-2-((E/Z)-5-Hydroxy-adamantan-2-yl)-7a-hydroxymethyl-hexahydro-pyrrolo[1,2-c]imidazol-3-one To a solution of (rac)-7a-benzyloxymethyl-2-((E/Z)-5-hydroxy-adamantan-2-yl)-hexahydro-pyrrolo[1,2-c]imidazol-3-one (150 mg, example 12) in EtOAc (3 mL) was added 10% Pd/C catalyst and the reaction mixture was flushed with hydrogen gas using a hydrogen gas filled balloon and a vacuum manifold and maintained under a hydrogen atmosphere. After 1 hour the reaction mixture was filtered through Celite® and washed through with further EtOAc. Evaporation of the solvent afforded the desired (rac)-2-((E/Z)-5-hydroxy-adamantan-2-yl)-7a-hydroxymethyl-hexahydro-pyrrolo[1,2-c]imidazol-3-one which was not further purified (13 mg, MS (ES+): 307.3 (MH$^+$), colourless gum).

Example 18

(rac)-6-[2-((E/Z)-5-Hydroxy-adamantan-2-yl)-3-oxo-tetrahydro-pyrrolo[1,2-c]imidazol-7a-yl-methoxy]-nicotinonitrile To a solution of (rac)-2-((E/Z)-5-hydroxy-adamantan-2-yl)-7a-hydroxymethyl-hexahydro-pyrrolo[1,2-c]imidazol-3-one (7 mg) in THF (1 mL) was added at 0° C. NaHMDS (24 µL of a 1 M solution in THF) dropwise via syringe. The mixture went turbid and was stirred for 5 minutes at this temperature and then 6-chloronicotinonitrile (3 mg) dissolved in THF (0.5 mL) was added to the reaction mixture, dropwise over 2 minutes via syringe. The reaction was allowed to warm up to RT and left to stir overnight. The reaction was quenched by adding saturated aqueous sodium bicarbonate solution and diluted with EtOAc. The phases were separated and the aqueous phase was extracted further with EtOAc. The combined organics were washed with 1N aq. HCl solution, brine and dried with sodium sulfate. Filtration and removal of the volatiles in vacuo afforded a crude gum. Flash column chromatography over silica gel of this residue (eluting with 100% EtOAc to 3% MeOH in EtOAc) afforded the desired (rac)-6-[2-((E/Z)-5-hydroxy-adamantan-2-yl)-3-oxo-tetrahydro-pyrrolo[1,2-c]imidazol-7a-yl-methoxy]-nicotinonitrile (8 mg, MS (ES+): 409.4 (MH$^+$)) as a white solid.

Examples 19 and 20

(S)-2-((Z)-5-Hydroxy-adamantan-2-yl)-1,2,9,9a-tetrahydro-imidazo[1,5-a]indol-3-one (19) and (S)-2-((E)-5-hydroxy-adamantan-2-yl)-1,2,9,9a-tetrahydro-imidazo[1,5-a]indol-3-one (20)

These materials were obtained in analogy to example 1 (step A-D) using BOC-L-indoline-2-carboxylic acid (1 g) (step A), to give after silica gel separation in step D the desired (S)-2-((Z)-5-hydroxy-adamantan-2-yl)-1,2,9,9a-tetrahydro-imidazo[1,5-a]indol-3-one (100 mg, MS (ES+): 325.3 (MH$^+$), white solid) and (S)-2-((E)-5-hydroxy-adamantan-2-yl)-1,2,9,9a-tetrahydro-imidazo[1,5-a]indol-3-one (46 mg, MS (ES+): 325.3 (MH$^+$), white solid).

Examples 21 and 22

(R)-2-((Z)-5-Hydroxy-adamantan-2-yl)-hexahydro-pyrrolo[1,2-c]imidazol-3-one (21) and (R)-2-((E)-5-Hydroxy-adamantan-2-yl)-hexahydro-pyrrolo[1,2-c]imidazol-3-one (22)

These materials were obtained in analogy to example 1 (step A-D) using commercially available BOC-D-PRO-OH (0.6 g) (step A), to give after silica gel separation in step D the desired (R)-2-((Z)-5-hydroxy-adamantan-2-yl)-hexahydro-pyrrolo[1,2-c]imidazol-3-one (125 mg, MS (ES+): 277.2 (MH$^+$), white solid) and (R)-2-((E)-5-hydroxy-adamantan-2-yl)-hexahydro-pyrrolo[1,2-c]imidazol-3-one (74 mg, MS (ES+): 277.2 (MH$^+$), white solid).

Example 23

(rac)-2-((E/Z)-5-Hydroxy-adamantan-2-yl)-hexahydro-imidazo[5,1-c][1,4]oxazin-3-one This material was obtained in analogy to example 1 (step A-D) using commercially available 4-N—BOC-3-morpholinecarboxylic acid (0.6 g) (step A), to give after silica gel separation in step D the desired (rac)-2-((E/Z)-5-Hydroxy-adamantan-2-yl)-hexahydro-imidazo[5,1-c][1,4]oxazin-3-one (195 mg, MS (ES+): 293.1 (MH$^+$), white solid).

Example 24

(rac)-2-((E)-5-Hydroxy-adamantan-2-yl)-7a-hydroxymethyl-hexahydro-pyrrolo[1,2-c]imidazol-3-one This material was obtained by separating the E and Z isomers of 2-((E/Z)-5-hydroxy-adamantan-2-yl)-7a-hydroxymethyl-hexahydro-pyrrolo[1,2-c]imidazol-3-one (example 17) over flash column chromatography over silica gel (eluent 100% EtOAc to 5% MeOH in EtOAc) to give the desired (rac)-2-((E)-5-hydroxy-adamantan-2-yl)-7a-hydroxymethyl-hexahydro-pyrrolo[1,2-c]imidazol-3-one (MS (ES+): 307.3 (MH$^+$), white solid.

Examples 25 and 26

(rac)-2-((Z)-5-Hydroxy-adamantan-2-yl)-8a-methyl-hexahydro-imidazo[1,5-a]pyridin-3-one and (rac)-2-((E)-5-Hydroxy-adamantan-2-yl)-8a-methyl-hexahydro-imidazo[1,5-a]pyridin-3-one These materials were obtained in analogy to example 1 (step A-D) using 2-methyl-piperidine-1,2-dicarboxylic acid 1-tert-butyl ester (see example 1, step A) (0.6 g, for preparation see below), to give after silica gel separation in step D the desired (rac)-2-((Z)-5-hydroxy-adamantan-2-yl)-8a-methyl-hexahydro-imidazo[1,5-a]pyridin-3-one (230 mg, MS (ES+): 305.3 (MH$^+$), white solid) and (rac)-2-((E)-5-hydroxy-adamantan-2-yl)-8a-methyl-hexahydro-imidazo[1,5-a]pyridin-3-one (118 mg, MS (ES+): 305.3 (MH$^+$), white solid).

Starting Material for Step A]
2-Methyl-piperidine-1,2-dicarboxylic Acid 1-tert-butyl Ester To a solution of LDA (9.6 mL of a 2M solution in THF/Heptane) in THF (15 mL) at 0° C. was added 1-(tert-butoxycarbonyl)-2-piperidinecarboxylic acid (2 g as a suspension in 4 mL of THF) dropwise via syringe over 10 minutes. The reaction mixture was stirred a further 20 minutes and then MeI (1.238 g) was added in one portion via syringe. The reaction mixture was allowed to warm to RT and stirred for 72 hours. The reaction was quenched with 2N aqueous HCl solution and diluted with EtOAc. The phases were separated and the aqueous phase was extracted with further EtOAc. The combined organics were washed with brine and dried over sodium sulfate. Filtration and evacuation of the volatiles in vacuo afforded a crude residue which was purified by flash column chromatography over silica gel (Heptane/EtOAc) to afford the desired (rac)-2-methyl-piperidine-1,2-dicarboxylic acid 1-tert-butyl ester (810 mg, MS (ES−): 242.4 (M−H), brown crystals).

Example 27

6-[(rac)-2-((E)-5-Hydroxy-adamantan-2-yl)-3-oxo-tetrahydro-pyrrolo[1,2-c]imidazol-7a-ylmethoxy]-nicotinonitrile This material was obtained in analogy to example 18 using (rac)-2-((E)-5-hydroxy-adamantan-2-yl)-7a-hydroxymethyl-hexahydro-pyrrolo[1,2-c]imidazol-3-one (example 24) (42 mg), to give after chromatography over silica gel the desired (6-[(rac)-2-((E)-5-hydroxy-adamantan-2-yl)-3-oxo-tetrahydro-pyrrolo[1,2-c]imidazol-7a-ylmethoxy]-nicotinonitrile (34 mg, MS (ES+): 409.4 (MH$^+$), off-white solid).

Examples 28 and 29

(rac)-2-((Z)-5-Hydroxy-adamantan-2-yl)-7a-(5-trifluoromethyl-pyridin-2-yloxymethyl)-hexahydro-pyrrolo[1,2-c]imidazol-3-one (28) and (rac)-2-((E)-5-Hydroxy-adamantan-2-yl)-7a-(5-trifluoromethyl-pyridin-2-yloxymethyl)-hexahydro-pyrrolo[1,2-c]imidazol-3-one (29)

These materials were obtained in analogy to example 18 using (rac)-2-((E/Z)-5-hydroxy-adamantan-2-yl)-7a-hydroxymethyl-hexahydro-pyrrolo[1,2-c]imidazol-3-one (example 17) (100 mg) and 2-chloro-5-(trifluoromethyl)pyridine, to give after chromatography over silica gel (eluent: EtOAc) the desired (rac)-2-((Z)-5-hydroxy-adamantan-2-yl)-7a-(5-trifluoromethyl-pyridin-2-yloxymethyl)-hexahydro-pyrrolo[1,2-c]imidazol-3-one (52 mg, MS (ES+): 452.1 (MH$^+$), white solid) and (rac)-2-((E)-5-hydroxy-adamantan-2-yl)-7a-(5-trifluoromethyl-pyridin-2-yloxymethyl)-hexahydro-pyrrolo[1,2-c]imidazol-3-one (50 mg, MS (ES+): 452.1 (MH$^+$), white solid).

Examples 30 and 31

(6R,7aS)-6-Benzyloxy-2-((Z)-5-hydroxy-adamantan-2-yl)-hexahydro-pyrrolo[1,2-c]imidazol-3-one (30) and (6R,7aS)-6-benzyloxy-2-((E)-5-hydroxy-adamantan-2-yl)-hexahydro-pyrrolo[1,2-c]imidazol-3-one (31)

These materials were obtained in analogy to example 1 and 2 (step A-D) using commercially available BOC-Hyp (BZL)-OH (step A) (2 g), to give after silica gel separation in step D the desired (6R,7aS)-6-Benzyloxy-2-((Z)-5-hydroxy-adamantan-2-yl)-hexahydro-pyrrolo[1,2-c]imidazol-3-one (137 mg, MS (ES+): 383.3 (MH$^+$), white solid) and (6R,7aS)-6-benzyloxy-2-((E)-5-hydroxy-adamantan-2-yl)-hexahydro-pyrrolo[1,2-c]imidazol-3-one (206 mg, MS (ES+): 383.3 (MH$^+$), white solid).

Example 32

(6R,7aS)-6-Hydroxy-2-((E)-5-hydroxy-adamantan-2-yl)-hexahydro-pyrrolo[1,2-c]imidazol-3-one To a solution of (6R,7aS)-6-benzyloxy-2-((E)-5-hydroxy-adamantan-2-yl)-hexahydro-pyrrolo[1,2-c]imidazol-3-one (150 mg, example 31) in EtOAc (3 mL) and MeOH (4 drops) was added 10% Pd/C catalyst and the reaction mixture was flushed with hydrogen gas using a balloon and vacuum manifold and maintained under a hydrogen atmosphere. After 1.2 hours the reaction mixture was filtered through Celite® and washed through with further EtOAc. Evaporation of the solvent afforded desired (6R,7aS)-6-hydroxy-2-((E)-5-hydroxy-adamantan-2-yl)-hexahydro-pyrrolo[1,2-c]imidazol-3-one which was not further purified (62 mg, MS (ES+): 293.1 (MH$^+$), white solid).

Example 33

(rac)-2-((E/Z)-5-Hydroxy-adamantan-2-yl)-7a-methoxymethyl-hexahydro-pyrrolo[1,2-c]imidazol-3-one This material was obtained in analogy to example 18 using (rac)-2-((E/Z)-5-hydroxy-adamantan-2-yl)-7a-hydroxymethyl-hexahydro-pyrrolo[1,2-c]imidazol-3-one (example 17) (81 mg) and methyliodide (38 mg), to give after chromatography over silica gel the desired (rac)-2-((E/Z)-5-Hydroxy-adamantan-2-yl)-7a-methoxymethyl-hexahydro-pyrrolo[1,2-c]imidazol-3-one as a 1:1 mixture of isomers (15 mg, MS (ES+): 321.3 (MH$^+$), beige solid).

Example 34

(rac)-7a-(2,4-Difluoro-benzyloxymethyl)-2-((E)-5-hydroxy-adamantan-2-yl)-hexahydro-pyrrolo[1,2-c]imidazol-3-one This material was obtained in analogy to example 18 using (rac)-2-((E)-5-hydroxy-adamantan-2-yl)-7a-hydroxymethyl-hexahydro-pyrrolo[1,2-c]imidazol-3-one (example 24) (58 mg) and 2,4-difluorobenzylbromide (39 mg), to give after chromatography over silica gel the desired (rac)-7a-(2,4-difluoro-benzyloxymethyl)-2-((E)-5-hydroxy-adamantan-2-yl)-hexahydro-pyrrolo[1,2-c]imidazol-3-one (55 mg, MS (ES+): 433.3 (MH$^+$)) as a white solid.

Examples 35 and 36

(S)-2-((E)-5-Hydroxy-adamantan-2-yl)-8a-methyl-hexahydro-imidazo[1,5-a]pyridin-3-one (35) and (R)-2-((E)-5-Hydroxy-adamantan-2-yl)-8a-methyl-hexahydro-imidazo[1,5-a]pyridin-3-one (36)

(rac)-2-((E)-5-Hydroxy-adamantan-2-yl)-8a-methyl-hexahydro-imidazo[1,5-a]pyridin-3-one (104 mg, example 26) was separated using chiral HPLC on Chiralpak AD, using 19% isopropanol/heptane as eluent and UV detection (220 nm) to give (S)-2-((E)-5-Hydroxy-adamantan-2-yl)-8a-methyl-hexahydro-imidazo[1,5-a]pyridin-3-one (38 mg, (+) enantiomer, MS (ES+): 305.4 (MH$^+$), white solid) and (R)-2-((E)-5-Hydroxy-adamantan-2-yl)-8a-methyl-hexahydro-imidazo[1,5-a]pyridin-3-one (36 mg, (−) enantiomer, MS (ES+): 305.4 (MH$^+$), white solid).

Examples 37 and 38

(S)-2-((E)-5-Hydroxy-adamantan-2-yl)-7a-hydroxymethyl-hexahydro-pyrrolo[1,2-c]imidazol-3-one (37) and (R)-2-((E)-5-Hydroxy-adamantan-2-yl)-7a-hydroxymethyl-hexahydro-pyrrolo[1,2-c]imidazol-3-one (38)

(rac)-2-((E)-5-Hydroxy-adamantan-2-yl)-7a-hydroxymethyl-hexahydro-pyrrolo[1,2-c]imidazol-3-one (180 mg, example 24) was separated using chiral HPLC on Chiralpak AD, using 10% isopropanol/heptane as eluent and UV detection (220 nm) to give (S)-2-((E)-5-hydroxy-adamantan-2-yl)-7a-hydroxymethyl-hexahydro-pyrrolo[1,2-c]imidazol-3-one (53 mg, (+) enantiomer, MS (ES+): 307.3 (MH$^+$), white solid) and (R)-2-((E)-5-hydroxy-adamantan-2-yl)-7α-hydroxymethyl-hexahydro-pyrrolo[1,2-c]imidazol-3-one (99 mg, (−) enantiomer, MS (ES+): 307.3 (MH$^+$), white solid).

Examples 39 and 40

(rac)-2-((Z)-5-Hydroxy-adamantan-2-yl)-1,2,5,9b-tetrahydro-imidazo[5,1-a]isoindol-3-one (39) and (rac)-2-((E)-5-Hydroxy-adamantan-2-yl)-1,2,5,9b-tetrahydro-imidazo[5,1-a]isoindol-3-one (40)

This material was obtained in analogy to example 1 (step A-D) using (R,S)-Boc-1,3-dihydro-2H-isoindole carboxylic acid (0.6 g, step A), to give (rac)-2-((Z)-5-hydroxy-adamantan-2-yl)-1,2,5,9b-tetrahydro-imidazo[5,1-a]isoindol-3-one (72 mg, MS (ES+): 325.2 (MH$^+$), beige solid) and (rac)-2-((E)-5-Hydroxy-adamantan-2-yl)-1,2,5,9b-tetrahydro-imidazo[5,1-a]isoindol-3-one (40 mg, MS (ES+): 325.2 (MH$^+$), beige solid).

Examples 41 and 42

(rac)-2-((Z)-5-Hydroxy-adamantan-2-yl)-7a-phenyl-hexahydro-pyrrolo[1,2-c]imidazol-3-one (41) and (rac)-2-((E)-5-Hydroxy-adamantan-2-yl)-7a-phenyl-hexahydro-pyrrolo[1,2-c]imidazol-3-one (42)

These materials were obtained in analogy to example 86 (step A-J) using phenyl-acetic acid ethyl ester (step A), and the known (E/Z)-4-amino-adamantan-1-ol (CAS: 75375-89-2) (step H) to give after step I the desired (rac)-2-((Z)-5-hydroxy-adamantan-2-yl)-7a-phenyl-hexahydro-pyrrolo[1,2-c]imidazol-3-one (37 mg, MS (ES+): 353.3 (MH$^+$), white solid) and (rac)-2-((E)-5-Hydroxy-adamantan-2-yl)-7a-phenyl-hexahydro-pyrrolo[1,2-c]imidazol-3-one (15 mg, MS (ES+): 353.3 (MH$^+$), white solid).

Example 43

6-[(S)-2-((E)-5-Hydroxy-adamantan-2-yl)-3-oxo-tetrahydro-pyrrolo[1,2-c]imidazol-7a-ylmethoxy]-nicotinonitrile This material was obtained in analogy to example 18 using (S)-2-((E)-5-hydroxy-adamantan-2-yl)-7a-hydroxymethyl-hexahydro-pyrrolo[1,2-c]imidazol-3-one (example 37) (50 mg), to give after chromatography over silica gel the desired 6-[(S)-2-((E)-5-hydroxy-adamantan-2-yl)-3-oxo-tetrahydro-pyrrolo[1,2-c]imidazol-7a-ylmethoxy]-nicotinonitrile (27 mg, MS (ES+): 409.5 (MH$^+$), off-white solid).

Example 44

N-{(E)-4-[(R)-7a-(4-Fluoro-phenyl)-3-oxo-tetrahydro-pyrrolo[1,2-c]imidazol-2-yl]-adamantan-1-yl}-acetamide Trifluoromethanesulfonic anhydride (23 µL) and acetonitril (14 µL) was added into a round bottom flask along with DCM (0.5 mL). To this was added (R)-7a-(4-fluoro-phenyl)-2-((E)-5-hydroxy-adamantan-2-yl)-hexahydro-pyrrolo[1,2-c]imidazol-3-one (50 mg, example 93) dissolved in DCM (0.5 mL) dropwise via syringe. The reaction mixture was stirred at RT for 22 hours and then poured onto saturated aqueous sodium bicarbonate solution and the mixture was extracted with DCM (3×). The combined organic phases were dried over sodium sulfate. Filtration of the drying agent and evaporation of the volatiles in vacuo afforded a crude residue that was purified via flash column chromatography over silica gel (100% EtOAc to 15% MeOH in EtOAc) to give the desired N-{(E)-4-[(R)-7a-(4-fluoro-phenyl)-3-oxo-tetrahydro-pyrrolo[1,2-c]imidazol-2-yl]-adamantan-1-yl}-acetamide (11 mg, MS (ES+): 412.5 (MH$^+$)) as a white solid.

Examples 45 and 46

(rac)-8a-Benzyloxymethyl-2-((Z)-5-hydroxy-adamantan-2-yl)-hexahydro-imidazo[1,5-a]pyridin-3-one (45) and (rac)-8a-benzyloxymethyl-2-((E)-5-hydroxy-adamantan-2-yl)-hexahydro-imidazo[1,5-a]pyridin-3-one (46)

These materials were obtained in analogy to example 12 (step A-E) using 1-(tert-butoxycarbonyl)-2-piperidinecarboxylic acid and (step A) (5 g), to give after silica gel separation in step E the desired (rac)-8a-benzyloxymethyl-2-((Z)-5-hydroxy-adamantan-2-yl)-hexahydro-imidazo[1,5-a]pyridin-3-one (386 mg, MS (ES+): 411.5 (MH$^+$), white solid) and (rac)-8a-benzyloxymethyl-2-((E)-5-hydroxy-adamantan-2-yl)-hexahydro-imidazo[1,5-a]pyridin-3-one (204 mg, MS (ES+): 411.5 (MH$^+$), white solid).

Example 47

(E/Z)-4-((rac)-7a-Benzyloxymethyl-3-oxo-tetrahydro-pyrrolo[1,2-c]imidazol-2-yl)-adamantane-1-carboxylic Acid Methyl Ester Step A] (rac)-2-Benzyloxymethyl-2-carbamoyl-pyrrolidine-1-carboxylic Acid Tert-butyl Ester This material was prepared in analogy to example 1 and 2, step A, using 2-benzyloxymethyl-pyrrolidine-1,2-dicarboxylic acid 1-tert-butyl ester (1.426 g, see example 12, step A) and ammonia solution (320 μL of a 25% solution in water) to give the desired (rac)-2-benzyloxymethyl-2-carbamoyl-pyrrolidine-1-carboxylic acid tert-butyl ester (1.5 g, MS (ES+): 335.3 (MH$^+$)) as a yellow oil.

Step B] (rac)-2-Benzyloxymethyl-pyrrolidine-2-carboxylic Acid Amide

This material was prepared in analogy to example 1 and 2, step B, using 2-benzyloxymethyl-2-carbamoyl-pyrrolidine-1-carboxylic acid tert-butyl ester (1.5 g) to give the desired (rac)-2-benzyloxymethyl-pyrrolidine-2-carboxylic acid amide (1.05 g, MS (ES+): 235.2 (MH$^+$)) as a yellow oil.

Step C] C-((rac)-2-Benzyloxymethyl-pyrrolidin-2-yl)-methylamine

This material was prepared in analogy to example 1 and 2, step C, using 2-benzyloxymethyl-pyrrolidine-2-carboxylic acid amide (1.05 g) to give C-((rac)-2-benzyloxymethyl-pyrrolidin-2-yl)-methylamine (874 mg, MS (ES+): 221.3 (MH$^+$)) as a yellow oil.

Step D] (E/Z)-4-[((rac)-2-Benzyloxymethyl-pyrrolidin-2-ylmethyl)-amino]-adamantane-1-carboxylic Acid Methyl Ester This material was prepared in analogy to example 8, step A, using C-((rac)-2-benzyloxymethyl-pyrrolidin-2-yl)-methylamine (0.466 g) to give the desired (E/Z)-4-[((rac)-2-benzyloxymethyl-pyrrolidin-2-ylmethyl)-amino]-adamantane-1-carboxylic acid methyl ester (950 mg, MS (ES+): 413.4 (MH$^+$)) as a yellow oil.

Step E] (E/Z)-4-((rac)-7a-Benzyloxymethyl-3-oxo-tetrahydro-pyrrolo[1,2-c]imidazol-2-yl)-adamantane-1-carboxylic Acid Methyl Ester This material was obtained in analogy to example 1 and 2 (step D) using (E/Z)-4-[((rac)-2-benzyloxymethyl-pyrrolidin-2-ylmethyl)-amino]-adamantane-1-carboxylic acid methyl ester (1.58 g), to give (E/Z)-4-((rac)-7a-benzyloxymethyl-3-oxo-tetrahydro-pyrrolo[1,2-c]imidazol-2-yl)-adamantane-1-carboxylic acid methyl ester as the E/Z mixture (694 mg, MS (ES+): 439.3 (MH$^+$), light yellow solid).

Examples 48 and 49

(R)-2-((Z)-5-Hydroxy-adamantan-2-yl)-7a-phenethyl-hexahydro-pyrrolo[1,2-c]imidazol-3-one (48) and (R)-2-((E)-5-Hydroxy-adamantan-2-yl)-7a-phenethyl-hexahydro-pyrrolo[1,2-c]imidazol-3-one (49)

These materials were obtained in analogy to example 1 and 2 (step A-D) using BOC-(R)-alpha-phenethyl-L-proline (step A) (2 g), to give after silica gel separation in step D the desired (R)-2-((Z)-5-hydroxy-adamantan-2-yl)-7a-phenethyl-hexahydro-pyrrolo[1,2-c]imidazol-3-one (137 mg, MS (ES+): 381.5 (MH$^+$), light yellow gum) and (R)-2-((E)-5-hydroxy-adamantan-2-yl)-7a-phenethyl-hexahydro-pyrrolo[1,2-c]imidazol-3-one (206 mg, MS (ES+): 381.5 (MH$^+$), light yellow gum).

Example 50

(rac)-2-(2-Chloro-benzyl)-7a-methyl-hexahydro-pyrrolo[1,2-c]imidazol-3-one

Step A] (rac)-2-Hydroxymethyl-2-methyl-pyrrolidine-1-carboxylic Acid Tert-butyl Ester To a solution of commercially available (S)-2-methyl-pyrrolidine-1,2-dicarboxylic acid 1-tert-butyl ester (5 g, 0.021 mol) dissolved in DCM (150 mL) was added BH$_3$-DMS (3.3 mL 0.043 mol) at 0° C., dropwise over the course of 45 min with stirring. The reaction mixture was stirred for 5 h at room temperature. The reaction mixture was treated with DCM (150 mL) and water (50 mL). The organic layer was isolated, washed with saturated NaHCO$_3$ solution (2×50 mL) followed by brine (2×50 mL), dried (anhydrous Na$_2$SO$_4$), and concentrated using rotary evaporator to give desired (rac)-2-hydroxymethyl-2-methyl-pyrrolidine-1-carboxylic acid tert-butyl ester yellowish brown liquid (4.0 g, 86%).

Step B]
(rac)-2-Formyl-2-methyl-pyrrolidine-1-carboxylic Acid Tert-butyl Ester

Dess Martin Periodinane (7.8 g, 0.0186 mol) was added in one portion to the solution of (rac)-2-hydroxymethyl-2-methyl-pyrrolidine-1-carboxylic acid tert-butyl ester (2 g, 0.0093 mol) in DCM (50 mL) under an inert atmosphere. The reaction was stirred until completion (about 2 h) then quenched with saturated solution of sodium thiosulphate, extracted with DCM (3×100 mL) washed with brine (50 mL), dried over anhydrous sodium sulphate, and concentrated using a rotary evaporator to afford 1.6 g (84%) of (rac)-2-formyl-2-methyl-pyrrolidine-1-carboxylic acid tert-butyl ester as a light brown colored oil.

Step C] (rac)-2-[(2-Chloro-benzylamino)-methyl]-2-methyl-pyrrolidine-1-carboxylic Acid Tert-butyl Ester To a solution of (rac)-2-formyl-2-methyl-pyrrolidine-1-carboxylic acid tert-butyl ester (0.7 g, 1 eq) and 2-chloro-benzylamine (1.2 eq) in DCE (20 mL) was added acetic acid (0.8 eq) and allowed to stir for 20 minutes followed by the addition of sodium triacetoxyborohydride (2 eq). The reaction mixture was stirred for 12 h. After completion of reaction on TLC, the reaction was quenched with water and extracted with DCM (3×50 mL). The organic layer was dried over anhydrous $Na_2SO_4$ and concentrated using rotary evaporator to give sticky crude product, which was then purified with column chromatography (2-5% Methanol:DCM, Mesh Size-100-200 silica, Diameter of column—3.0 cm, Height of silica—approx. 4 inch) to afford the desired (rac)-2-[(2-chloro-benzylamino)-methyl]-2-methyl-pyrrolidine-1-carboxylic acid tert-butyl ester as a sticky solid (40-70%).

Step D] (2-Chloro-benzyl)-((rac)-2-methyl-pyrrolidin-2-ylmethyl)-amine

TFA (4 mL) was added to the solution of (rac)-2-[(2-chloro-benzylamino)-methyl]-2-methyl-pyrrolidine-1-carboxylic acid tert-butyl ester (0.4 g) in DCM (15 mL) at 0° C. and stirred the reaction mixture at rt for 12 h. The reaction was monitored by TLC. After completion, the reaction mixture was concentrated under reduced pressure using a rotary evaporator and washed with ether (3×10 mL). The crude was basified with sodium bicarbonate and the aqueous layer was extracted with DCM (3×50 mL). The organic layer was dried over anhydrous $Na_2SO_4$ and distilled using rotary evaporator to give the desired (2-chloro-benzyl)-((rac)-2-methyl-pyrrolidin-2-ylmethyl)-amine as a sticky solid (Yield 40-70%).

Step E] (rac)-2-(2-Chloro-benzyl)-7a-methyl-hexahydro-pyrrolo[1,2-c]imidazol-3-one To a cold (0° C.) solution of (2-chloro-benzyl)-((rac)-2-methyl-pyrrolidin-2-ylmethyl)-amine (0.5 g, 1 eq) in DCM (15 mL) was added a solution of triphosgene (0.5 eqv) in DCM (5 mL) over a period of 5 minutes followed by the addition of triethylamine (3 eq). The reaction mixture was allowed to stir for 4 h. After the completion of the reaction on TLC, the reaction mixture was quenched with 1M HCl (10 mL) and extracted with DCM (3×50 mL). The organic layer was dried over anhydrous sodium sulfate and concentrated using rotary evaporator to give sticky crude, which was then purified with column chromatography (1-2% Methanol: DCM, Mesh Size-100-200 silica, Diameter of column—2.5 cm, Height of silica—approx. 5 inch) to afford the desired product (rac)-2-(2-chloro-benzyl)-7a-methyl-hexahydro-pyrrolo[1,2-c]imidazol-3-one as white solid (22-70%). MS (ES+): 265.5 ($MH^+$))

Example 51

(rac)-2-Benzyl-7a-methyl-hexahydro-pyrrolo[1,2-c]imidazol-3-one

This material was prepared in analogy to example 50 using benzylamine (step C) to give the desired (rac)-2-benzyl-7a-methyl-hexahydro-pyrrolo[1,2-c]imidazol-3-one (55 mg, MS (ES+): 231.3 ($MH^+$)) as a white solid.

Example 52

(E/Z)-4-((rac)-7a-Hydroxymethyl-3-oxo-tetrahydro-pyrrolo[1,2-c]imidazol-2-yl)-adamantane-1-carboxylic Acid Methyl Ester This material was prepared in analogy to example 17 using (E/Z)-4-((rac)-7a-benzyloxymethyl-3-oxo-tetrahydro-pyrrolo[1,2-c]imidazol-2-yl)-adamantane-1-carboxylic acid methyl ester (340 mg, example 47), to give the desired (rac)-(E/Z)-4-(7a -hydroxymethyl-3-oxo-tetrahydro-pyrrolo[1,2-c]imidazol-2-yl)-adamantane-1-carboxylic acid methyl ester (158 mg, MS (ES+): 349.3 ($MH^+$)) as a colourless gum.

Example 53

(E/Z)-4-((rac)-7a-Benzyloxymethyl-3-oxo-tetrahydro-pyrrolo[1,2-c]imidazol-2-yl)-adamantane-1-carboxylic acid This material was prepared in analogy to example 11 using (E/Z)-4-((rac)-7a-benzyloxymethyl-3-oxo-tetrahydro-pyrrolo[1,2-c]imidazol-2-yl)-adamantane-1-carboxylic acid methyl ester (350 mg), to give (E/Z)-4-((rac)-7a-benzyloxymethyl-3-oxo-tetrahydro-pyrrolo[1,2-c]imidazol-2-yl)-adamantane-1-carboxylic acid (304 mg, MS (ES−): 423.5 (M−H)) as a beige gum.

Examples 54 and 55

(rac)-6,6-Difluoro-2-((Z)-5-hydroxy-adamantan-2-yl)-hexahydro-pyrrolo[1,2-c]imidazol-3-one (54) and (rac)-6,6-Difluoro-2-((E)-5-hydroxy-adamantan-2-yl)-hexahydro-pyrrolo[1,2-c]imidazol-3-one (55)

Step A] (S)-4,4-Difluoro-2-(5-hydroxy-adamantan-2-ylcarbamoyl)-pyrrolidine-1-carboxylic Acid Benzyl Ester To a solution of 4-amino-adamantan-1-ol (0.58 g, g, 0.0035 mol) in DMF (12 mL) was added (S)-4,4-difluoro-pyrrolidine-1,2-dicarboxylic acid 1-benzyl ester (1.0 g, CAS: 72180-27-9, Journal of Medicinal Chemistry, 2007, 50(20), 4953-4975), NMM (0.9 mL) and HOBT (0.644 g), and the reaction was stirred for 10 minutes. EDCI (0.80 g) was then added and the reaction mixture was stirred at room temperature for 5 h. The reaction was diluted with water (30 mL). The aqueous layer was extracted with ethyl acetate (3×10 mL). The organic layer was separated and dried over anhydrous $Na_2SO_4$. Concentration of the organic layer under reduced pressure using rotary evaporator gave sticky crude material, which was purified through column chromatography (10-20% ethyl acetate:hexane, silica 100-200, Diameter of column—2.5 cm, Height of silica—approx. 7 inch) to give the desired (S)-4,4-difluoro-2-(5-hydroxy-adamantan-2-ylcarbamoyl)-pyrrolidine-1-carboxylic acid benzyl ester (1.2 g, 78%) as a white solid.

Step B] (S)-4,4-Difluoro-pyrrolidine-2-carboxylic acid (5-hydroxy-adamantan-2-yl)-amide Pd—C (10%, 0.5 g) was added to a solution of (S)-4,4-difluoro-2-(5-hydroxy-adamantan-2-ylcarbamoyl)-pyrrolidine-1-carboxylic acid benzyl ester (1.2 g) in ethanol (50 mL)

and the reaction mixture was hydrogenated (1 atm pressure) under stirring condition for 10 h. Reaction was monitored by TLC. After completion, reaction mixture was filtrated through Celite®. The filtrate was concentrated under reduced pressure using a rotary evaporator to give 0.8 g (93%) of the desired (S)-4,4-difluoro-pyrrolidine-2-carboxylic acid (5-hydroxy-adamantan-2-yl)-amide.

Step C] 4-[((S)-4,4-Difluoro-pyrrolidin-2-ylmethyl)-amino]-adamantan-1-ol

Lithium aluminium hydride (0.51 g) was added in portions to the solution of (S)-4,4-difluoro-pyrrolidine-2-carboxylic acid (5-hydroxy-adamantan-2-yl)-amide (1.2 g) in THF (15 mL) at RT. The reaction mixture was refluxed for 24 h. The reaction mixture was quenched with saturated aqueous sodium sulfate solution (15 mL) at 0° C., filtered through Celite® and extracted with ethyl acetate (3×10 mL). The organic layer was dried over anhydrous $Na_2SO_4$ and concentrated under high vacuum using rotary evaporator to give a crude material, which was purified through column chromatography (3% MeOH:DCM, silica 100-200 mesh, Diameter of column—2.5 cm, Height of silica—approx. 7 inch) to afford the desired 4-[((S)-4,4-difluoro-pyrrolidin-2-ylmethyl)-amino]-adamantan-1-ol as a white solid (0.5 g).

Step D] (S)-6,6-Difluoro-2-((Z)-5-hydroxy-adamantan-2-yl)-hexahydro-pyrrolo[1,2-c]imidazol-3-one (example 54) and (S)-6,6-Difluoro-2-((E)-5-hydroxy-adamantan-2-yl)-hexahydro-pyrrolo[1,2-c]imidazol-3-one (example 55)

To stirred cooled (0° C.) solution of 4-[((S)-4,4-difluoro-pyrrolidin-2-ylmethyl)-amino]-adamantan-1-ol (500 mg) in DCM (15 mL) was added a solution of triphosgene (0.4 eq) in DCM (5 mL). The reaction mixture was stirred at 0° C. for 10 min, and then triethylamine (2.25 eq) was added dropwise and the reaction mixture was stirred at rt for 5 h. The reaction mixture was quenched with 1N HCl (15 mL) and extracted with DCM (3×20 mL). The organic layer was dried over anhydrous $Na_2SO_4$ and concentrated under high vacuum using rotary evaporation to give the crude material, which was purified with column chromatography (3% MeOH: DCM, silica 100-200 mesh, diameter of column—2.5 cm, height of silica—approx. 7 inch) to give the desired (S)-6,6-difluoro-2-((Z)-5-hydroxy-adamantan-2-yl)-hexahydro-pyrrolo[1,2-c]imidazol-3-one (145 mg, MS (ES+): 313.2 (M+H), white solid) and (S)-6,6-difluoro-2-((E)-5-hydroxy-adamantan-2-yl)-hexahydro-pyrrolo[1,2-c]imidazol-3-one (123 mg, MS (ES+): 313.2 (M+H), white solid).

Example 56

(E/Z)-4-[(rac)-7a-(5-Cyano-pyridin-2-yloxymethyl)-3-oxo-tetrahydro-pyrrolo[1,2-c]imidazol-2-yl]-adamantane-1-carboxylic Acid Methyl Ester This material was prepared in analogy to example 18 using (E/Z)-4-((rac)-7a-hydroxymethyl-3-oxo-tetrahydro-pyrrolo[1,2-c]imidazol-2-yl)-adamantane-1-carboxylic acid methyl ester (80 mg, example 52), to give the desired (E/Z)-4-[7a-(5-cyano-pyridin-2-yloxymethyl)-3-oxo-tetrahydro-pyrrolo[1,2-c]imidazol-2-yl]-adamantane-1-carboxylic acid methyl ester (49 mg, MS (ES+): 451.3 (M+H)) as a white solid.

Example 57

(6R,7aS)-6-(2,4-Difluoro-benzyloxy)-2-((E)-5-hydroxy-adamantan-2-yl)-hexahydro-pyrrolo[1,2-c]imidazol-3-one To a suspension of (6R,7aS)-6-hydroxy-2-((E)-5-hydroxy-adamantan-2-yl)-hexahydro-pyrrolo[1,2-c]imidazol-3-one (27 mg, example 32) in THF (1.0 mL) was added at 0° C. a solution of NaHMDS (92 µL of a 1M solution in THF) dropwise via syringe. The suspension was stirred for 10 minutes after which a solution of 2,4-difluorobenzylbromide (19 mg) in THF (0.5 mL) was added dropwise via syringe. The reaction mixture was stirred overnight and then quenched with saturated sodium bicarbonate solution and diluted with EtOAc. The phases were separated and the aqueous phase was extracted with further EtOAc. The combined aqueous phases were washed with dilute aqueous HCl and dried over sodium sulfate. Filtration and evaporation in vacuo afforded a crude residue which was purified via flash column chromatography over silica gel (eluent EtOAc) to afford the desired (6R,7aS)-6-(2,4-difluoro-benzyloxy)-2-((E)-5-hydroxy-adamantan-2-yl)-hexahydro-pyrrolo[1,2-c]imidazol-3-one (13 mg, MS (ES+): 419.5 (MH$^+$)) as a light yellow gum.

Example 58

6-[(rac)-2-((E)-5-Hydroxy-adamantan-2-yl)-3-oxo-hexahydro-imidazo[1,5-a]pyridin-8a-ylmethoxy]-nicotinonitrile Step A] (rac)-2-((E)-5-Hydroxy-adamantan-2-yl)-8α-hydroxymethyl-hexahydro-imidazo[1,5-a]pyridin-3-one To a solution of (rac)-8a-benzyloxymethyl-2-((E)-5-hydroxy-adamantan-2-yl)-hexahydro-imidazo[1,5-a]pyridin-3-one (182 mg, example 46) in EtOAc (3.5 mL) was added Pd/C (100 mg) and the reaction mixture was flushed with hydrogen gas using a balloon and vacuum manifold and maintained under a hydrogen atmosphere. After 2 hours the reaction mixture was filtered through Celite® and washed through with further EtOAc followed by small amounts of DCM/MeOH. Evaporation of the solvent afforded a crude residue which was purified over flash column chromatography over silica gel (eluent DCM/MeOH 95:5) to give the desired (rac)-2-((E)-5-hydroxy-adamantan-2-yl)-8α-hydroxymethyl-hexahydro-imidazo[1,5-a]pyridin-3-one (74 mg, MS (ES+): 321.4 (MH$^+$)) as a white solid.

Step B] 6-[(rac)-2-((E)-5-hydroxy-adamantan-2-yl)-3-oxo-hexahydro-imidazo[1,5-a]pyridin-8a-yl-methoxy]-nicotinonitrile This material was prepared in analogy to example 18 using (rac)-2-((E)-5-hydroxy-adamantan-2-yl)-8α-hydroxymethyl-hexahydro-imidazo[1,5-a]pyridin-3-one (40 mg), to give the desired 6-[(rac)-2-((E)-5-hydroxy-adamantan-2-yl)-3-oxo-hexahydro-imidazo[1,5-a]pyridin-8a-ylmethoxy]-nicotinonitrile (6 mg, MS (ES+): 423.3 (M+H)) as a light yellow solid.

Example 59

(rac)-2-[1-(4-Chloro-phenyl)-ethyl]-7a-methyl-hexahydro-pyrrolo[1,2-c]imidazol-3-one This material was prepared in analogy to example 50 using 1-(4-chloro-phenyl)-ethylamine (known compound, CAS 6299-02-1) (step C) to give the desired (rac)-2-[1-(4-chlorophenyl)-ethyl]-7a-methyl-hexahydro-pyrrolo[1,2-c]imidazol-3-one (65 mg, MS (ES+): 279.3 (MH$^+$)) as a white solid.

Example 60

(rac)-2-(3-Chloro-benzyl)-7a-methyl-hexahydro-pyrrolo[1,2-c]imidazol-3-one

This material was prepared in analogy to example 50 using 3-chloro-benzylamine (step C) to give the desired (rac)-2-(3-chloro-benzyl)-7a-methyl-hexahydro-pyrrolo[1,2-c]imidazol-3-one (64 mg, MS (ES+): 265.2 (MH$^+$)) as a white solid.

Example 61

(rac)-7a-Methyl-2-(1-phenyl-ethyl)-hexahydro-pyrrolo[1,2-c]imidazol-3-one

This material was prepared in analogy to example 50 using 1-phenyl-ethylamine (step C) to give the desired (rac)-7a-methyl-2-(1-phenyl-ethyl)-hexahydro-pyrrolo[1,2-c]imidazol-3-one (90 mg, MS (ES+): 245.2 (MH$^+$)) as a white solid.

Example 62

(E/Z)-4-((rac)-7a-Benzyloxymethyl-3-oxo-tetrahydro-pyrrolo[1,2-c]imidazol-2-yl)-adamantane-1-carboxylic Acid Amide This material was prepared in analogy to example 16 using (E/Z)-4-((rac)-7a-benzyloxymethyl-3-oxo-tetrahydro-pyrrolo[1,2-c]imidazol-2-yl)-adamantane-1-carboxylic acid (50 mg, example 53), to give (E/Z)-4-((rac)-7a-benzyloxymethyl-3-oxo-tetrahydro-pyrrolo[1,2-c]imidazol-2-yl)-adamantane-1-carboxylic acid amide (8 mg, MS (ES+): 424.3 (M+H)) as a white solid.

Example 63

(E/Z)-4-[(rac)-7a-(5-Cyano-pyridin-2-yloxymethyl)-3-oxo-tetrahydro-pyrrolo[1,2-c]imidazol-2-yl]-adamantane-1-carboxylic Acid Amide Step A] (E/Z)-4-[(rac)-7a-(5-Cyano-pyridin-2-yloxymethyl)-3-oxo-tetrahydro-pyrrolo[1,2-c]imidazol-2-yl]-adamantane-1-carboxylic Acid To a solution of (E/Z)-4-[(rac)-7a-(5-cyano-pyridin-2-yloxymethyl)-3-oxo-tetrahydro-pyrrolo[1,2-c]imidazol-2-yl]-adamantane-1-carboxylic acid methyl ester (45 mg, example 56) in THF was added TMSOK (45 mg) and the reaction was stirred at 40° C. for 2 days. The reaction was diluted with water and Et$_2$O and the phases were separated. The aqueous was extracted with further Et$_2$O and the combined organic phases were discarded. The aqueous phase was acidified to pH=1 and extracted with EtOAc (4×) and the combined organics were dried with sodium sulfate, filtered and reduced in vacuo to afford the desired (E/Z)-4-[(rac)-7a-(5-cyano-pyridin-2-yloxymethyl)-3-oxo-tetrahydro-pyrrolo[1,2-c]imidazol-2-yl]-adamantane-1-carboxylic acid (35 mg, MS (ES−): 435.5 (M−H)) as white solid.

Step B] (E/Z)-4-[(rac)-7a-(5-Cyano-pyridin-2-yloxymethyl)-3-oxo-tetrahydro-pyrrolo[1,2-c]imidazol-2-yl]-adamantane-1-carboxylic Acid Amide This material was prepared in analogy to example 16 using (E/Z)-4-[(rac)-7a-(5-cyano-pyridin-2-yloxymethyl)-3-oxo-tetrahydro-pyrrolo[1,2-c]imidazol-2-yl]-adamantane-1-carboxylic acid (35 mg), to give the desired (E/Z)-4-[(rac)-7a-(5-cyano-pyridin-2-yloxymethyl)-3-oxo-tetrahydro-pyrrolo[1,2-c]imidazol-2-yl]-adamantane-1-carboxylic acid amide (3 mg, MS (ES+): 436.2 (M+H)) as white solid.

Examples 64 and 65

(rac)-7a-Cyclopropylmethyl-2-((Z)-5-hydroxy-adamantan-2-yl)-hexahydro-pyrrolo[1,2-c]imidazol-3-one and (rac)-7a-Cyclopropylmethyl-2-((E)-5-hydroxy-adamantan-2-yl)-hexahydro-pyrrolo[1,2-c]imidazol-3-one These materials were obtained in analogy to example 12 (step A-E) using bromomethyl-cyclopropane (step A), to give after separation of the E and Z isomer via flash column chromatography over silica gel in step E the desired (rac)-7a-cyclopropylmethyl-2-((Z)-5-hydroxy-adamantan-2-yl)-hexahydro-pyrrolo[1,2-c]imidazol-3-one (51 mg, MS (ES+): 331.1 (MH$^+$), white solid) and (rac)-7a-Cyclopropylmethyl-2-((E)-5-hydroxy-adamantan-2-yl)-hexahydro-pyrrolo[1,2-c]imidazol-3-one (29.1 mg, MS (ES+): 331.1 (MH$^+$), white solid).

Examples 66 and 74

(S)-6,6-Difluoro-2-((Z)-5-hydroxy-adamantan-2-yl)-7a-methyl-hexahydro-pyrrolo[1,2-c]imidazol-3-one (66) and (S)-6,6-difluoro-2-((E)-5-hydroxy-adamantan-2-yl)-7a-methyl-hexahydro-pyrrolo[1,2-c]imidazol-3-one (74)

Step A] (rac)-4,4-Difluoro-2-methyl-pyrrolidine-1,2-dicarboxylic acid 1-tert-butyl Ester To a cooled (−78° C.) solution of diisopropylamine (4.9 mL, 0.032 mol) in dry THF (15 mL), n-BuLi (0.030 mol) was added dropwise under argon atmosphere, stirred the reaction mixture for 30 min at −78° C., then for one hour at −20° C. The resulting LDA solution was transferred to a solution of (S)-4,4-difluoro-pyrrolidine-1,2-dicarboxylic acid 1-tert-butyl ester (2.7 g, 0.010 mol) in THF (15 mL), via cannula and then stirred for 30 minutes at −78° C., then at 0° C. for one hour. The reaction mixture was once again cooled to −78° C., and methyl iodide (0.54 mL, 0.010 mol) was added over 10 min and then warmed to RT over 2 h. After completion of the reaction, the reaction mixture was quenched with 1N HCl (20 mL) and extracted with DCM. The organic layer was concentrated under reduced pressure using a rotary evaporator to give a crude gum, which was purified through column chromatography (10-20% ethyl acetate:hexane, basic alumina, diameter of column—2.5 cm, Height of alumina—approx. 7 inch) to give the desired (rac)-4,4-difluoro-2-methyl-pyrrolidine-1,2-dicarboxylic acid 1-tert-butyl ester (1.1 g) as a white solid.

Step B] (rac)-4,4-Difluoro-2-((E/Z)-5-hydroxy-adamantan-2-ylcarbamoyl)-2-methyl-pyrrolidine-1-carboxylic Acid Tert-butyl Ester To a solution of 4-amino-adamantan-1-ol (685 mg, 0.004 mol) in DMF (20 mL) was added (rac)-4,4-difluoro-2-methyl-pyrrolidine-1,2-dicarboxylic acid 1-tert-butyl ester (1.1 g, 0.004 mol), NMM (1.0 L, 0.008 mol) and HOBT (762 mg, 0.0049 mol) and the reaction was stirred for 10 min. Then, EDCI (954 mg, 0.0049 mol) was then added and the reaction mixture was stirred at room temperature for 5 h. The reaction was diluted with water (30 mL). The aqueous layer was extracted with ethyl acetate (3×10 mL). The organic layer was separated and dried over anhydrous $Na_2SO_4$. Concentration of the organic layer under reduced pressure using a rotary evaporator gave a crude gum, which was purified via column chromatography (10-20% ethyl acetate:hexane, silica 100-200, diameter of column—2.5 cm, height of silica—approx. 7 inch) to give the desired (rac)-4,4-difluoro-2-((E/Z)-5-hydroxy-adamantan-2-ylcarbamoyl)-2-methyl-pyrrolidine-1-carboxylic acid tert-butyl ester (940 mg).

Step C-E] (rac)-6,6-Difluoro-2-((Z)-5-hydroxy-adamantan-2-yl)-7a-methyl-hexahydro-pyrrolo[1,2-c]imidazol-3-one (example 66) and (rac)-6,6-difluoro-2-((E)-5-hydroxy-adamantan-2-yl)-7a-methyl-hexahydro-pyrrolo[1,2-c]imidazol-3-one (example 74)

These materials were obtained in analogy to example 1 and 2 (step B-D) using (rac)-4,4-difluoro-2-((E/Z)-5-hydroxy-adamantan-2-ylcarbamoyl)-2-methyl-pyrrolidine-1-carboxylic acid tert-butyl ester (step B), to give after separation of the E and Z isomer via flash column chromatography over silica gel in step D the desired (rac)-6,6-Difluoro-2-((Z)-5-hydroxy-adamantan-2-yl)-7a-methyl-hexahydro-pyrrolo[1,2-c]imidazol-3-one (90 mg, MS (ES+): 327.2 ($MH^+$), white solid) and (rac)-6,6-difluoro-2-((E)-5-hydroxy-adamantan-2-yl)-7a-methyl-hexahydro-pyrrolo[1,2-c]imidazol-3-one (72 mg, MS (ES+): 327.2 ($MH^+$), white solid).

Example 67

(rac)-7a-(4-Chloro-phenyl)-2-((E)-5-hydroxy-adamantan-2-yl)-hexahydro-pyrrolo[1,2-c]imidazol-3-one This material was obtained in analogy to example 86 (step A-I) using (4-chloro-phenyl)-acetic acid ethyl ester (step A), to give after step I the desired (rac)-7a-(4-chloro-phenyl)-2-((E)-5-hydroxy-adamantan-2-yl)-hexahydro-pyrrolo[1,2-c]imidazol-3-one (20 mg, MS (ES+): 387.2 ($MH^+$)) as a light yellow solid.

Example 68

(rac)-2-(3-Chloro-phenyl)-7a-methyl-hexahydro-pyrrolo[1,2-c]imidazol-3-one

This material was prepared in analogy to example 50 using 3-chloro-phenylamine (step C) to give the desired (rac)-2-(3-chloro-phenyl)-7a-methyl-hexahydro-pyrrolo[1,2-c]imidazol-3-one (150 mg, MS (ES+): 251.1 ($MH^+$)) as a white solid.

Example 69

(rac)-2-((E/Z)-5-Methanesulfonyl-adamantan-2-yl)-7a-phenyl-hexahydro-pyrrolo[1,2-c]imidazol-3-one This material was prepared in analogy to example 40, 41 and 86 (steps A-I) using phenyl-acetic acid ethyl ester (step A), and 5-methanesulfonyl-adamantan-2-ylamine (step H, known compound, CAS 924298-56-6, see Bioorganic & Medicinal Chemistry Letters (2007), 17(2), 527-532) to give the (rac)-2-((E/Z)-5-methanesulfonyl-adamantan-2-yl)-7a-phenyl-hexahydro-pyrrolo[1,2-c]imidazol-3-one (19 mg, MS (ES+): 415.3 ($MH^+$)) as a colourless solid.

Example 70

(rac)-2-(2,4-Difluoro-benzyl)-7a-methyl-hexahydro-pyrrolo[1,2-c]imidazol-3-one

This material was prepared in analogy to example 50 using 2,4-difluoro-benzylamine (step C) to give the desired (rac)-2-(2,4-difluoro-benzyl)-7a-methyl-hexahydro-pyrrolo[1,2-c]imidazol-3-one (35 mg, MS (ES+): 267.19 ($MH^+$)) as a white solid.

Example 71

2-(2-Chloro-phenyl)-7a-methyl-hexahydro-pyrrolo[1,2-c]imidazol-3-one

This material was prepared in analogy to example 50 using 3-chloro-phenylamine (step C) to give the desired (rac)-2-(2-chloro-phenyl)-7a-methyl-hexahydro-pyrrolo[1,2-c]imidazol-3-one (30 mg, MS (ESt): 251.2 ($MH^+$)) as a white solid.

Example 72

(rac)-2-(4-Chloro-benzyl)-7a-methyl-hexahydro-pyrrolo[1,2-c]imidazol-3-one

This material was prepared in analogy to example 50 using 4-chloro-benzylamine (step C) to give the desired (rac)-2-(4-chloro-benzyl)-7a-methyl-hexahydro-pyrrolo[1,2-c]imidazol-3-one (20 mg, MS (ES+): 265.3 ($MH^+$)) as a white solid.

Example 73

(rac)-2-(2,4-Dichloro-phenyl)-7a-methyl-hexahydro-pyrrolo[1,2-c]imidazol-3-one

This material was prepared in analogy to example 50 using 2,4-dichloro-phenylamine (step C) to give the desired (rac)-2-(2,4-dichloro-phenyl)-7a-methyl-hexahydro-pyrrolo[1,2-c]imidazol-3-one (135 mg, MS (ES+): 285.1 ($MH^+$)) as a white solid.

Example 75

(S)-2-(3-Chloro-phenyl)-6,6-difluoro-hexahydro-pyrrolo[1,2-c]imidazol-3-one

Step A] (S)-4,4-Difluoro-2-hydroxymethyl-pyrrolidine-1-carboxylic Acid Tert-butyl Ester Lithium aluminium hydride (0.42 g, 0.011 mol) was added in portions to a solution of commercially available (S)-4,4-difluoro-pyrrolidine-1,2-dicarboxylic acid 1-tert-butyl ester 2-methyl ester (1 g, 0.0037 mol) in dry THF (25 mL) att 0° C. and allowed to stir for 3 h. The reaction was monitored by TLC and after completion, it was quenched with sat. solution of $Na_2SO_4$ in cold condition. The reaction mixture was filtered through a Celite® plug. The filtrate was concentrated under reduced pressure using a rotary evaporator to give a crude material, which was purified via column chromatography (2-7% methanol:DCM, mesh Size-100-200 silica, diameter of column—2.5 cm, height of silica—approx. 6 inch) to give the desired (S)-4,4-difluoro-2-hydroxymethyl-pyrrolidine-1-carboxylic acid tert-butyl ester (0.4 g) as a beige solid.

Step B] (S)-4,4-Difluoro-2-formyl-pyrrolidine-1-carboxylic Acid Tert-butyl Ester Dess Martin Periodinane (0.9 g, 0.0021 mol) was added in one portion to a solution of (S)-4,4-difluoro-2-hydroxymethyl-pyrrolidine-1-carboxylic acid tert-butyl ester (0.4 g, 0.0016 mol) in DCM (50 mL) under an inert atmosphere. The reaction was stirred until completion (about 2 h) and then quenched with saturated solution of sodium thiosulphate, extracted with DCM (3×100 mL) washed with brine (50 mL), dried over anhydrous sodium sulphate, and concentrated using a rotary evaporator to afford 0.35 g of the desired (S)-4,4-difluoro-2-formyl-pyrrolidine-1-carboxylic acid tert-butyl ester as a light brown colored oil product.

Step C] (S)-2-[(3-Chloro-phenylamino)-methyl]-4,4-difluoro-pyrrolidine-1-carboxylic Acid Tert-butyl Ester Solution of (S)-4,4-difluoro-2-formyl-pyrrolidine-1-carboxylic acid tert-butyl ester (1 g, 0.0042 mol) and 3-chloroaniline (0.53 mL, 0.0042 mol) in titanium tetraisopropoxide (5 mL) was allowed to stir for 12 h. The reaction was monitored by TLC. After disappearance of starting reaction on TLC, the mixture was diluted with methanol (20 mL) followed by the addition of sodium borohydride (0.33 g, 0.0084 mol) in portions. The reaction mixture was stirred for 6 h. The reaction was quenched with water and extracted with DCM (3×50 mL). The organic layer was dried over anhydrous $Na_2SO_4$ and the volatiles were removed using a rotary evaporator to give a crude oil, which was then purified via column chromatography (5% methanol: DCM, mesh Size—100-200 silica, diameter of column—2.5 cm, height of silica—approx. 4 inch) to afford the desired (S)-2-[(3-chloro-phenylamino)-methyl]-4,4-difluoro-pyrrolidine-1-carboxylic acid tert-butyl ester as a sticky solid (0.15 g, 12%).

Step D] (3-Chloro-phenyl)-((S)-4,4-difluoro-pyrrolidin-2-ylmethyl)-amine

TFA (1 mL) was added to the solution of (S)-2-[(3-chlorophenylamino)-methyl]-4,4-difluoro-pyrrolidine-1-carboxylic acid tert-butyl ester (0.16 g, 0.0004 mol) in DCM (5 mL) at 0° C. and the reaction mixture was stirred at rt for 12 h. The reaction was monitored by TLC. After completion, the reaction mixture was concentrated under reduced pressure using a rotary evaporator and washed with ether (3×10 mL). The crude was basified with sodium bicarbonate and the aqueous layer was extracted with DCM (3×50 mL). The organic layer was dried over anhydrous $Na_2SO_4$ and distilled using a rotary evaporator to give the desired (3-chloro-phenyl)-((S)-4,4-difluoro-pyrrolidin-2-ylmethyl)-amine (0.1 g) as a sticky solid.

Step E] (S)-2-(3-Chloro-phenyl)-6,6-difluoro-hexahydro-pyrrolo[1,2-c]imidazol-3-one To a cooled (0° C.) solution of (3-chloro-phenyl)-((S)-4,4-difluoro-pyrrolidin-2-ylmethyl)-amine (0.035 g, 0.00014 mol) in DCM (15 mL) was added a solution of triphosgene (0.016 g, 0.0005 eq) in DCM (5 mL) over a period of 5 minutes followed by the addition of $Et_3N$ (0.05 mL, 0.00035 mol). The reaction mixture was allowed to stir for 4 h. After the completion of the reaction on TLC, the reaction mixture was quenched with 1M HCl (10 mL) and extracted with DCM (3×50 mL). The organic layer was dried over anhydrous $Na_2SO_4$ and distilled using a rotary evaporator to give a crude residue, which was then purified with column chromatography (1-2% methanol: DCM, mesh size-100-200 silica, diameter of column-2.5 cm, height of silica-approx. 5 inch) to afford the desired (S)-2-(3-chloro-phenyl)-6,6-difluorohexahydro-pyrrolo[1,2-c]imidazol-3-one (0.20 g, 70%) as a beige solid (MS (ES+): 273.1 ($MH^+$)).

Example 76

(rac)-7a-Methyl-2-(2-trifluoromethyl-phenyl)-hexahydro-pyrrolo[1,2-c]imidazol-3-one This material was prepared in analogy to example 50 using 2-trifluoromethyl-phenylamine (step C) to give the desired 7a-methyl-2-(2-trifluoromethyl-phenyl)-hexahydro-pyrrolo[1,2-c]imidazol-3-one (230 mg, MS (ES+): 285.1 ($MH^+$)) as a white solid.

Example 77

(rac)-2-(2,5-Dichloro-phenyl)-7a-methyl-hexahydro-pyrrolo[1,2-c]imidazol-3-one

This material was prepared in analogy to example 50 using 2,5-dichloro-phenylamine (step C) to give the desired 2-(2,5-dichloro-phenyl)-7a-methyl-hexahydro-pyrrolo[1,2-c]imidazol-3-one (60 mg, MS (ES+): 285.1 ($MH^+$)) as a white solid.

Examples 78 and 82

(R)-6-Benzyloxy-2-((Z)-5-hydroxy-adamantan-2-yl)-7a-methyl-hexahydro-pyrrolo[1,2-c]imidazol-3-one (78) and (R)-6-Benzyloxy-2-((E)-5-hydroxy-adamantan-2-yl)-7a-methyl-hexahydro-pyrrolo[1,2-c]imidazol-3-one (82)

Step A] (rac)-4-Benzyloxy-2-methyl-pyrrolidine-1,2-dicarboxylic acid 1-tert-butyl Ester To a cooled (−78° C.) solution of diisopropylamine (0.032 mol) in dry THF (15 mL), n-BuLi (0.030 mol) was added dropwise under argon atmosphere, and the reaction was stirred for 30 min at −78° C., then for one hour at −20° C. The resulting LDA solution was transferred to the solution of the known compound (R)-4-benzyloxy-pyrrolidine-1,2-dicarboxylic acid 1-tert-butyl ester (CAS: 54631-81-1, e.g. Tetrahedron, 42(21), 6039-45; 1986) (3.5 g, 0.011 mol) in THF (15 mL) at −78° C., and the mixture was stirred for 30 minutes at −78° C., then at 0° C. for one hour. The reaction mixture was once again cooled to −78° C. and methyl iodide (0.82 mL, 0.013 mol) was added to it over 10 min and stirred the reaction mixture was stirred at 0° C. then at rt for one hour. After completion of the reaction by TLC, the reaction mixture was quenched with 1N HCl (20 mL) and extracted with DCM. The organic layer was concentrated under reduced pressure to give a crude material, which was purified through column chromatography (10-20% ethyl acetate:hexane, basic alumina, diameter of column—2.5 cm, height of alumina—approx. 7 inch) to afford the desired (rac)-4-benzyloxy-2-methyl-pyrrolidine-1,2-dicarboxylic acid 1-tert-butyl ester 800 mg (22%) as a white solid.

Step B-E] (rac)-6-Benzyloxy-2-((Z)-5-hydroxy-adamantan-2-yl)-7a-methyl-hexahydro-pyrrolo[1,2-c]imidazol-3-one (78) and (rac)-6-benzyloxy-2-((E)-5-hydroxy-adamantan-2-yl)-7a-methyl-hexahydro-pyrrolo[1,2-c]imidazol-3-one (82)

These materials were obtained in analogy to example 1 and 2 (step A-D) using (rac)-4-benzyloxy-2-methyl-pyrrolidine-1,2-dicarboxylic acid 1-tert-butyl ester (step A),) to give after step D the desired (rac)-6-benzyloxy-2-((Z)-5-hydroxy-adamantan-2-yl)-7a-methyl-hexahydro-pyrrolo[1,2-c]imidazol-3-one (30 mg, MS (ES+): 397.4 (MH$^+$), white solid) and (rac)-6-benzyloxy-2-((E)-5-hydroxy-adamantan-2-yl)-7a-methyl-hexahydro-pyrrolo[1,2-c]imidazol-3-one (6 mg, MS (ES+): 397.3 (MH$^+$), white solid).

Example 79

(rac)-2-[1-(2-Chloro-phenyl)-ethyl]-7a-methyl-hexahydro-pyrrolo[1,2-c]imidazol-3-one This material was prepared in analogy to example 50 using 1-(2-chloro-phenyl)-ethylamine (known compound, CAS: 39959-67-6) (step C) to give the desired (rac)-2-[1-(2-chloro-phenyl)-ethyl]-7a-methyl-hexahydro-pyrrolo[1,2-c]imidazol-3-one (170 mg, MS (ES+): 279.2 (MH$^+$)) as a white solid.

Example 80

(rac)-2-[1-(2,4-Difluoro-phenyl)-ethyl]-7a-methyl-hexahydro-pyrrolo[1,2-c]imidazol-3-one This material was prepared in analogy to example 50 using 1-(2,4-difluoro-phenyl)-ethylamine (step C) to give the desired (rac)-2-[1-(2,4-difluoro-phenyl)-ethyl]-7a-methyl-hexahydro-pyrrolo[1,2-c]imidazol-3-one (65 mg, MS (ES+): 281.2 (MH$^+$)) as a white solid.

Example 81

(rac)-2-[1-(3-Chloro-phenyl)-ethyl]-7a-methyl-hexahydro-pyrrolo[1,2-c]imidazol-3-one This material was prepared in analogy to example 50 using 1-(3-chloro-phenyl)-ethylamine (step C) to give the desired (rac)-2-[1-(3-chloro-phenyl)-ethyl]-7a-methyl-hexahydro-pyrrolo[1,2-c]imidazol-3-one (30 mg, MS (ES+): 279.2 (MH$^+$)) as a white solid.

Examples 83 and 84

(rac)-7a-(2-Fluoro-phenyl)-2-((Z)-5-hydroxy-adamantan-2-yl)-hexahydro-pyrrolo[1,2-c]imidazol-3-one and (rac)-7a-(2-Fluoro-phenyl)-2-((E)-5-hydroxy-adamantan-2-yl)-hexahydro-pyrrolo[1,2-c]imidazol-3-one These materials were obtained in analogy to example 86 (step A-I) using (2-fluoro-phenyl)-acetic acid ethylester (step A), and (E/Z)-4-amino-adamantan-1-ol (step H) to give after step I the desired (rac)-7a-(2-fluoro-phenyl)-2-((Z)-5-hydroxy-adamantan-2-yl)-hexahydro-pyrrolo[1,2-c]imidazol-3-one (13 mg, MS (ES+): 371.2 (MH$^+$), beige solid) and (rac)-7a-(2-fluoro-phenyl)-2-((E)-5-hydroxy-adamantan-2-yl)-hexahydro-pyrrolo[1,2-c]imidazol-3-one (10 mg, MS (ES+): 371.2 (MH$^+$), beige solid).

Example 85

(rac)-7a-(3-Chloro-phenyl)-2-((E)-5-hydroxy-adamantan-2-yl)-hexahydro-pyrrolo[1,2-c]imidazol-3-one This material was obtained in analogy to example 86 (step A-I) using (3-chloro-phenyl)-acetic acid ethyl ester (step A), to give after step I the desired (rac)-7a-(3-chloro-phenyl)-2-((E)-5-hydroxy-adamantan-2-yl)-hexahydro-pyrrolo[1,2-c]imidazol-3-one (141 mg, MS (ES+): 387.2 (MH$^+$)) as a yellow solid.

Example 86

(rac)-7a-(4-Fluoro-phenyl)-2-((E)-5-hydroxy-adamantan-2-yl)-hexahydro-pyrrolo[1,2-c]imidazol-3-one Step A] Bromo-(4-fluoro-phenyl)-acetic Acid Methyl Ester To a solution of methyl-4-fluorphenylacetate (10 g) in carbontetrachloride (80 mL) was added NBS (11.64 g) and AIBN (0.976 g) at RT. The reaction was then heated to reflux for 3 days. The reaction mixture was filtered and the solid washed with further carbontetrachloride. The filtrate was reduced in vacuo and the diluted with water (50 mL) and EtOAc (100 mL). The phases were separated and the aqueous phase was extracted with further EtOAc (100 mL). The combined organic phases were dried over sodium sulphate, filtered and evaporated in vacuo to afford the desired bromo-(4-fluoro-phenyl)-acetic acid methyl ester (15.0 g) as a yellow oil which was taken into the next step without further purification.

Step B] (4-Fluoro-phenyl)-(3-hydroxy-propylamino)-acetic Acid Methyl Ester

To a solution of bromo-(4-fluoro-phenyl)-acetic acid methyl ester (16.0 g) in chloroform (100 mL) was added potassium carbonate (17.9 g, finely ground) followed by 3-amino-1-propanol (4.87 g). The reaction was heated to 45° C. for 18 hours. The reaction was filtered and the filtrate was diluted with water and the phases were separated. The aqueous phase was further extracted with chloroform (3×25 mL) and the combined organics were washed with brine. The chloroform phase was dried over sodium sulfate, filtered and evaporated in vacuo to give the desired (4-fluoro-phenyl)-(3-hydroxy-propylamino)-acetic acid methyl ester (14.85 g, MS (ES+): 242.2 (MH$^+$)) as a yellow oil which was used in the next step without further purification.

Step C] (3-Chloro-propylamino)-(4-fluoro-phenyl)-acetic Acid Methyl Ester

To a solution of thionyl chloride (8.79 g) in chloroform (20 mL) was added (4-fluoro-phenyl)-(3-hydroxy-propylamino)-acetic acid methyl ester (14.85 g, dissolved in 60 mL of chloroform) dropwise via syringe. The reaction mixture was then stirred for 1.5 hours at 50° C. and the volatiles were subsequently removed in vacuo to give a solid residue which was triturated with diethyl ether (30 mL) to give the desired HCl salt of (3-chloro-propylamino)-(4-fluoro-phenyl)-acetic acid methyl ester (14.88 g, MS (ES+): 260.1 (MH$^+$)) as an off-white solid.

Step D] [tert-Butoxycarbonyl-(3-chloro-propyl)-amino]-(4-fluoro-phenyl)-acetic Acid Methyl Ester To a solution of (3-chloro-propylamino)-(4-fluoro-phenyl)-acetic acid methyl ester (14.34 g) in DMF (40 mL) was added BOC$_2$O (11.44 g) followed by triethylamine (15.9 g) and the resultant mixture was stirred overnight at 60° C. A further 0.25 equivalents of BOC$_2$O was added and the reaction mixture was stirred a further 18 hours. The reaction mixture was diluted with EtOAc (200 mL) and water (150 mL), the phases were separated and the organic phase was washed with 0.5 N HCl solution, water, brine and dried over sodium sulfate. Filtration of the drying agent and evaporation of the volatiles in vacuo afforded crude [tert-butoxycarbonyl-(3-chloro-propyl)-amino]-(4-fluoro-phenyl)-acetic acid methyl ester (10.91 g, MS (ES+): 360.1 (MH$^+$)) as a brown oil which was used in the subsequent reaction without further purification.

Step E] 2-(4-Fluoro-phenyl)-pyrrolidine-1,2-dicarboxylic acid 1-tert-butyl Ester 2-methyl Ester To a solution of [tert-butoxycarbonyl-(3-chloro-propyl)-amino]-(4-fluoro-phenyl)-acetic acid methyl ester (10.91 g) in acetonitrile (60 mL) was added benzyltriethylammoniumchloride (3.32 g) (see also Chemistry of Heterocyclic Compound, 36, 2000, 416-420) followed by solid potassium carbonate (12.1 g, finely ground). The reaction mixture was stirred at 50° C. for 20 hours. A further 1.6 g of benzyltriethylammoniumchloride and 4 g of potassium carbonate was added to push the reaction to completion. The reaction mixture was filtered and the filtrate was reduced in vacuo. The residue was diluted with water and extracted with chloroform (3×50 mL). The combined organic phases were washed with brine and dried over sodium sulfate. Filtration and evaporation of the volatiles in vacuo afforded a crude residue which was purified using flash column chromatography (EtOAc/Heptane 2:8) on silica gel to afford the desired 2-(4-Fluoro-phenyl)-pyrrolidine-1,2-dicarboxylic acid 1-tert-butyl ester 2-methyl ester (4.25, MS (ES+): 324.3 (MH$^+$)) as a pale yellow oil.

Step F] 2-(4-Fluoro-phenyl)-2-hydroxymethyl-pyrrolidine-1-carboxylic Acid Tert-butyl Ester To a suspension of lithiumaluminiumhydride (1.5 g) in dry diethyl ether (25 mL) at −20° C. was added dropwise a solution of 2-(4-fluoro-phenyl)-pyrrolidine-1,2-dicarboxylic acid 1-tert-butyl ester 2-methyl ester (4.25 g) in dry diethyl ether (20 mL) over 10 minutes. The reaction was stirred at −20° C. for 20 minutes and followed by TLC. After 30 minutes the reaction was quenched at −20° C. by adding saturated aqueous sodium sulfate solution dropwise until the lithium aluminium hydride reagent was fully quenched. Further solid sodium sulfate was added to the slurry and the mixture was allowed to warm to ambient temperature. The slurry was filtered and the solid was washed with further diethyl ether. The filtrate was collected and the diethyl ether was evaporated in vacuo to afford the desired 2-(4-fluoro-phenyl)-2-hydroxymethyl-pyrrolidine-1-carboxylic acid tert-butyl ester (3.37 g, MS (ES+): 296.3 (MH$^+$)) as a colourless oil.

Step G] 2-(4-Fluoro-phenyl)-2-formyl-pyrrolidine-1-carboxylic Acid Tert-butyl Ester To 2-(4-fluoro-phenyl)-2-hydroxymethyl-pyrrolidine-1-carboxylic acid tert-butyl ester (3.9 g) in a round bottom flask was added Dess-Martin periodinane solution (47 mL of a 15% solution in DCM, CAS [87413-09-0]) and the reaction mixture was stirred for 5 hours at RT. The reaction mixture was then quenched with saturated aqueous sodium thiosulfate solution (25 mL) and stirred a further 20 minutes. The phases were separated and the aqueous was extracted with further DCM (25 mL). The combined organic phases were washed with saturated sodium bicarbonate solution and dried over sodium sulfate. Filtration of the drying agent and evaporation of the volatiles in vacuo afforded the desired 2-(4-fluoro-phenyl)-2-formyl-pyrrolidine-1-carboxylic acid tert-butyl ester (4.13 g, MS (ES+): 294.1 (MH$^+$)) as a brown solid which was taken into the next step without further purification.

Step H] 2-(4-Fluoro-phenyl)-2-[((E)-5-hydroxy-adamantan-2-ylamino)-methyl]-pyrrolidine-1-carboxylic Acid Tert-butyl Ester To a solution of 2-(4-fluoro-phenyl)-2-formyl-pyrrolidine-1-carboxylic acid tert-butyl ester (200 mg) in EtOH (3 mL) was added (E)-4-amino-adamantan-1-ol (86 mg) and the reaction mixture was heated to 80° C. for 7 hours. The mixture was then cooled to 0° C. and sodium borohydride (31 mg) was added. The reaction was then stirred overnight and then quenched with water (25 mL) and diluted with chloroform (25 mL). The phases were separated and the aqueous phase was extracted with further chloroform (3×25 mL) and the combined organic phases were washed with saturated aqueous sodium bicarbonate solution (5 mL) and dried over sodium sulfate. Filtration and evaporation of the volatiles in vacuo afforded the desired 2-(4-fluoro-phenyl)-2-[((E)-5-hydroxy-adamantan-2-ylamino)-methyl]-pyrrolidine-1-carboxylic acid tert-butyl ester (266 mg, MS (ES+): 445.2 (MH$^+$)) as ab rown gum. This material was taken into the next step without further purification.

Step I] (E)-4-{[2-(4-Fluoro-phenyl)-pyrrolidin-2-ylmethyl]-amino}-adamantan-1-ol This material was obtained in analogy to example 1, step B, using 2-(4-fluoro-phenyl)-2-[((E)-5-hydroxy-adamantan-2-ylamino)-methyl]-pyrrolidine-1-carboxylic acid tert-butyl ester (1.2 g), to give (E)-4-{[2-(4-Fluoro-phenyl)-pyrrolidin-2-ylmethyl]-amino}-adamantan-1-ol (950 mg, MS (ES+): 345.2 (M+H)) as a brown solid.

Step J] (rac)-7a-(4-Fluoro-phenyl)-2-((E)-5-hydroxy-adamantan-2-yl)-hexahydro-pyrrolo[1,2-c]imidazol-3-one This material was obtained in analogy to example 1, step D, using (E)-4-{[2-(4-fluoro-phenyl)-pyrrolidin-2-ylmethyl]-amino}-adamantan-1-ol (1.1 g), to give after flash column chromatography over silica gel (eluent 80% EtOAc in heptane to 100% EtOAc) the desired (rac)-7a-(4-fluoro-phenyl)-2-((E)-5-hydroxy-adamantan-2-yl)-hexahydro-pyrrolo[1,2-c]imidazol-3-one (574 mg, MS (ES+): 371.2 (M+H)) as an off white solid.

Example 87

(rac)-7a-(2,4-Dichloro-phenyl)-2-((E)-5-hydroxy-adamantan-2-yl)-hexahydro-pyrrolo[1,2-c]imidazol-3-one This material was obtained in analogy to example 86 (step A-I) using (2,4-dichloro-phenyl)-acetic acid ethyl ester (step A), to give after step I the desired (rac)-7a-(2,4-dichloro-phenyl)-2-((E)-5-hydroxy-adamantan-2-yl)-hexahydro-pyr-rolo[1,2-c]imidazol-3-one (46 mg, MS (ES+): 421.0 (MH$^+$)) as a white solid.

Example 88

(E)-4-[(rac)-7a-(4-Fluoro-phenyl)-3-oxo-tetrahydro-pyrrolo[1,2-c]imidazol-2-yl]-adamantane-1-carboxy-lic Acid Amide Step A] (rac)-2-(4-Fluoro-phenyl)-2-[((E)-5-meth-oxycarbonyl-adamantan-2-ylamino)-methyl]-pyrroli-dine-1-carboxylic Acid Tert-butyl Ester A solution of 2-(4-fluoro-phenyl)-2-formyl-pyrrolidine-1-carboxylic acid tert-butyl ester (200 mg, example 86, step G) and (E)-4-amino-adamantane-1-carboxylic acid methyl ester hydrochloride salt (107 mg, CAS: 898265-48-0) in EtOH (5 mL) was heated to reflux for 18 h. The solution as then cooled to 0° C. and sodium borohydride (31 mg) was added. The resulting mixture was stirred a further 1.5 hours. The reaction was quenched with water and diluted with chloroform and separated. The aqueous phase was extracted with further chloroform and the combined organics were washed with aqueous sodium bicarbonate solution and dried over sodium sulfate. Filtration and evaporation to dryness in vacuo afforded the desired (rac)-2-(4-fluoro-phenyl)-2-[((E)-5-methoxycarbonyl-adamantan-2-ylamino)-methyl]-pyrroli-dine-1-carboxylic acid tert-butyl ester (318 mg, MS (ES+): 487.2 (MH$^+$)) as a brown solid. The compound was taken into the next step without further purification.

Step B] (E)-4-{[(rac)-2-(4-Fluoro-phenyl)-pyrroli-din-2-ylmethyl]-amino}-adamantane-1-carboxylic acid methyl ester This material was obtained in analogy to example 8, step B, using (rac)-2-(4-fluoro-phenyl)-2-[((E)-5-methoxycarbonyl-adamantan-2-ylamino)-methyl]-pyrrolidine-1-carboxylic acid tert-butyl ester (318 mg) to give the desired (E)-4-{[(rac)-2-(4-fluoro-phenyl)-pyrrolidin-2-ylmethyl]-amino}-adamantane-1-carboxylic acid methyl ester (205 mg, MS (ES+): 387.5 (MH$^+$)) as a brown solid.

Step C] (E)-4-[(rac)-7a-(4-Fluoro-phenyl)-3-oxo-tetrahydro-pyrrolo[1,2-c]imidazol-2-yl]-adamantane-1-carboxylic acid methyl ester This material was obtained in analogy to example 1, step D, using (E)-4-{[(R)-2-(4-fluoro-phenyl)-pyrrolidin-2-ylm-ethyl]-amino}-adamantane-1-carboxylic acid methyl ester (205 mg) to give after flash column chromatography over silica gel (90% EtOAc/Heptane) the desired (E)-4-[(rac)-7a-(4-fluoro-phenyl)-3-oxo-tetrahydro-pyrrolo[1,2-c]imidazol-2-yl]-adamantane-1-carboxylic acid methyl ester (33 mg, MS (ES+): 413.3 (MH$^+$)) as a light brown solid.

Step D] (E)-4-[(rac)-7a-(4-Fluoro-phenyl)-3-oxo-tetrahydro-pyrrolo[1,2-c]imidazol-2-yl]-adamantane-1-carboxylic Acid This material was obtained in analogy to example 11, using (E)-4-[(rac)-7a-(4-Fluoro-phenyl)-3-oxo-tetrahydro-pyrrolo [1,2-c]imidazol-2-yl]-adamantane-1-carboxylic acid methyl ester (33 mg) to give the desired (E)-4-[(rac)-7a-(4-fluoro-phenyl)-3-oxo-tetrahydro-pyrrolo[1,2-c]imidazol-2-yl]-ada-mantane-1-carboxylic acid (29 mg, MS (ES+): 399.3 (MH$^+$)) as a light brown solid.

Step E] (E)-4-[(rac)-7a-(4-Fluoro-phenyl)-3-oxo-tetrahydro-pyrrolo[1,2-c]imidazol-2-yl]-adamantane-1-carboxylic Acid Amide To a solution of (E)-4-[(rac)-7a-(4-fluoro-phenyl)-3-oxo-tetrahydro-pyrrolo[1,2-c]imidazol-2-yl]-adamantane-1-car-boxylic acid (30 mg) in dry THF (0.5 mL) was added at −10° C. triethylamine (10 μL) followed by ethylchloroformate (10 μL) and the reaction mixture was stirred for 1.5 hours at −10° C. To this was then added 7 μL of ammonia solution (25% ammonia solution in water) and the reaction mixture was allowed to warm to RT and stirred for a further 2.5 hours. The reaction was diluted with saturated aqueous sodium bicar-bonate solution and EtOAc and the phases were separated. The aqueous phase was extracted with further EtOAc and the combined organic phases were washed with 0.5 N aqueous HCl solution, brine and dried over sodium sulfate. Filtration of the drying agent and evaporation to dryness in vacuo afforded a crude residue which was purified via flash column chromatography over silica gel (eluent EtOAc followed by 5% MeOH in DCM) to give the desired (E)-4-[(rac)-7a-(4-fluoro-phenyl)-3-oxo-tetrahydro-pyrrolo[1,2-c]imidazol-2-yl]-adamantane-1-carboxylic acid amide (18 mg, MS (ES+): 398.3 (M+H)) as a white solid.

Examples 89 and 90

(Z)-4-((rac)-7a-cyclopropylmethyl-3-oxo-tetrahydro-pyrrolo[1,2-c]imidazol-2-yl)-adamantane-1-carboxy-lic Acid Amide (89) and (E)-4-((rac)-7a-cyclopropyl-methyl-3-oxo-tetrahydro-pyrrolo[1,2-c]imidazol-2-yl)-adamantane-1-carboxylic Acid Amide (90)

Part A] (E/Z)-4-(7a-Cyclopropylmethyl-3-oxo-tet-rahydro-pyrrolo[1,2-c]imidazol-2-yl)-adamantane-1-carboxylic Acid Methyl Ester This material was obtained in analogy to example 47 (step A-E) using 2-cyclopropylmethyl-pyrrolidine-1,2-dicarboxy-lic acid 1-tert-butyl ester in step A (made from bromoethyl-cyclopropane and BOC-L-proline in analogy to example 12, step A), to give (E/Z)-4-((rac)-7a-cyclopropylmethyl-3-oxo-tetrahydro-pyrrolo[1,2-c]imidazol-2-yl)-adamantane-1-car-boxylic acid methyl ester (102 mg, MS (ES+): 373.3 (MH$^+$)) as a yellow solid.

Part B] (E/Z)-4-((rac)-7a-Cyclopropylmethyl-3-oxo-tetrahydro-pyrrolo[1,2-c]imidazol-2-yl)-adamantane-1-carboxylic Acid To a solution of (E/Z)-4-((rac)-7a-cyclopropylmethyl-3-oxo-tetrahydro-pyrrolo[1,2-c]imidazol-2-yl)-adamantane-1-carboxylic acid methyl ester (98 mg) in MeOH (3 mL) was added 1N NaOH (3.0 ml) and the reaction mixture was stirred at 40° C. for 5 hours. The reaction mixture was diluted with EtOAc and acidified with HCl (10 ml of 1N aqueous solution) and the phases were separated. The aqueous phase was extracted with further EtOAc and the combined organic phases were washed with brine, dried over sodium sulfate, filtered and reduced in vacuo to dryness to afford the desired (E/Z)-4-((rac)-7a-cyclopropylmethyl-3-oxo-tetrahydro-pyrrolo[1,2-c]imidazol-2-yl)-adamantane-1-carboxylic acid (92 mg, MS (ES−): 357.4 (M−H)) as a light brown gum.

Part C] (Z)-4-((rac)-7a-cyclopropylmethyl-3-oxo-tetrahydro-pyrrolo[1,2-c]imidazol-2-yl)-adamantane-1-carboxylic acid amide and (E)-4-((rac)-7a-cyclopropylmethyl-3-oxo-tetrahydro-pyrrolo[1,2-c]imidazol-2-yl)-adamantane-1-carboxylic Acid Amide These materials were prepared in analogy to example 16 using (E/Z)-4-((rac)-7a-cyclopropylmethyl-3-oxo-tetrahydro-pyrrolo[1,2-c]imidazol-2-yl)-adamantane-1-carboxylic acid (92 mg), to give after chromatographic separation of the E an Z isomer over silica gel (EtOAc/heptane) the desired (Z)-4-((rac)-7a-cyclopropylmethyl-3-oxo-tetrahydro-pyrrolo[1,2-c]imidazol-2-yl)-adamantane-1-carboxylic acid amide (17 mg, MS (ES+): 357.3 (M+H), white solid) and (E)-4-((rac)-7a-cyclopropylmethyl-3-oxo-tetrahydro-pyrrolo[1,2-c]imidazol-2-yl)-adamantane-1-carboxylic acid amide (22 mg, MS (ES+): 357.3 (M+H), white solid).

Example 91

4-[(rac)-7a-(4-Fluoro-phenyl)-3-oxo-tetrahydro-pyrrolo[1,2-c]imidazol-2-yl]-bicyclo[2.2.2]octane-1-carboxylic Acid Amide Thismaterial was prepared in analogy to example 88 (step A-E) using 2-(4-fluoro-phenyl)-2-formyl-pyrrolidine-1-carboxylic acid tert-butyl ester (300 mg) and known compound 4-amino-bicyclo[2.2.2]octane-1-carboxylic acid methyl ester, hydrochloride salt (CAS135908-43-9) in step A, to give after step E the desired 4-[(rac)-7a-(4-fluoro-phenyl)-3-oxo-tetrahydro-pyrrolo[1,2-c]imidazol-2-yl]-bicyclo[2.2.2]octane-1-carboxylic acid amide (9 mg, MS (ES+): 372.3 (M+H), beige solid).

Examples 92 and 93

(S)-7a-(4-Fluoro-phenyl)-2-((E)-5-hydroxy-adamantan-2-yl)-hexahydro-pyrrolo[1,2-c]imidazol-3-one and (R)-7a-(4-Fluoro-phenyl)-2-((E)-5-hydroxy-adamantan-2-yl)-hexahydro-pyrrolo[1,2-c]imidazol-3-one (rac)-7a-(4-Fluoro-phenyl)-2-((E)-5-hydroxy-adamantan-2-yl)-hexahydro-pyrrolo[1,2-c]imidazol-3-one (288 mg, example 86) was separated into both enantiomers using chiral HPLC on Chiralpak AD, using 20% isopropanol/heptane as eluent and UV detection (220 nm) to give (S)-7a-(4-Fluoro-phenyl)-2-((E)-5-hydroxy-adamantan-2-yl)-hexahydro-pyrrolo[1,2-c]imidazol-3-one (98 mg, (−) enantiomer, MS (ES+): 371.2 (MH+), white solid) and (R)-7a-(4-Fluoro-phenyl)-2-((E)-5-hydroxy-adamantan-2-yl)-hexahydro-pyrrolo[1,2-c]imidazol-3-one (95 mg, (+) enantiomer, MS (ES+): 371.2 (MH+), white solid).

Examples 94 and 95

(rac)-7a-(2,4-Difluoro-phenyl)-2-((Z)-5-hydroxy-adamantan-2-yl)-hexahydro-pyrrolo[1,2-c]imidazol-3-one and (rac)-7a-(2,4-Difluoro-phenyl)-2-((E)-5-hydroxy-adamantan-2-yl)-hexahydro-pyrrolo[1,2-c]imidazol-3-one These materials were obtained in analogy to example 86 (step A-I) using (2,4-difluoro-phenyl)-acetic acid ethylester (step A), and (E/Z)-4-amino-adamantan-1-ol (step H) to give after step I the desired (rac)-7a-(2,4-difluoro-phenyl)-2-((Z)-5-hydroxy-adamantan-2-yl)-hexahydro-pyrrolo[1,2-c]imidazol-3-one (42 mg, MS (ES+): 389.3 (MH+), white solid) and (rac)-7a-(2,4-difluoro-phenyl)-2-((Z)-5-hydroxy-adamantan-2-yl)-hexahydro-pyrrolo[1,2-c]imidazol-3-one (55 mg, MS (ES+): 389.3 (MH+), white solid).

Examples 96 and 97

(rac)-2-((Z)-5-Hydroxy-adamantan-2-yl)-7a-(3-methoxy-phenyl)-hexahydro-pyrrolo[1,2-c]imidazol-3-one and (rac)-2-((E)-5-Hydroxy-adamantan-2-yl)-7a-(3-methoxy-phenyl)-hexahydro-pyrrolo[1,2-c]imidazol-3-one These materials were obtained in analogy to example 86 (step A-I) using (3-Methoxy-phenyl)-acetic acid ethyl ester (step A), and (E/Z)-4-amino-adamantan-1-ol (step H) to give after step I the desired (rac)-2-((Z)-5-Hydroxy-adamantan-2-yl)-7a-(3-methoxy-phenyl)-hexahydro-pyrrolo[1,2-c]imidazol-3-one (14 mg, MS (ES+): 383.3 (MH+), white solid) and (rac)-2-((E)-5-Hydroxy-adamantan-2-yl)-7a-(3-methoxy-phenyl)-hexahydro-pyrrolo[1,2-c]imidazol-3-one (8 mg, MS (ES+): 383.3 (MH+), white solid).

Example 98

4-[(rac)-7a-(3-Chloro-phenyl)-3-oxo-tetrahydro-pyrrolo[1,2-c]imidazol-2-yl]-bicyclo[2.2.2]octane-1-carboxylic Acid Amide This material was prepared in analogy to example 88 (step A-E) using 2-(3-chloro-phenyl)-2-formyl-pyrrolidine-1-carboxylic acid tert-butyl ester (300 mg, see example 85 and 86) and known compound 4-amino-bicyclo[2.2.2]octane-1-carboxylic acid methyl ester, hydrochloride salt (CAS135908-43-9) in example 88 step A, to give after step E the desired 4-[(rac)-7a-(3-chloro-phenyl)-3-oxo-tetrahydro-pyrrolo[1,2-c]imidazol-2-yl]-bicyclo[2.2.2]octane-1-carboxylic acid amide (142 mg, MS (ES+): 388.3 (M+H), beige solid).

Examples 99 and 100

4-[(S)-7a-(3-Chloro-phenyl)-3-oxo-tetrahydro-pyrrolo[1,2-c]imidazol-2-yl]-bicyclo[2.2.2]octane-1-carboxylic Acid Amide and 4-[(R)-7a-(3-chloro-phenyl)-3-oxo-tetrahydro-pyrrolo[1,2-c]imidazol-2-yl]-bicyclo[2.2.2]octane-1-carboxylic Acid Amide 4-[(rac)-7a-(3-chloro-phenyl)-3-oxo-tetrahydro-pyrrolo[1,2-c]imidazol-2-yl]-bicyclo[2.2.2]octane-1-carboxylic acid amide (142 mg, example 98) was separated into both enantiomers using chiral HPLC on Chiralpak AD, using 20% isopropanol/heptane as eluent and UV detection (220 nm) to give 4-[(S)-7a-(3-chloro-phenyl)-3-oxo-tetrahydro-pyrrolo[1,2-c]imidazol-2-yl]-bicyclo[2.2.2]octane-1-carboxylic acid amide (56 mg, (+) enantiomer, MS (ES+): 388.3 (MH+), white solid) and 4-[(R)-7a-(3-chloro-phenyl)-3-oxo-tetrahydro-pyrrolo[1,2-c]imidazol-2-yl]-bicyclo[2.2.2]octane-1-carboxylic acid amide (47 mg, (−) enantiomer, MS (ES+): 388.3 (MH+), white solid).

Example 101

4-((rac)-7a-Cyclopropylmethyl-3-oxo-tetrahydro-pyrrolo[1,2-c]imidazol-2-yl)-bicyclo [2.2.2]octane-1-carboxylic Acid Amide Part A] (rac)-2-Cyclopropylmethyl-2-formyl-pyrrolidine-1-carboxylic Acid Tert-butyl Ester To a solution of 2-cyclopropylmethyl-pyrrolidine-1,2-dicarboxylic acid 1-tert-butyl ester (4 g, see example 64 and 65) in THF (100 mL) was added borane-methylsulfide complex (8.9 mL of a 2M solution in THF) dropwise via syringe. The reaction mixture was heated for 4 hours to 80° C. and was then cooled to RT. The THF was removed in vacuo and the residue was then diluted with water and DCM. The phases were separated and the aqueous phase was extracted with further DCM (2×50 mL). The combined organic layers were washed with saturated aqueous sodium bicarbonate solution, brine and dried over sodium sulfate. Filtration of the drying agent and evaporation in vacuo to dryness afforded the crude 2-cyclopropylmethyl-2-hydroxymethyl-pyrrolidine-1-carboxylic acid tert-butyl ester (3.7 g) to which was added Dess-Martin periodinane solution (32.6 mL of a 15% solution in DCM, CAS [87413-09-0]) and the reaction mixture was stirred for 5 hours at RT. The reaction was quenched with 10 mL of saturated aqueous sodium thiosulfate solution and stirred for a further 20 minutes. The phases were separated and the DCM layer was washed with saturate aqueous sodium bicarbonate solution. The aqueous layers were back extracted with further DCM and the combined DCM layers were dried over sodium sulfate, filtered and reduced to dryness in vacuo to afford the desired 2-cyclopropylmethyl-2-formyl-pyrrolidine-1-carboxylic acid tert-butyl ester (2.59 g, MS (ES+): 254.3 (M+H), as a brown oil).

Part B] 4-((rac)-7a-Cyclopropylmethyl-3-oxo-tetrahydro-pyrrolo[1,2-c]imidazol-2-yl)-bicyclo[2.2.2]octane-1-carboxylic acid amide This material was prepared in analogy to example 88 (step A-E) using 2-cyclopropylmethyl-2-formyl-pyrrolidine-1-carboxylic acid tert-butyl ester (1.6 g) and known compound 4-amino-bicyclo[2.2.2]octane-1-carboxylic acid methyl ester (1.41 g), to give after step E the desired 4-((rac)-7a-cyclopropylmethyl-3-oxo-tetrahydro-pyrrolo[1,2-c]imidazol-2-yl)-bicyclo[2.2.2]octane-1-carboxylic acid amide (448 mg, MS (ES+): 332.3 (M+H), light yellow solid).

Examples 102 and 103

4-((S)-7a-Cyclopropylmethyl-3-oxo-tetrahydro-pyrrolo[1,2-c]imidazol-2-yl)-bicyclo [2.2.2]octane-1-carboxylic Acid Amide and 4-((R)-7a-Cyclopropylmethyl-3-oxo-tetrahydro-pyrrolo[1,2-c]imidazol-2-yl)-bicyclo[2.2.2]octane-1-carboxylic Acid Amide (rac)-4-(7a-Cyclopropylmethyl-3-oxo-tetrahydro-pyrrolo[1,2-c]imidazol-2-yl)-bicyclo[2.2.2]octane-1-carboxylic acid amide (430 mg, example 101) was separated into both enantiomers using chiral HPLC on Chiralpak AD, using 15% isopropanol/heptane as eluent and UV detection (220 nm) to give 4-((S)-7a-cyclopropylmethyl-3-oxo-tetrahydro-pyrrolo[1,2-c]imidazol-2-yl)-bicyclo[2.2.2]octane-1-carboxylic acid amide (150 mg, (+) enantiomer, MS (ES+): 332.3 (MH+), white solid) and 4-((R)-7a-Cyclopropylmethyl-3-oxo-tetrahydro-pyrrolo[1,2-c]imidazol-2-yl)-bicyclo[2.2.2]octane-1-carboxylic acid amide (145 mg, (−) enantiomer, MS (ES+): 332.3 (MH+), white solid).

Example A

A compound of formula I can be used in a manner known per se as the active ingredient for the production of tablets of the following composition:

| Per tablet | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula I can be used in a manner known per se as the active ingredient for the production of capsules of the following composition:

| Per capsule | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

It is understood that the invention is not limited to the particular embodiments of the invention described above, as variations of the particular embodiments may be made and still fall within the scope of the appended claims.

What is claimed is:

1. A compound according to formula (I):

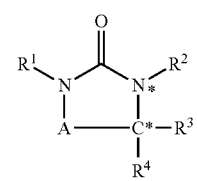

wherein:

R¹ is hydroxy-adamantyl, methoxycarbonyl-adamantyl, carboxy-adamantyl, aminocarbonyl-adamantyl, aminocarbonyl-bicyclo[2.2.2]octanyl, cholro-benzyl, benzyl, chlorophenylethyl, phenylethyl, difluorobenzyl, dichlorophenyl, trifluoromethylphenyl or difluorophenylethyl;

R² and R³ together with the nitrogen atom N* and the carbon atom C* to which they are attached form

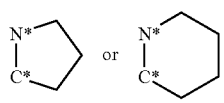

R⁴ is hydrogen, alkyl, cycloalkyl, cycloalkylalkyl, alkoxyalkyl, arylalkyl, arylalkoxy, arylalkoxyalkyl, hydroxyalkyl, aryl, heteroarylalkyl, heteroaryloxyalkyl, substituted aryl, substituted heteroarylalkyl or substituted heteroaryloxyalkyl, wherein substituted aryl, substituted heteroarylalkyl and substituted heteroaryloxyalkyl are substituted with one to three substituents independently selected from alkyl, cycloalkyl, cyano, halogen, haloalkyl, hydroxy or alkoxy;

R⁵ is hydrogen;

R⁶ is hydrogen; and

A is CR⁵R⁶;

or a pharmaceutically acceptable salt thereof.

2. The compound according to claim 1, wherein R⁴ is alkyl, cycloalkylalkyl, alkoxyalkyl, phenylalkyl, phenylalkoxy, phenylalkoxyalkyl, hydroxyalkyl, pyridinylalkyl, pyridinyloxyalkyl, substituted phenyl, substituted pyridinylalkyl or substituted pyridinyloxyalkyl, wherein substituted phenyl, substituted pyridinylalkyl and substituted pyridinyloxyalkyl are substituted with one to three substituents independently selected from, cyano, halogen, haloalkyl and alkoxy.

3. The compound according to claim 1, wherein R⁴ is methyl, benzyloxymethyl, benzyl, cyanopyridinyloxymethyl, hydroxymethyl, trifluoromethylpyridinyloxymethyl, methoxymethyl, difluorobenzyloxymethyl, phenyl, phenethyl, cyclopropylmethyl, chlorophenyl, fluorophenyl, chlorophenyl, dichlorophenyl, difluorophenyl or methoxyphenyl.

4. The compound according to claim 1, wherein R⁴ is methyl, cyanopyridinyloxymethyl, cyclopropylmethyl, fluorophenyl or chlorophenyl.

5. The compound according to claim 1 selected from:
(S)-2-((Z)-5-Hydroxy-adamantan-2-yl)-7a-methyl-hexahydro-pyrrolo[1,2-c]imidazol-3-one;
(S)-2-((E)-5-Hydroxy-adamantan-2-yl)-7a-methyl-hexahydro-pyrrolo[1,2-c]imidazol-3-one;
(S)-2-((Z)-5-Hydroxy-adamantan-2-yl)-hexahydro-pyrrolo[1,2-c]imidazol-3-one;
(S)-2-((E)-5-Hydroxy-adamantan-2-yl)-hexahydro-pyrrolo[1,2-c]imidazol-3-one;
(S)-2-Phenyl-hexahydro-pyrrolo[1,2-c]imidazol-3-one;
(S)-2-((Z)-5-Hydroxy-adamantan-2-yl)-hexahydro-imidazo[1,5-a]pyridin-3-one;
(S)-2-((E)-5-Hydroxy-adamantan-2-yl)-hexahydro-imidazo[1,5-a]pyridin-3-one;
(rac)-(E/Z)-4-(3-Oxo-tetrahydro-pyrrolo[1,2-c]imidazol-2-yl)-adamantane-1-carboxylic acid methyl ester;
(rac)-(E/Z)-4-(3-Oxo-tetrahydro-pyrrolo[1,2-c]imidazol-2-yl)-adamantane-1-carboxylic acid;
(rac)-7a-Benzyloxymethyl-2-((E/Z)-5-hydroxy-adamantan-2-yl)-hexahydro-pyrrolo[1,2-c]imidazol-3-one;
(R)-7a-Benzyl-2-((Z)-5-hydroxy-adamantan-2-yl)-hexahydro-pyrrolo[1,2-c]imidazol-3-one;
(R)-7a-Benzyl-2-((E)-5-hydroxy-adamantan-2-yl)-hexahydro-pyrrolo[1,2-c]imidazol-3-one;
(R)-7a-Benzyl-2-((E/Z)-5-hydroxy-adamantan-2-yl)-tetrahydro-pyrrolo[1,2-c]imidazole-1,3-dione;
(E)-4-((S)-3-Oxo-tetrahydro-pyrrolo[1,2-c]imidazol-2-yl)-adamantane-1-carboxylic acid amide;
(rac)-2-((E/Z)-5-Hydroxy-adamantan-2-yl)-7a-hydroxymethyl-hexahydro-pyrrolo[1,2-c]imidazol-3-one; and
(rac)-6-[2-((E/Z)-5-Hydroxy-adamantan-2-yl)-3-oxo-tetrahydro-pyrrolo[1,2-c]imidazol-7a-ylmethoxy]-nicotinonitrile.

6. The compound according to claim 1, selected from:
(R)-2-((Z)-5-Hydroxy-adamantan-2-yl)-hexahydro-pyrrolo[1,2-c]imidazol-3-one;
(R)-2-((E)-5-Hydroxy-adamantan-2-yl)-hexahydro-pyrrolo[1,2-c]imidazol-3-one;
(rac)-2-((E/Z)-5-Hydroxy-adamantan-2-yl)-hexahydro-imidazo[5,1-c][1,4]oxazin-3-one;
(rac)-2-((E)-5-Hydroxy-adamantan-2-yl)-7a-hydroxymethyl-hexahydro-pyrrolo[1,2-c]imidazol-3-one;
(rac)-2-((Z)-5-Hydroxy-adamantan-2-yl)-8a-methyl-hexahydro-imidazo[1,5-a]pyridin-3-one;
(rac)-2-((E)-5-Hydroxy-adamantan-2-yl)-8a-methyl-hexahydro-imidazo[1,5-a]pyridin-3-one;
6-[(rac)-2-((E)-5-Hydroxy-adamantan-2-yl)-3-oxo-tetrahydro-pyrrolo[1,2-c]imidazol-7a-ylmethoxy]-nicotinonitrile;
(rac)-2-((Z)-5-Hydroxy-adamantan-2-yl)-7a-(5-trifluoromethyl-pyridin-2-yloxymethyl)-hexahydro-pyrrolo[1,2-c]imidazol-3-one;
(rac)-2-((E)-5-Hydroxy-adamantan-2-yl)-7a-(5-trifluoromethyl-pyridin-2-yloxymethyl)-hexahydro-pyrrolo[1,2-c]imidazol-3-one;
(6R,7aS)-6-Benzyloxy-2-((Z)-5-hydroxy-adamantan-2-yl)-hexahydro-pyrrolo[1,2-c]imidazol-3-one;
(6R,7aS)-6-Benzyloxy-2-((E)-5-hydroxy-adamantan-2-yl)-hexahydro-pyrrolo[1,2-c]imidazol-3-one;
(6R,7aS)-6-Hydroxy-2-((E)-5-hydroxy-adamantan-2-yl)-hexahydro-pyrrolo[1,2-c]imidazol-3-one;
(rac)-2-(E/Z)-5-Hydroxy-adamantan-2-yl)-7a-methoxymethyl-hexahydro-pyrrolo[1,2-c]imidazol-3-one;
(rac)-7a-(2,4-Difluoro-benzyloxymethyl)-2-((E)-5-hydroxy-adamantan-2-yl)-hexahydro-pyrrolo[1,2-c]imidazol-3-one;
(S)-2-((E)-5-Hydroxy-adamantan-2-yl)-8a-methyl-hexahydro-imidazo[1,5-a]pyridin-3-one;
(R)-2-((E)-5-Hydroxy-adamantan-2-yl)-8a-methyl-hexahydro-imidazo[1,5-a]pyridin-3-one; and
(S)-2-((E)-5-Hydroxy-adamantan-2-yl)-7a-hydroxymethyl-hexahydro-pyrrolo[1,2-c]imidazol-3-one.

7. The compound according to claim 1, selected from:
(R)-2-((E)-5-Hydroxy-adamantan-2-yl)-7a-hydroxymethyl-hexahydro-pyrrolo[1,2-c]imidazol-3-one;
(rac)-2-((Z)-5-Hydroxy-adamantan-2-yl)-7a-phenyl-hexahydro-pyrrolo[1,2-c]imidazol-3-one;
(rac)-2-((E)-5-Hydroxy-adamantan-2-yl)-7a-phenyl-hexahydro-pyrrolo[1,2-c]imidazol-3-one;
6-[(S)-2-((E)-5-Hydroxy-adamantan-2-yl)-3-oxo-tetrahydro-pyrrolo[1,2-c]imidazol-7a-ylmethoxy]-nicotinonitrile;
N-{(E)-4-[(R)-7a-(4-Fluoro-phenyl)-3-oxo-tetrahydro-pyrrolo[1,2-c]imidazol-2-yl]-adamantan-1-yl}-acetamide;
(rac)-8a-Benzyloxymethyl-2-((Z)-5-hydroxy-adamantan-2-yl)-hexahydro-imidazo[1,5-a]pyridin-3-one;
(rac)-8a-Benzyloxymethyl-2-((E)-5-hydroxy-adamantan-2-yl)-hexahydro-imidazo[1,5-a]pyridin-3-one;
(E/Z)-4-((rac)-7a-Benzyloxymethyl-3-oxo-tetrahydro-pyrrolo[1,2-c]imidazol-2-yl)-adamantane-1-carboxylic acid methyl ester;
(R)-2-((Z)-5-Hydroxy-adamantan-2-yl)-7a-phenethyl-hexahydro-pyrrolo[1,2-c]imidazol-3-one;

(R)-2-((E)-5-Hydroxy-adamantan-2-yl)-7a-phenethyl-hexahydro-pyrrolo[1,2-c]imidazol-3-one;

(rac)-2-(2-Chloro-benzyl)-7a-methyl-hexahydro-pyrrolo[1,2-c]imidazol-3-one;

(rac)-2-Benzyl-7a-methyl-hexahydro-pyrrolo[1,2-c]imidazol-3-one;

(E/Z)-4-((rac)-7a-Hydroxymethyl-3-oxo-tetrahydro-pyrrolo[1,2-c]imidazol-2-yl)-adamantane-1-carboxylic acid methyl ester;

(E/Z)-4-((rac)-7a-Benzyloxymethyl-3-oxo-tetrahydro-pyrrolo[1,2-c]imidazol-2-yl)-adamantane-1-carboxylic acid;

(S)-6,6-Difluoro-2-((Z)-5-hydroxy-adamantan-2-yl)-hexahydro-pyrrolo[1,2-c]imidazol-3-one;

(S)-6,6-Difluoro-2-((E)-5-hydroxy-adamantan-2-yl)-hexahydro-pyrrolo[1,2-c]imidazol-3-one;

(E/Z)-4-[(rac)-7a-(5-Cyano-pyridin-2-yloxymethyl)-3-oxo-tetrahydro-pyrrolo[1,2-c]imidazol-2-yl]-adamantane-1-carboxylic acid methyl ester; and (6R,7aS)-6-(2,4-Difluoro-benzyloxy)-2-((E)-5-hydroxy-adamantan-2-yl)-hexahydro-pyrrolo[1,2-c]imidazol-3-one.

8. The compound according to claim 1, selected from:

6-[(rac)-2-((E)-5-Hydroxy-adamantan-2-yl)-3-oxo-hexahydro-imidazo[1,5-a]pyridin-8a-ylmethoxy]-nicotinonitrile;

(rac)-2-[1-(4-Chloro-phenyl)-ethyl]-7a-methyl-hexahydro-pyrrolo[1,2-c]imidazol-3-one;

(rac)-2-(3-Chloro-benzyl)-7a-methyl-hexahydro-pyrrolo[1,2-c]imidazol-3-one;

(rac)-7a-Methyl-2-(1-phenyl-ethyl)-hexahydro-pyrrolo[1,2-c]imidazol-3-one;

(E/Z)-4-((rac)-7a-Benzyloxymethyl-3-oxo-tetrahydro-pyrrolo[1,2-c]imidazol-2-yl)-adamantane-1-carboxylic acid amide;

(E/Z)-4-[(rac)-7a-(5-Cyano-pyridin-2-yloxymethyl)-3-oxo-tetrahydro-pyrrolo[1,2-c]imidazol-2-yl]-adamantane-1-carboxylic acid amide;

(rac)-7a-Cyclopropylmethyl-2-((Z)-5-hydroxy-adamantan-2-yl)-hexahydro-pyrrolo[1,2-c]imidazol-3-one;

(rac)-7a-Cyclopropylmethyl-2-((E)-5-hydroxy-adamantan-2-yl)-hexahydro-pyrrolo[1,2-c]imidazol-3-one;

(rac)-6,6-Difluoro-2-((Z)-5-hydroxy-adamantan-2-yl)-7a-methyl-hexahydro-pyrrolo[1,2-c]imidazol-3-one;

(rac)-7a-(4-Chloro-phenyl)-2-((E)-5-hydroxy-adamantan-2-yl)-hexahydro-pyrrolo[1,2-c]imidazol-3-one;

(rac)-2-(3-Chloro-phenyl)-7a-methyl-hexahydro-pyrrolo[1,2-c]imidazol-3-one;

(rac)-2-((E/Z)-5-Methanesulfonyl-adamantan-2-yl)-7a-phenyl-hexahydro-pyrrolo[1,2-c]imidazol-3-one;

(rac)-2-(2,4-Difluoro-benzyl)-7a-methyl-hexahydro-pyrrolo[1,2-c]imidazol-3-one;

(rac)-2-(2-Chloro-phenyl)-7a-methyl-hexahydro-pyrrolo[1,2-c]imidazol-3-one;

(rac)-2-(4-Chloro-benzyl)-7a-methyl-hexahydro-pyrrolo[1,2-c]imidazol-3-one;

(rac)-2-(2,4-Dichloro-phenyl)-7a-methyl-hexahydro-pyrrolo[1,2-c]imidazol-3-one;

(rac)-6,6-Difluoro-2-((E)-5-hydroxy-adamantan-2-yl)-7a-methyl-hexahydro-pyrrolo[1,2-c]imidazol-3-one;

(S)-2-(3-Chloro-phenyl)-6,6-difluoro-hexahydro-pyrrolo[1,2-c]imidazol-3-one;

(rac)-7a-Methyl-2-(2-trifluoromethyl-phenyl)-hexahydro-pyrrolo[1,2-c]imidazol-3-one;

(rac)-2-(2,5-Dichloro-phenyl)-7a-methyl-hexahydro-pyrrolo[1,2-c]imidazol-3-one; and (rac)-6-Benzyloxy-2-((Z)-5-hydroxy-adamantan-2-yl)-7a-methyl-hexahydro-pyrrolo[1,2-c]imidazol-3-one.

9. The compound according to claim 1, selected from:

(rac)-2-[1-(2-Chloro-phenyl)-ethyl]-7a-methyl-hexahydro-pyrrolo[1,2-c]imidazol-3-one;

(rac)-2-[1-(2,4-Difluoro-phenyl)-ethyl]-7a-methyl-hexahydro-pyrrolo[1,2-c]imidazol-3-one;

(rac)-2-[1-(3-Chloro-phenyl)-ethyl]-7a-methyl-hexahydro-pyrrolo[1,2-c]imidazol-3-one;

(rac)-6-Benzyloxy-2-((E)-5-hydroxy-adamantan-2-yl)-7a-methyl-hexahydro-pyrrolo[1,2-c]imidazol-3-one;

(rac)-7a-(2-Fluoro-phenyl)-2-((Z)-5-hydroxy-adamantan-2-yl)-hexahydro-pyrrolo[1,2-c]imidazol-3-one;

(rac)-7a-(2-Fluoro-phenyl)-2-((E)-5-hydroxy-adamantan-2-yl)-hexahydro-pyrrolo[1,2-c]imidazol-3-one;

(rac)-7a-(3-Chloro-phenyl)-2-((E)-5-hydroxy-adamantan-2-yl)-hexahydro-pyrrolo[1,2-c]imidazol-3-one;

(rac)-7a-(4-Fluoro-phenyl)-2-((E)-5-hydroxy-adamantan-2-yl)-hexahydro-pyrrolo[1,2-c]imidazol-3-one;

(rac)-7a-(2,4-Dichloro-phenyl)-2-((E)-5-hydroxy-adamantan-2-yl)-hexahydro-pyrrolo[1,2-cimidazol-3-one;

(E)-4-[(R)-7a-(4-Fluoro-phenyl)-3-oxo-tetrahydro-pyrrolo[1,2-c]imidazol-2-yl]-adamantane-1-carboxylic acid amide;

(Z)-4-((rac)-7a-Cyclopropylmethyl-3-oxo-tetrahydro-pyrrolo[1,2-c]imidazol-2-yl)-adamantane-1-carboxylic acid amide;

(E)-4-((rac)-7a-Cyclopropylmethyl-3-oxo-tetrahydro-pyrrolo[1,2-c]imidazol-2-yl)-adamantane-1-carboxylic acid amide;

4-[(rac)-7a-(4-Fluoro-phenyl)-3-oxo-tetrahydro-pyrrolo[1,2-c]imidazol-2-yl]-bicyclo[2.2.2]octane-1-carboxylic acid amide;

(S)-7a-(4-Fluoro-phenyl)-2-((E)-5-hydroxy-adamantan-2-yl)-hexahydro-pyrrolo[1,2-c]imidazol-3-one;

(R)-7a-(4-Fluoro-phenyl)-2-((E)-5-hydroxy-adamantan-2-yl)-hexahydro-pyrrolo[1,2-c]imidazol-3-one;

(rac)-7a-(2,4-Difluoro-phenyl)-2-((Z)-5-hydroxy-adamantan-2-yl)-hexahydro-pyrrolo[1,2-c]imidazol-3-one;

(rac)-7a-(2,4-Difluoro-phenyl)-2-((E)-5-hydroxy-adamantan-2-yl)-hexahydro-pyrrolo[1,2-c]imidazol-3-one;

(rac)-2-((Z)-5-Hydroxy-adamantan-2-yl)-7a-(3-methoxy-phenyl)-hexahydro-pyrrolo[1,2-c]imidazol-3-one;

(rac)-2-((E)-5-Hydroxy-adamantan-2-yl)-7a-(3-methoxy-phenyl)-hexahydro-pyrrolo[1,2-c]imidazol-3-one;

4-[(rac)-7a-(3-Chloro-phenyl)-3-oxo-tetrahydro-pyrrolo[1,2-c]imidazol-2-yl]-bicyclo[2.2.2]octane-1-carboxylic acid amide;

4-[(S)-7a-(3-Chloro-phenyl)-3-oxo-tetrahydro-pyrrolo[1,2-c]imidazol-2-yl]-bicyclo[2.2.2]octane-1-carboxylic acid amide;

4-[(R)-7a-(3-Chloro-phenyl)-3-oxo-tetrahydro-pyrrolo[1,2-c]imidazol-2-yl]-bicyclo[2.2.2]octane-1-carboxylic acid amide;

4-((rac)-7a-Cyclopropylmethyl-3-oxo-tetrahydro-pyrrolo[1,2-c]imidazol-2-yl)-bicyclo[2.2.2]octane-1-carboxylic acid amide;

4-(S)-7a-Cyclopropylmethyl-3-oxo-tetrahydro-pyrrolo[1,2-c]imidazol-2-yl)-bicyclo[2.2.2]octane-1-carboxylic acid amide; and 4-(R)-7a-Cyclopropylmethyl-3-oxo-tetrahydro-pyrrolo[1,2-c]imidazol-2-yl)-bicyclo[2.2.2]octane-1-carboxylic acid amide.

10. The compound according to claim 1 selected from:
(S)-2-((E)-5-Hydroxy-adamantan-2-yl)-7a-methyl-hexahydro-pyrrolo[1,2-c]imidazol-3-one;
(rac)-2-((E)-5-Hydroxy-adamantan-2-yl)-8a-methyl-hexahydro-imidazo[1,5-a]pyridin-3-one;
6-[(S)-2-((E)-5-Hydroxy-adamantan-2-yl)-3-oxo-tetrahydro-pyrrolo[1,2-c]imidazol-7a-ylmethoxy]-nicotinonitrile;
(E/Z)-4-[(rac)-7a-(5-Cyano-pyridin-2-yloxymethyl)-3-oxo-tetrahydro-pyrrolo[1,2-c]imidazol-2-yl]-adamantane-1-carboxylic acid amide;
(rac)-7a-Cyclopropylmethyl-2-((E)-5-hydroxy-adamantan-2-yl)-hexahydro-pyrrolo[1,2-c]imidazol-3-one;
(rac)-7a-(3-Chloro-phenyl)-2-((E)-5-hydroxy-adamantan-2-yl)-hexahydro-pyrrolo[1,2-c]imidazol-3-one;
(E)-4-[(R)-7a-(4-Fluoro-phenyl)-3-oxo-tetrahydro-pyrrolo[1,2-c]imidazol-2-yl]-adamantane-1-carboxylic acid amide;
(E)-4-((rac)-7a-Cyclopropylmethyl-3-oxo-tetrahydro-pyrrolo[1,2-c]imidazol-2-yl]-adamantane-1-carboxylic acid amide;
4-[(rac)-7a-(4-Fluoro-phenyl)-3-oxo-tetrahydro-pyrrolo[1,2-c]imidazol-2-yl]-bicyclo[2.2.2]octane-1-carboxylic acid amide; and
(R)-7a-(4-Fluoro-phenyl)-2-((E)-5-hydroxy-adamantan-2-yl)-hexahydro-pyrrolo[1,2-c]imidazol-3-one.

11. A pharmaceutical composition, comprising a therapeutically effective amount of a compound according to claim 1 and a therapeutically acceptable carrier.

* * * * *